United States Patent
Timmer et al.

(10) Patent No.: US 9,914,765 B2
(45) Date of Patent: **\*Mar. 13, 2018**

(54) WAP DOMAIN FUSION POLYPEPTIDES AND METHODS OF USE THEREOF

(71) Applicant: InhibRx LLC, La Jolla, CA (US)

(72) Inventors: John C. Timmer, La Jolla, CA (US); Brendan P. Eckelman, La Jolla, CA (US); Grant B. Guenther, La Jolla, CA (US); Peter L. Nguy, La Jolla, CA (US); Henry Chan, La Jolla, CA (US); Quinn Deveraux, La Jolla, CA (US)

(73) Assignee: Inhibrx LP, La Jolla, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/616,351

(22) Filed: Feb. 6, 2015

(65) Prior Publication Data
US 2015/0147324 A1    May 28, 2015

Related U.S. Application Data

(63) Continuation of application No. 13/536,987, filed on Jun. 28, 2012, now Pat. No. 8,986,688.
(Continued)

(51) Int. Cl.
*C07K 14/00* (2006.01)
*C07K 16/00* (2006.01)
(Continued)

(52) U.S. Cl.
CPC ........ *C07K 14/811* (2013.01); *C07K 14/7151* (2013.01); *C07K 14/7155* (2013.01); *C07K 14/765* (2013.01); *C07K 14/8121* (2013.01); *C07K 14/8125* (2013.01); *C07K 16/241* (2013.01); *A61K 38/00* (2013.01);
(Continued)

(58) Field of Classification Search
CPC .......... A61J 48/00; A61J 38/00; A61J 9/0019; C07K 14/705; C07K 2319/30; C07K 2319/32; C07K 14/00
See application file for complete search history.

(56) References Cited

U.S. PATENT DOCUMENTS 3,773,919 A   11/1973  Boswell et al.
4,522,811 A    6/1985  Eppstein et al.
(Continued)

FOREIGN PATENT DOCUMENTS

EP    0662516 A1   7/1995
EP    2726093      5/2014
(Continued)

OTHER PUBLICATIONS

Abe et al. "Expression of the Secretory Leukoprotease Inhibitor Gene in Epithelial Cells." *J. Clin. Invest.* 87.6(1991):2207-2215.
(Continued)

*Primary Examiner* — Cherie M Stanfield
(74) *Attorney, Agent, or Firm* — Cooley LLP; Ivor R. Elrifi; Christina K. Stock

(57) ABSTRACT

This invention relates to fusion proteins that include a whey acidic protein (WAP) domain-containing polypeptide and a second polypeptide. Additionally, the invention relates to fusion proteins that include a WAP domain-containing polypeptide a second polypeptide, and a third polypeptide. The second and/or third polypeptides of the fusion proteins of the invention are a Fe polypeptide; an albumin polypeptide; a cytokine targeting polypeptide; or a serpin polypeptide. This invention also relates to methods of using such molecules in a variety of therapeutic and diagnostic indications, as well as methods of producing such molecules.

7 Claims, 7 Drawing Sheets

Related U.S. Application Data

(60) Provisional application No. 61/638,516, filed on Apr. 26, 2012, provisional application No. 61/638,168, filed on Apr. 25, 2012, provisional application No. 61/565,625, filed on Dec. 1, 2011, provisional application No. 61/502,052, filed on Jun. 28, 2011.

(51) Int. Cl.
*C07K 14/81* (2006.01)
*C07K 16/24* (2006.01)
*C07K 14/715* (2006.01)
*C07K 14/765* (2006.01)
*A61K 38/00* (2006.01)

(52) U.S. Cl.
CPC ... *C07K 2317/522* (2013.01); *C07K 2317/524* (2013.01); *C07K 2317/526* (2013.01); *C07K 2317/53* (2013.01); *C07K 2317/56* (2013.01); *C07K 2319/00* (2013.01); *C07K 2319/30* (2013.01); *C07K 2319/31* (2013.01); *C07K 2319/70* (2013.01)

(56) References Cited

U.S. PATENT DOCUMENTS

| | | | |
|---|---|---|---|
| 6,737,056 B1 | 5/2004 | Presta | |
| 7,271,149 B2 | 9/2007 | Glaesner et al. | |
| 8,252,905 B2 | 8/2012 | Furusako et al. | |
| 8,980,266 B2* | 3/2015 | Eckelman | C07K 14/7151 424/134.1 |
| 8,986,688 B2* | 3/2015 | Timmer | C07K 16/241 424/134.1 |
| 2003/0040097 A1* | 2/2003 | Ruben | C07K 14/8121 435/226 |
| 2003/0073217 A1* | 4/2003 | Barr | C07K 14/811 435/184 |
| 2003/0190311 A1* | 10/2003 | Dall'Acqua | A61K 47/48507 424/130.1 |
| 2003/0190331 A1 | 10/2003 | Francon et al. | |
| 2006/0030527 A1 | 2/2006 | Mjalli et al. | |
| 2006/0073132 A1 | 4/2006 | Congote et al. | |
| 2006/0276633 A1* | 12/2006 | Jung | A61K 47/48415 530/387.1 |
| 2006/0292643 A1* | 12/2006 | Goletz | A61K 51/08 435/7.23 |
| 2007/0004909 A1* | 1/2007 | Johnson | C07K 16/283 530/388.8 |
| 2007/0041907 A1 | 2/2007 | Ober | |
| 2009/0304696 A1* | 12/2009 | Lawson | C07K 16/00 424/135.1 |
| 2010/0256065 A1 | 10/2010 | Filbin et al. | |
| 2010/0261248 A1 | 10/2010 | Kim et al. | |
| 2011/0021755 A1 | 1/2011 | Lazar et al. | |
| 2012/0056065 A1 | 3/2012 | Andersson | |
| 2015/0104410 A1* | 4/2015 | Eckelman | C07K 14/8125 424/85.1 |

FOREIGN PATENT DOCUMENTS

| | | |
|---|---|---|
| WO | WO-01/40249 A1 | 6/2001 |
| WO | WO-03/021273 A2 | 3/2003 |
| WO | WO-2005/086915 A2 | 9/2005 |
| WO | WO-2009/045508 A1 | 4/2009 |
| WO | WO 2009/083880 A1 | 7/2009 |
| WO | WO-2011107505 A1 | 9/2011 |
| WO | WO 2013/003649 A2 | 1/2013 |

OTHER PUBLICATIONS

Ashcroft et al. "Secretory Leukocyte Protease Inhibitor Mediates Non-Redundant Functions Necessary for Normal Wound Healing." *Nat. Med.* 6.10(2000):1147-1153.

Baldrick. "Pharmaceutical Excipient Development: The Need for Preclinical Guidance." *Reg. Toxicol. Pharmacol.* 32.2(2000):210-218.

Bergenfeldt et al. "Release of Neutrophil Proteinase 4(3) and Leukocyte Elastase During Phagocytosis and Their Interaction With Proteinase Inhibitors." *Scand. J. Clin. Lab. Invest.* 52.8(1992):823-829.

Bergenfeldt et al. "The Elimination of Secretory Leukocyte Protease Inhibitor (SLPI) after Intravenous Injection in Dog and Man." *Scand. J. Clin. Lab. Invest.* 50(1990):729-737.

Charman. "Lipids, Lipophilic Drugs, and Oral Drug Delivery: Some Emerging Concepts." *J. Pharm. Sci.* 89.8(2000):967-978.

Chattopadhyay et al. "Salivary Secretory Leukocyte Protease Inhibitor and Oral Candidiasis in Human Immunodeficiency Virus Type 1-Infected Persons." *Infect. Immun.* 72.4(2004):1956-1963.

Cowan et al. "Elafin, a Serine Elastase Inhibitor, Attenuates Post-Cardiac Transplant Coronary Arteriopathy and Reduces Myocardial Necrosis in Rabbits After Heterotropic Cardiac Transplantation." *J. Clin. Invest.* 97.11(1996):2452-2468.

Dall'Acqua et al. "Properties of Human IgG1s Engineered for Enhanced Binding to the Neonatal Fc Receptor (FcRn)." *J. Biol. Chem.* 281.33(2006):23514-23524.

Ding et al. "Secretory Leukocyte Protease Inhibitor Interferes With Uptake of Lipopolysaccharide by Macrophages." *Infect. Immun.* 67.9(1999):4485-4489.

Doumas et al. "Anti-Inflammatory and Antimicrobial Roles of Secretory Leukocyte Protease Inhibitor." *Infect. Immun.* 73.2(2005):1271-1274.

Eisenberg et al. "Location of the Protease-Inhibitory Region of Secretory Leukocyte Protease Inhibitor." *J. Biol. Chem.* 265.14(1990):7976-7981.

Fath et al. "Interaction of Secretory Leukocyte Protease Inhibitor With Heparin Inhibits Proteases Involved in Asthma." *J. Biol. Chem.* 273.22(1998):13563-13569.

Feuerstein. "Inflammation and Stroke: Therapeutic Effects of Adenoviral Expression of Secretory Leukocyte Protease Inhibitor." *Front. Biosci.* 11(2006):1750-1757.

Forteza et al. "Secretory Leukocyte Protease Inhibitor, but not α-1 Protease Inhibitor, Blocks Tryptase-Induced Bronchoconstriction." *Pulm. Pharmacol. Ther.* 14(2001):107-110.

Gast et al. "Pharmacokinetics and Distribution of Recombinant Secretory Leukocyte Proteinase Inhibitor in Rats." *Am. Rev. Respir. Dis.* 141(1990):889-894.

GenBank Accession No. AAA51546.1, Oct. 30, 1994.
GenBank Accession No. AAA51547.1, Oct. 30, 1994.
GenBank Accession No. AAB59375.1, Nov. 1, 1994.
GenBank Accession No. AAB59495.1, Aug. 8, 1995.
GenBank Accession No. AAD19661.1, May 30, 2002.
GenBank Accession No. AAG00546.1, Jun. 14, 2001.
GenBank Accession No. AAG00547.1, Jun. 14, 2001.
GenBank Accession No. AAG00548.1, Jun. 14, 2001.
GenBank Accession No. AAH20708.1, Jul. 15, 2006.
GenBank Accession No. AAH44829.2, Mar. 9, 2007.
GenBank Accession No. AAH53369.1, Jul. 15, 2006.
GenBank Accession No. BAA02441.1, Jul. 21, 2005.
GenBank Accession No. BAG35125.1, May 24, 2008.
GenBank Accession No. CAA25838.1, Mar. 5, 2002.
GenBank Accession No. CAA28187.1, Apr. 18, 2005.
GenBank Accession No. CAA28188.1, Oct. 7, 2008.
GenBank Accession No. CAA34982.1, Apr. 18, 2005.
GenBank Accession No. CAB64235.1, Jan. 13, 2009.
GenBank Accession No. CAJ15161.1, Jul. 8, 2007.
GenBank Accession No. EAW75813.1, Feb. 4, 2010.
GenBank Accession No. EAW75814.1, Feb. 4, 2010.
GenBank Accession No. EAW75869.1, Feb. 4, 2010.
GenBank Accession No. NP_000286.3, Jun. 27, 2012.
GenBank Accession No. NP_001002235.1, Jun. 27, 2012.
GenBank Accession No. NP_001002236.1, Jun. 27, 2012.
GenBank Accession No. NP_001121172, Jun. 27, 2012.
GenBank Accession No. NP_001121174.1, Jun. 27, 2012.
GenBank Accession No. NP_001121175.1, Jun. 27, 2012.
GenBank Accession No. NP_001121176.1, Jun. 27, 2012.
GenBank Accession No. NP_001121177.1, Jun. 27, 2012.

(56) References Cited

OTHER PUBLICATIONS

GenBank Accession No. NP_001121178.1, Jun. 27, 2012.
GenBank Accession No. NP_001121179.1, Jun. 27, 2012.
GenBank Accession No. NP_002629.1, Jun. 27, 2012.
GenBank Accession No. NP_003055.1, Jun. 27, 2012.
GenBank Accession No. NP_065131.1, Apr. 29, 2012.
GenBank Accession No. NP_542181.1, Mar. 25, 2012.
GenBank Accession No. O95925.1, Jun. 13, 2012.
GenBank Accession No. P01009.3, Jun. 13, 2012.
GenBank Accession No. P03973.2, Jun. 13, 2012.
GenBank Accession No. P19957.3, Jun. 13, 2012.
GenBank Accession No. Q8IUB2.1, Jun. 13, 2012.
Ghasemlou et al. "Beneficial Effects of Secretory Leukocyte Protease Inhibitor After Spinal Cord Injury." *Brain*. 133(2010):126-138.
Hamaker et al. "Chromatography for Rapid Buffer Exchange and Refolding of Secretory Leukocyte Protease Inhibitor." *Biotechnol. Prog*. 12(1996):184-189.
Hiemstra et al. "Antibacterial Activity of Antileukoprotease." *Infect. Immun*. 64.11(1996):4520-4524.
Hocini et al. "Secretory Leukocyte Protease Inhibitor Inhibits Infection of Monocytes and Lymphocytes With Human Immunodeficiency Virus Type 1 but Does Not Interfere With Transcytosis of Cell-Associated Virus Across Tight Epithelial Barriers." *Clin. Diagn. Immunol*. 7.3(2000):515-518.
Huang. "Receptor-Fc Fusion Therapeutics, Traps, and MIMETIBODY™ Technology." *Curr. Opin. Biotechnol*. 20(2009):692-699.
Jazayeri et al. "Fc-Based Cytokines: Prospects for Engineering Superior Therapeutics." *BioDrugs*. 22.1(2008):11-26.
Jin et al. "Lipopolysaccharide-Related Stimuli Induce Expression of the Secretory Leukocyte Protease Inhibitor, a Macrophage-Derived Lipopolysaccharide Inhibitor." *Infect. Immun*. 66.6(1998):2447-2452.
Karnaukhova et al. "Recombinant Human α-1 Proteinase Inhibitor: Towards Therapeutic Use." *Amino Acids*. 30.4(2006):317-332.
King et al. "Innate Immune Defences in the Human Endometrium." *Reprod. Biol. Endocrinol*. 1(2003):116.
Kontermann. "Strategies to Extend Plasma Half-Lives of Recombinant Antibodies." *BioDrugs*. 23.2(2009):93-109.
Lentsch et al. "Inhibition of NF-κB Activation and Augmentation of IκBβ by Secretory Leukocyte Protease Inhibitor During Lung Inflammation." *Am. J. Pathol*. 154.1(1999):239-247.
Li et al. "Expression and Characterization of Recombinant Human Secretory Leukocyte Protease Inhibitor (SLPI) Protein from Pichia pastoris." *Protein Exp. Purif*. 67(2009):175-181.
Lucey et al. "Recombinant Human Secretory Leukocyte-Protease Inhibitor: In Vitro Properties, and Amelioration of Human Neutrophil Elastase-Induced Emphysema and Secretory Cell Metaplasia in the Hamster." *J. Lab. Clin. Med*. 115(1990):224-232.
Marasco et al. "Design, Intracellular Expression, and Activity of a Human Anti-Human Immunodeficiency Virus Type 1 jp120 Single-Chain Antibody." *PNAS*. 90.16(1993):7889-7893.
Marino et al. "Secretory Leukocyte Protease Inhibitor Plays an Important Role in the Regulation of Allergic Asthma in Mice." *J. Immunol*. 186(2011):4433-4442.
Maruyama et al. "Modulation of Secretory Leukoprotease Inhibitor Gene Expression in Human Bronchial Epithelial Cells by Phorbol Ester." *J. Clin. Invest*. 94.1(1994):368-375.
McMichael et al. "The Antimicrobial Antiproteinase Elafin Binds to Lipopolysaccharide and Modulates Macrophage Responses." *Am. J. Respir. Cell Mol. Biol*. 32(2005):443-452.
McNeely et al. "Inhibition of Human Immunodeficiency Virus Type 1 Infectivity by Secretory Leukocyte Protease Inhibitor Occurs Prior to Viral Reverse Transcription." *Blood*. 90.3(1997):1141-1149.
McNeely et al. "Secretory Leukocyte Protease Inhibitor: A Human Saliva Protein Exhibiting Anti-Human Immunodeficiency Virus 1 Activity in Vitro." *J. Clin. Invest*. 96.1(1995):456-464.
Meyer-Hoffert et al. "Supernatants of Pseudomonas aeruginosa Induce the Pseudomonas-Specific Antibiotic Elafin in Human Keratinocytes." *Exp. Dermatol*. 12.4(2003):418-425.
Mulligan et al. "Anti-Inflammatory Effects of Mutant Forms of Secretory Leukocyte Protease Inhibitor." *Am. J. Pathol*. 156.3(2000):1033-1039.
Nakamura et al. "Increased Susceptibility to LBS-Induced Endotoxin Shock in Secretory Leukoprotease Inhibitor (SLPI)-Deficient Mice." *J. Exp. Med*. 197.5(2003):669-674.
Nishimura et al. "Potent Antimycobacterial Activity of Mouse Secretory Leukocyte Protease Inhibitor." *J. Immunol*. 180(2008):4032-4039.
Pillay et al. "Secretory Leukocyte Protease Inhibitor in Vaginal Fluids and Perinatal Human Immunodeficiency Virus Type 1 Transmission." *J. Infect. Dis*. 183.4(2001):653-656.
Powell et al. "Compendium of Excipients for Parental Formulations." *PDA J. Pharm. Sci. Technol*. 52(1998):238-311.
Rabinovitch. "EVE and Beyond, Retro and Prospective Insights." *Am. J. Physiol. Lung Cell. Mol. Physiol*. 277(1999): L5-L12.
Ranganathan et al. "The Whey Acid Protein Family: A New Signature Motif and Three-Dimensional Structure by Comparative Modeling." *J. Mol. Graphics Modell*. 17.2(1999):106-113.
Rao et al. "Interaction of Secretory Leukocyte Protease Inhibitor With Proteinase-3." *Am. J. Respir. Cell Mol. Biol*. 8(1993):612-616.
Sallenave et al. "Regulation of Pulmonary and Systemic Bacterial Lipopolysaccharide Responses in Transgenic Mice Expressing Human Elafin." *Infect. Immun*. 71.7(2003):3766-3774.
Sallenave. "Secretory Leukocyte Protease Inhibitor and Elafin/Trappin-2: versatile mucosal antimicrobials and regulators of immunity." *Am. J. Respir. Cell Mol. Biol*. 42(2010):635-643.
Schalkwijk et al. "The Trappin Gene Family: Proteins Defined by an N-Terminal Transglutaminase Substrate Domain and a C-Terminal Four-Disulphide Core." *Biochem. J*. 340(1999):569-577.
Schmidt. "Fusions-Proteins as Biopharmaceuticals: Applications and Challenges." *Curr. Opin. Drug Disc. Dev*. 12.2(2009):284-295.
Schneeberger et al. "The Effect of Secretory Leukocyte Protease Inhibitor (SLPI) on Ischemia/Reperfusion Injury in Cardiac Transplantation." *Am. J. Transplant*. 8(2008):773-782.
Scott et al. "SLPI and Elafin: Multifunctional Antiproteases of the WFDC Family." *Biochem. Soc. Trans*. 39.5(2011):1437-1440.
Shaw and Wiedow. "Therapeutic Potential of Human Elafin." *Biochem. Soc. Trans*. 39.5(2011):1450-1454.
Si-Tahar et al. "Constitutive and Regulated Secretion of Secretory Leukocyte Proteinase Inhibitor by Human Intestinal Epithelial Cells." *Gastroenterology*. 118.6(2000):1061-1071.
Simpson et al. "Elafin (Elastase-Specific Inhibitor) has Anti-Microbial Activity Against Gram-Positive and Gram-Negative Respiratory Pathogens." *FEBS Lett*. 452.3(1999):309-313.
Simpson et al. "Regulation of Adenovirus-Mediated Elafin Transgene Expression by Bacterial Lipopolysaccharide." *Hum. Gene Ther*. 12(2001):1395-1406.
Song et al. "Secretory Leukocyte Protease Inhibitor Suppresses the Inflammation and Joint Damage of Bacterial Cell Wall-Induced Arthritis." *J. Exp. Med*. 190.4(1999):535-542.
Stolk et al. "Lipopolysaccharide-Induced Alveolar Wall Destruction in the Hamster is Inhibited by Intratracheal Treatment With r-Secretory Leukocyte Protease Inhibitor." *Ann. N.Y. Acad. Sci*. 624(1991):350-352.
Stromatt. "Secretory Leukocyte Protease Inhibitor in Cystic Fibrosis." *Agents Actions Suppl*. 42(1993):103-110.
Taggart et al. "Secretory Leucoprotease Inhibitor Binds to NK-κB Binding Sites in Monocytes and Inhibits p65 Binding." *J. Exp. Med*. 202.12(2005):1659-1668.
Tomee et al. "Antileukoprotease: An Endogenous Protein in the Innate Mucosal Defense Against Fungi." *J. Infect. Dis*. 176.3(1997):740-747.
UniProtKB/Swiss-Pro P01861 (IGHG4_HUMAN), Jul. 21, 1986.
Wang. "Lyophilization and Development of Solid Protein Pharmaceuticals." *Int. J. Pharm*. 203.1-2(2000):1-60.
Wang et al. "Up-Regulation of Secretory Leukocyte Protease Inhibitor (SLPI) in the Brain After Ischemic Stroke: Adenoviral Expression of SLPI Protects Brain From Ischemic Injury." *Mol. Pharmacol*. 64.4(2003):833-840.

(56) References Cited

OTHER PUBLICATIONS

Watterberg et al. "Secretory Leukocyte Protease Inhibitor and Lung Inflammation in Developing Bronchopulmonary Dysplasia." *J. Pediatr.* 125(1994):264-269.
Weldon et al. "The Role of Secretory Leucoprotease Inhibitor in the Resolution of Inflammatory Responses." Biochem. Soc. Trans. 35(2007):273-276.
Wiedow et al. "Antileukoprotease in Human Skin: An Antibiotic Peptide Constitutively Produced by Keratinocytes." *Biochem. Biophys. Res. Commun.* 248.3(1998):904-909.
Williams et al. "SLPI and Elafin: One Glove, Many Fingers." *Clin. Sci.* 110.1(2006):21-35.
Wright et al. "Secretory Leukocyte Protease Inhibitor Prevents Allergen-Induced Pulmonary Responses in Animal Models of Asthma." *J. Pharmacol. Exp. Ther.* 289.2(1999):1007-1014.
Ying and Simon. "Kinetics of the Inhibition of Proteinase 3 by Elafin." *Am. J. Respir. Cell Mol. Biol.* 24(2001):83-89.
Zalevsky et al. "Enhanced Antibody Half-Life Improves in vivo Activity." Nat. Biotechnol. 28.2(2010):157-159.
Bingle et al. "The putative ovarian tumour marker gene HE4 (WFDC2), is expressed in normal tissues and undergoes complex alternative splicing to yield multiple protein isoforms." Oncogene, 2002, vol. 21(17), p. 2768-2773.
Carrell, et al. "Structure and variation of human α1-antitrypsin." Nature, 1982, vol. 298, p. 329-334.
Kalsheker "Alpha 1-Antitrypsin: Structure, Function and Molecular Biology of the Gene," Bioscience Reports, 1989, vol. 9, p. 129-138.
Ohbayashi, "Current Synthetic Inhibitors of Human Neutrophil Elastase in 2005," Expert Opin. Ther. Patents, 2005, vol. 15, p. 759-771.
Nocentini, G. et al. "Glucocorticoid-Induced Tumor Necrosis Factor Receptor-Related (GITR)-Fc Fusion Protein Inhibits GITR Triggering and Protects from the Inflammatory Response after Spinal Cord Injury", Mol. Pharmacol., vol. 73, 2008, p. 1610-1621.
Therapeutic Research, vol. 19, 1998, p. 204-208.
Notice of Reasons for Rejection (Translation) issued for Japanese Application No. JP2014-519054, dated Dec. 13, 2016.

\* cited by examiner

1. Elafin-Fc
2. SLPI-Fc

| | |
|---|---|
| WAP Domain Containing Polypeptide: |  |
| Antibody Heavy Chain Constant or Fc Region: |  |
| Heavy Chain Variable Region |  |
| Antibody Light Chain Constant Region |  |
| Heavy Chain Variable Region |  |
| Cytokine Receptor: |  |
| Hinge/Linker: |  |

1. AAT-hFc-Elafin
2. AAT-hFc-SLPI

SEQUENCE LISTING

```
<160> NUMBER OF SEQ ID NOS: 51

<210> SEQ ID NO 1
<211> LENGTH: 132
<212> TYPE: PRT
<213> ORGANISM: Artificial Sequence
<220> FEATURE:
<223> OTHER INFORMATION: chemically synthesized

<400> SEQUENCE: 1

Met Lys Ser Ser Gly Leu Phe Pro Phe Leu Val Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                85                  90                  95

Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
        115                 120                 125

Pro Val Lys Ala
    130
```

-continued

<210> SEQ ID NO 2
<211> LENGTH: 107
<212> TYPE: PRT
<213> ORGANISM: Artificial Sequence
<220> FEATURE:
<223> OTHER INFORMATION: chemically synthesized

<400> SEQUENCE: 2

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Met
                85                  90                  95

Cys Gly Lys Ser Cys Val Ser Pro Val Lys Ala
            100                 105

<210> SEQ ID NO 3
<211> LENGTH: 51
<212> TYPE: PRT
<213> ORGANISM: Artificial Sequence
<220> FEATURE:
<223> OTHER INFORMATION: chemically synthesized

<400> SEQUENCE: 3

Thr Arg Arg Lys Pro Gly Lys Cys Pro Val Thr Tyr Gly Gln Cys Leu
1               5                   10                  15

Met Leu Asn Pro Pro Asn Phe Cys Glu Met Asp Gly Gln Cys Lys Arg
            20                  25                  30

Asp Leu Lys Cys Cys Met Gly Met Cys Gly Lys Ser Cys Val Ser Pro
        35                  40                  45

Val Lys Ala
    50

<210> SEQ ID NO 4
<211> LENGTH: 117
<212> TYPE: PRT
<213> ORGANISM: Artificial Sequence
<220> FEATURE:
<223> OTHER INFORMATION: chemically synthesized

<400> SEQUENCE: 4

Met Arg Ala Ser Ser Phe Leu Ile Val Val Phe Leu Ile Ala Gly
1               5                   10                  15

Thr Leu Val Leu Glu Ala Ala Val Thr Gly Val Pro Val Lys Gly Gln
            20                  25                  30

Asp Thr Val Lys Gly Arg Val Pro Phe Asn Gly Gln Asp Pro Val Lys
        35                  40                  45

Gly Gln Val Ser Val Lys Gly Gln Asp Lys Val Lys Ala Gln Glu Pro
    50                  55                  60

Val Lys Gly Pro Val Ser Thr Lys Pro Gly Ser Cys Pro Ile Ile Leu
65                  70                  75                  80

Ile Arg Cys Ala Met Leu Asn Pro Pro Asn Arg Cys Leu Lys Asp Thr
                85                  90                  95

```
Asp Cys Pro Gly Ile Lys Lys Cys Cys Glu Gly Ser Cys Gly Met Ala
            100                 105                 110
Cys Phe Val Pro Gln
        115

<210> SEQ ID NO 5
<211> LENGTH: 95
<212> TYPE: PRT
<213> ORGANISM: Artificial Sequence
<220> FEATURE:
<223> OTHER INFORMATION: chemically synthesized

<400> SEQUENCE: 5

Ala Val Thr Gly Val Pro Val Lys Gly Gln Asp Thr Val Lys Gly Arg
1               5                   10                  15
Val Pro Phe Asn Gly Gln Asp Pro Val Lys Gly Gln Val Ser Val Lys
            20                  25                  30
Gly Gln Asp Lys Val Lys Ala Gln Glu Pro Val Lys Gly Pro Val Ser
        35                  40                  45
Thr Lys Pro Gly Ser Cys Pro Ile Ile Leu Ile Arg Cys Ala Met Leu
    50                  55                  60
Asn Pro Pro Asn Arg Cys Leu Lys Asp Thr Asp Cys Pro Gly Ile Lys
65                  70                  75                  80
Lys Cys Cys Glu Gly Ser Cys Gly Met Ala Cys Phe Val Pro Gln
                85                  90                  95

<210> SEQ ID NO 6
<211> LENGTH: 49
<212> TYPE: PRT
<213> ORGANISM: Artificial Sequence
<220> FEATURE:
<223> OTHER INFORMATION: chemically synthesized

<400> SEQUENCE: 6

Val Ser Thr Lys Pro Gly Ser Cys Pro Ile Ile Leu Ile Arg Cys Ala
1               5                   10                  15
Met Leu Asn Pro Pro Asn Arg Cys Leu Lys Asp Thr Asp Cys Pro Gly
            20                  25                  30
Ile Lys Lys Cys Cys Glu Gly Ser Cys Gly Met Ala Cys Phe Val Pro
        35                  40                  45
Gln

<210> SEQ ID NO 7
<211> LENGTH: 217
<212> TYPE: PRT
<213> ORGANISM: Artificial Sequence
<220> FEATURE:
<223> OTHER INFORMATION: chemically synthesized

<400> SEQUENCE: 7

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 8
<211> LENGTH: 216
<212> TYPE: PRT
<213> ORGANISM: Artificial Sequence
<220> FEATURE:
<223> OTHER INFORMATION: chemically synthesized

<400> SEQUENCE: 8

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215
```

```
<210> SEQ ID NO 9
<211> LENGTH: 217
<212> TYPE: PRT
<213> ORGANISM: Artificial Sequence
<220> FEATURE:
<223> OTHER INFORMATION: chemically synthesized

<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 10
<211> LENGTH: 216
<212> TYPE: PRT
<213> ORGANISM: Artificial Sequence
<220> FEATURE:
<223> OTHER INFORMATION: chemically synthesized

<400> SEQUENCE: 10

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Glu Gly Asn Val Phe
            180                 185                 190

Ser Cys Ser Val Met His Glu Ala Leu His Asn His Tyr Thr Gln Lys
        195                 200                 205

Ser Leu Ser Leu Ser Leu Gly Lys
    210                 215

<210> SEQ ID NO 11
<211> LENGTH: 218
<212> TYPE: PRT
<213> ORGANISM: Artificial Sequence
<220> FEATURE:
<223> OTHER INFORMATION: chemically synthesized

<400> SEQUENCE: 11

Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
            20                  25                  30

Gly Phe Ser Pro Arg Gln Ile Gln Val Ser Trp Leu Arg Glu Gly Lys
        35                  40                  45

Gln Val Gly Ser Gly Val Thr Thr Asp Gln Val Gln Ala Glu Ala Lys
    50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
            85                  90                  95

Arg Gly Leu Thr Phe Gln Gln Asn Ala Ser Ser Met Cys Val Pro Asp
        100                 105                 110

Gln Asp Thr Ala Ile Arg Val Phe Ala Ile Pro Pro Ser Phe Ala Ser
    115                 120                 125

Ile Phe Leu Thr Lys Ser Thr Lys Leu Thr Cys Leu Val Thr Asp Leu
130                 135                 140

Thr Thr Tyr Asp Ser Val Thr Ile Ser Trp Thr Arg Gln Asn Gly Glu
145                 150                 155                 160

Ala Val Lys Thr His Thr Asn Ile Ser Glu Ser His Pro Asn Ala Thr
                165                 170                 175

Phe Ser Ala Val Gly Glu Ala Ser Ile Cys Glu Asp Asp Trp Asn Ser
            180                 185                 190

Gly Glu Arg Phe Thr Cys Thr Val Thr His Thr Asp Leu Pro Ser Pro
        195                 200                 205

Leu Lys Gln Thr Ile Ser Arg Pro Lys Gly
    210                 215
```

-continued

```
<210> SEQ ID NO 12
<211> LENGTH: 25
<212> TYPE: PRT
<213> ORGANISM: Artificial Sequence
<220> FEATURE:
<223> OTHER INFORMATION: chemically synthesized

<400> SEQUENCE: 12

Gly Thr Glu Ala Ala Gly Ala Met Phe Leu Glu Ala Ile Pro Met Ser
1               5                   10                  15

Ile Pro Pro Glu Val Lys Phe Asn Lys
            20                  25

<210> SEQ ID NO 13
<211> LENGTH: 394
<212> TYPE: PRT
<213> ORGANISM: Artificial Sequence
<220> FEATURE:
<223> OTHER INFORMATION: chemically synthesized

<400> SEQUENCE: 13

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285
```

```
Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 14
<211> LENGTH: 585
<212> TYPE: PRT
<213> ORGANISM: Artificial Sequence
<220> FEATURE:
<223> OTHER INFORMATION: chemically synthesized

<400> SEQUENCE: 14

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 15
<211> LENGTH: 196
<212> TYPE: PRT
<213> ORGANISM: Artificial Sequence
<220> FEATURE:
<223> OTHER INFORMATION: chemically synthesized

<400> SEQUENCE: 15

Glu Glu Pro Gln Asn Leu Ile Lys Gln Asn Cys Glu Leu Phe Glu Gln
1               5                   10                  15

Leu Gly Glu Tyr Lys Phe Gln Asn Ala Leu Leu Val Arg Tyr Thr Lys
            20                  25                  30

```
Lys Val Pro Gln Val Ser Thr Pro Thr Leu Val Glu Val Ser Arg Asn
            35                  40                  45

Leu Gly Lys Val Gly Ser Lys Cys Cys Lys His Pro Glu Ala Lys Arg
 50                  55                  60

Met Pro Cys Ala Glu Asp Tyr Leu Ser Val Val Leu Asn Gln Leu Cys
 65                  70                  75                  80

Val Leu His Glu Lys Thr Pro Val Ser Asp Arg Val Thr Lys Cys Cys
                 85                  90                  95

Thr Glu Ser Leu Val Asn Arg Arg Pro Cys Phe Ser Ala Leu Glu Val
            100                 105                 110

Asp Glu Thr Tyr Val Pro Lys Glu Phe Asn Ala Glu Thr Phe Thr Phe
            115                 120                 125

His Ala Asp Ile Cys Thr Leu Ser Glu Lys Glu Arg Gln Ile Lys Lys
            130                 135                 140

Gln Thr Ala Leu Val Glu Leu Val Lys His Lys Pro Lys Ala Thr Lys
145                 150                 155                 160

Glu Gln Leu Lys Ala Val Met Asp Asp Phe Ala Ala Phe Val Glu Lys
                165                 170                 175

Cys Cys Lys Ala Asp Asp Lys Glu Thr Cys Phe Ala Glu Glu Gly Lys
            180                 185                 190

Lys Leu Val Ala
            195

<210> SEQ ID NO 16
<211> LENGTH: 339
<212> TYPE: PRT
<213> ORGANISM: Artificial Sequence
<220> FEATURE:
<223> OTHER INFORMATION: chemically synthesized

<400> SEQUENCE: 16

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
                20                  25                  30

Pro Gly Lys Lys Arg Cys Cys Pro Asp Thr Cys Gly Ile Lys Cys Leu
            35                  40                  45

Asp Pro Val Asp Thr Pro Asn Pro Thr Arg Arg Lys Pro Gly Lys Cys
 50                  55                  60

Pro Val Thr Tyr Gly Gln Cys Leu Met Leu Asn Pro Pro Asn Phe Cys
 65                  70                  75                  80

Glu Met Asp Gly Gln Cys Lys Arg Asp Leu Lys Cys Cys Met Gly Met
                85                  90                  95

Cys Gly Lys Ser Cys Val Ser Pro Val Lys Ala Glu Pro Lys Ser Cys
            100                 105                 110

Asp Lys Thr His Thr Cys Pro Pro Cys Pro Ala Pro Glu Leu Leu Gly
            115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190
```

```
Arg Val Val Ser Val Leu Thr Val Leu His Gln Asp Trp Leu Asn Gly
            195                 200                 205

Lys Glu Tyr Lys Cys Lys Val Ser Asn Lys Ala Leu Pro Ala Pro Ile
210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
            245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
            275                 280                 285

Val Leu Asp Ser Asp Gly Ser Phe Phe Leu Tyr Ser Lys Leu Thr Val
            290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
            325                 330                 335

Pro Gly Lys

<210> SEQ ID NO 17
<211> LENGTH: 335
<212> TYPE: PRT
<213> ORGANISM: Artificial Sequence
<220> FEATURE:
<223> OTHER INFORMATION: chemically synthesized

<400> SEQUENCE: 17

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
            35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Met
            85                  90                  95

Cys Gly Lys Ser Cys Val Ser Pro Val Lys Ala Glu Arg Lys Cys Cys
            100                 105                 110

Val Glu Cys Pro Pro Cys Pro Ala Pro Pro Val Ala Gly Pro Ser Val
            115                 120                 125

Phe Leu Phe Pro Pro Lys Pro Lys Asp Thr Leu Met Ile Ser Arg Thr
            130                 135                 140

Pro Glu Val Thr Cys Val Val Val Asp Val Ser His Glu Asp Pro Glu
145                 150                 155                 160

Val Gln Phe Asn Trp Tyr Val Asp Gly Val Glu Val His Asn Ala Lys
            165                 170                 175

Thr Lys Pro Arg Glu Glu Gln Phe Asn Ser Thr Phe Arg Val Val Ser
            180                 185                 190

Val Leu Thr Val Val His Gln Asp Trp Leu Asn Gly Lys Glu Tyr Lys
            195                 200                 205
```

```
Cys Lys Val Ser Asn Lys Gly Leu Pro Ala Pro Ile Glu Lys Thr Ile
    210                 215                 220

Ser Lys Thr Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Met Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 18
<211> LENGTH: 339
<212> TYPE: PRT
<213> ORGANISM: Artificial Sequence
<220> FEATURE:
<223> OTHER INFORMATION: chemically synthesized

<400> SEQUENCE: 18

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
                20                  25                  30

Pro Gly Lys Lys Arg Cys Cys Pro Asp Thr Cys Gly Ile Lys Cys Leu
            35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Leu
                85                  90                  95

Cys Gly Lys Ser Cys Val Ser Pro Val Lys Ala Glu Pro Lys Ser Cys
            100                 105                 110

Asp Lys Thr His Thr Cys Pro Pro Cys Pro Ala Pro Glu Leu Leu Gly
    115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
    195                 200                 205

Lys Glu Tyr Lys Cys Lys Val Ser Asn Lys Ala Leu Pro Ala Pro Ile
210                 215                 220

Glu Lys Thr Ile Ser Lys Ala Lys Gly Gln Pro Arg Glu Pro Gln Val
225                 230                 235                 240
```

```
Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
                275                 280                 285

Val Leu Asp Ser Asp Gly Ser Phe Phe Leu Tyr Ser Lys Leu Thr Val
        290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 19
<211> LENGTH: 339
<212> TYPE: PRT
<213> ORGANISM: Artificial Sequence
<220> FEATURE:
<223> OTHER INFORMATION: chemically synthesized

<400> SEQUENCE: 19

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Leu
                85                  90                  95

Cys Gly Lys Ser Cys Val Ser Pro Val Lys Ala Glu Pro Lys Ser Cys
            100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Tyr
    130                 135                 140

Ile Thr Arg Glu Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255
```

```
Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
        290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 20
<211> LENGTH: 339
<212> TYPE: PRT
<213> ORGANISM: Artificial Sequence
<220> FEATURE:
<223> OTHER INFORMATION: chemically synthesized

<400> SEQUENCE: 20

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Leu
                85                  90                  95

Cys Gly Lys Ser Cys Val Ser Pro Val Lys Ala Glu Pro Lys Ser Cys
            100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270
```

```
Trp Glu Ser Asn Gly Gln Pro Glu Asn Asn Tyr Lys Thr Thr Pro Pro
            275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Leu
305                 310                 315                 320

His Glu Ala Leu His Ser His Tyr Thr Gln Lys Ser Leu Ser Leu Ser
                325                 330                 335

Pro Gly Lys

<210> SEQ ID NO 21
<211> LENGTH: 327
<212> TYPE: PRT
<213> ORGANISM: Artificial Sequence
<220> FEATURE:
<223> OTHER INFORMATION: chemically synthesized

<400> SEQUENCE: 21

Ala Val Thr Gly Val Pro Val Lys Gly Gln Asp Thr Val Lys Gly Arg
1               5                   10                  15

Val Pro Phe Asn Gly Gln Asp Pro Val Lys Gly Gln Val Ser Val Lys
            20                  25                  30

Gly Gln Asp Lys Val Lys Ala Gln Glu Pro Val Lys Gly Pro Val Ser
        35                  40                  45

Thr Lys Pro Gly Ser Cys Pro Ile Ile Leu Ile Arg Cys Ala Met Leu
    50                  55                  60

Asn Pro Pro Asn Arg Cys Leu Lys Asp Thr Asp Cys Pro Gly Ile Lys
65                  70                  75                  80

Lys Cys Cys Glu Gly Ser Cys Gly Met Ala Cys Phe Val Pro Gln Glu
                85                  90                  95

Pro Lys Ser Cys Asp Lys Thr His Thr Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Lys Leu Thr Val Asp Lys Ser Arg Trp Gln Gln Gly Asn Val Phe Ser
        290                 295                 300
Cys Ser Val Leu His Glu Ala Leu His Ser His Tyr Thr Gln Lys Ser
305                 310                 315                 320
Leu Ser Leu Ser Pro Gly Lys
                325

<210> SEQ ID NO 22
<211> LENGTH: 451
<212> TYPE: PRT
<213> ORGANISM: Artificial Sequence
<220> FEATURE:
<223> OTHER INFORMATION: chemically synthesized

<400> SEQUENCE: 22

Ser Gly Lys Ser Phe Lys Ala Gly Val Cys Pro Pro Lys Ser Ala
1               5                   10                  15
Gln Cys Leu Arg Tyr Lys Lys Pro Glu Cys Gln Ser Asp Trp Gln Cys
            20                  25                  30
Pro Gly Lys Lys Arg Cys Cys Pro Asp Thr Cys Gly Ile Lys Cys Leu
            35                  40                  45
Asp Pro Val Asp Thr Pro Asn Pro Thr Arg Arg Lys Pro Gly Lys Cys
50                  55                  60
Pro Val Thr Tyr Gly Gln Cys Leu Met Leu Asn Pro Pro Asn Phe Cys
65                  70                  75                  80
Glu Met Asp Gly Gln Cys Lys Arg Asp Leu Lys Cys Cys Met Gly Leu
                85                  90                  95
Cys Gly Lys Ser Cys Val Ser Pro Val Lys Ala Glu Pro Lys Ser Cys
            100                 105                 110
Asp Lys Thr His Thr Cys Pro Pro Cys Pro Ala Pro Glu Leu Leu Gly
            115                 120                 125
Gly Pro Ser Val Phe Leu Phe Pro Pro Lys Pro Lys Asp Thr Leu Met
        130                 135                 140
Ile Ser Arg Thr Pro Glu Val Thr Cys Val Val Val Asp Val Ser His
145                 150                 155                 160
Glu Asp Pro Glu Val Lys Phe Asn Trp Tyr Val Asp Gly Val Glu Val
                165                 170                 175
His Asn Ala Lys Thr Lys Pro Arg Glu Glu Gln Tyr Asn Ser Thr Tyr
            180                 185                 190
Arg Val Val Ser Val Leu Thr Val Leu His Gln Asp Trp Leu Asn Gly
            195                 200                 205
Lys Glu Tyr Lys Cys Lys Val Ser Asn Lys Ala Leu Pro Ala Pro Ile
        210                 215                 220
Glu Lys Thr Ile Ser Lys Ala Lys Gly Gln Pro Arg Glu Pro Gln Val
225                 230                 235                 240
Tyr Thr Leu Pro Pro Ser Arg Asp Glu Leu Thr Lys Asn Gln Val Ser
                245                 250                 255
Leu Thr Cys Leu Val Lys Gly Phe Tyr Pro Ser Asp Ile Ala Val Glu
            260                 265                 270
Trp Glu Ser Asn Gly Gln Pro Glu Asn Asn Tyr Lys Thr Thr Pro Pro
            275                 280                 285
Val Leu Asp Ser Asp Gly Ser Phe Phe Leu Tyr Ser Lys Leu Thr Val
        290                 295                 300
Asp Lys Ser Arg Trp Gln Gln Gly Asn Val Phe Ser Cys Ser Val Met
305                 310                 315                 320
```

His Glu Ala Leu His Asn His Tyr Thr Gln Lys Ser Leu Ser Leu Ser
            325                 330                 335

Pro Gly Lys Ala Ser Thr Gly Ser Ser Gly Lys Ser Phe Lys Ala Gly
        340                 345                 350

Val Cys Pro Pro Lys Lys Ser Ala Gln Cys Leu Arg Tyr Lys Lys Pro
    355                 360                 365

Glu Cys Gln Ser Asp Trp Gln Cys Pro Gly Lys Lys Arg Cys Cys Pro
370                 375                 380

Asp Thr Cys Gly Ile Lys Cys Leu Asp Pro Val Asp Thr Pro Asn Pro
385                 390                 395                 400

Thr Arg Arg Lys Pro Gly Lys Cys Pro Val Thr Tyr Gly Gln Cys Leu
                405                 410                 415

Met Leu Asn Pro Pro Asn Phe Cys Glu Met Asp Gly Gln Cys Lys Arg
            420                 425                 430

Asp Leu Lys Cys Cys Met Gly Leu Cys Gly Lys Ser Cys Val Ser Pro
        435                 440                 445

Val Lys Ala
    450

<210> SEQ ID NO 23
<211> LENGTH: 427
<212> TYPE: PRT
<213> ORGANISM: Artificial Sequence
<220> FEATURE:
<223> OTHER INFORMATION: chemically synthesized

<400> SEQUENCE: 23

Ala Val Thr Gly Val Pro Val Lys Gly Gln Asp Thr Val Lys Gly Arg
1               5                   10                  15

Val Pro Phe Asn Gly Gln Asp Pro Val Lys Gly Gln Val Ser Val Lys
            20                  25                  30

Gly Gln Asp Lys Val Lys Ala Gln Glu Pro Val Lys Gly Pro Val Ser
        35                  40                  45

Thr Lys Pro Gly Ser Cys Pro Ile Ile Leu Ile Arg Cys Ala Met Leu
    50                  55                  60

Asn Pro Pro Asn Arg Cys Leu Lys Asp Thr Asp Cys Pro Gly Ile Lys
65                  70                  75                  80

Lys Cys Cys Glu Gly Ser Cys Gly Met Ala Cys Phe Val Pro Gln Glu
                85                  90                  95

Pro Lys Ser Cys Asp Lys Thr His Thr Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys Ala Ser Thr Gly Ser Ala Val Thr Gly
            325                 330                 335

Val Pro Val Lys Gly Gln Asp Thr Val Lys Gly Arg Val Pro Phe Asn
        340                 345                 350

Gly Gln Asp Pro Val Lys Gly Gln Val Ser Val Lys Gly Gln Asp Lys
    355                 360                 365

Val Lys Ala Gln Glu Pro Val Lys Gly Pro Val Ser Thr Lys Pro Gly
370                 375                 380

Ser Cys Pro Ile Ile Leu Ile Arg Cys Ala Met Leu Asn Pro Pro Asn
385                 390                 395                 400

Arg Cys Leu Lys Asp Thr Asp Cys Pro Gly Ile Lys Lys Cys Cys Glu
            405                 410                 415

Gly Ser Cys Gly Met Ala Cys Phe Val Pro Gln
            420                 425

<210> SEQ ID NO 24
<211> LENGTH: 439
<212> TYPE: PRT
<213> ORGANISM: Artificial Sequence
<220> FEATURE:
<223> OTHER INFORMATION: chemically synthesized

<400> SEQUENCE: 24

Ala Val Thr Gly Val Pro Val Lys Gly Gln Asp Thr Val Lys Gly Arg
1               5                   10                  15

Val Pro Phe Asn Gly Gln Asp Pro Val Lys Gly Gln Val Ser Val Lys
            20                  25                  30

Gly Gln Asp Lys Val Lys Ala Gln Glu Pro Val Lys Gly Pro Val Ser
        35                  40                  45

Thr Lys Pro Gly Ser Cys Pro Ile Ile Leu Ile Arg Cys Ala Met Leu
    50                  55                  60

Asn Pro Pro Asn Arg Cys Leu Lys Asp Thr Asp Cys Pro Gly Ile Lys
65                  70                  75                  80

Lys Cys Cys Glu Gly Ser Cys Gly Met Ala Cys Phe Val Pro Gln Glu
            85                  90                  95

Pro Lys Ser Cys Asp Lys Thr His Thr Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys Ala Ser Thr Gly Ser Ser Gly Lys Ser
                325                 330                 335

Phe Lys Ala Gly Val Cys Pro Pro Lys Ser Ala Gln Cys Leu Arg
            340                 345                 350

Tyr Lys Lys Pro Glu Cys Gln Ser Asp Trp Gln Cys Pro Gly Lys Lys
        355                 360                 365

Arg Cys Cys Pro Asp Thr Cys Gly Ile Lys Cys Leu Asp Pro Val Asp
    370                 375                 380

Thr Pro Asn Pro Thr Arg Arg Lys Pro Gly Lys Cys Pro Val Thr Tyr
385                 390                 395                 400

Gly Gln Cys Leu Met Leu Asn Pro Pro Asn Phe Cys Glu Met Asp Gly
                405                 410                 415

Gln Cys Lys Arg Asp Leu Lys Cys Cys Met Gly Leu Cys Gly Lys Ser
            420                 425                 430

Cys Val Ser Pro Val Lys Ala
        435

<210> SEQ ID NO 25
<211> LENGTH: 439
<212> TYPE: PRT
<213> ORGANISM: Artificial Sequence
<220> FEATURE:
<223> OTHER INFORMATION: chemically synthesized

<400> SEQUENCE: 25

Ser Gly Lys Ser Phe Lys Ala Gly Val Cys Pro Pro Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

```
Glu Met Asp Gly Gln Cys Lys Arg Asp Leu Lys Cys Cys Met Gly Leu
                 85                  90                  95

Cys Gly Lys Ser Cys Val Ser Pro Val Lys Ala Glu Pro Lys Ser Cys
            100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys Ala Ser Thr Gly Ser Ala Val Thr Gly Val Pro Val Lys
            340                 345                 350

Gly Gln Asp Thr Val Lys Gly Arg Val Pro Phe Asn Gly Gln Asp Pro
        355                 360                 365

Val Lys Gly Gln Val Ser Val Lys Gly Gln Asp Lys Val Lys Ala Gln
    370                 375                 380

Glu Pro Val Lys Gly Pro Val Ser Thr Lys Pro Gly Ser Cys Pro Ile
385                 390                 395                 400

Ile Leu Ile Arg Cys Ala Met Leu Asn Pro Pro Asn Arg Cys Leu Lys
                405                 410                 415

Asp Thr Asp Cys Pro Gly Ile Lys Cys Cys Glu Gly Ser Cys Gly
            420                 425                 430

Met Ala Cys Phe Val Pro Gln
            435

<210> SEQ ID NO 26
<211> LENGTH: 329
<212> TYPE: PRT
<213> ORGANISM: Artificial Sequence
<220> FEATURE:
<223> OTHER INFORMATION: chemically synthesized
```

<400> SEQUENCE: 26

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Arg Asn Tyr
            20                  25                  30
Leu Ala Trp Tyr Gln Gln Lys Pro Gly Lys Ala Pro Lys Leu Leu Ile
        35                  40                  45
Tyr Ala Ala Ser Thr Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Arg Tyr Asn Arg Ala Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Ser Gly Gly Ser Ser Gly
210                 215                 220
Lys Ser Phe Lys Ala Gly Val Cys Pro Pro Lys Ser Ala Gln Cys
225                 230                 235                 240
Leu Arg Tyr Lys Lys Pro Glu Cys Gln Ser Asp Trp Gln Cys Pro Gly
                245                 250                 255
Lys Lys Arg Cys Cys Pro Asp Thr Cys Gly Ile Lys Cys Leu Asp Pro
            260                 265                 270
Val Asp Thr Pro Asn Pro Thr Arg Arg Lys Pro Gly Lys Cys Pro Val
        275                 280                 285
Thr Tyr Gly Gln Cys Leu Met Leu Asn Pro Pro Asn Phe Cys Glu Met
        290                 295                 300
Asp Gly Gln Cys Lys Arg Asp Leu Lys Cys Cys Met Gly Met Cys Gly
305                 310                 315                 320
Lys Ser Cys Val Ser Pro Val Lys Ala
                325
```

<210> SEQ ID NO 27
<211> LENGTH: 326
<212> TYPE: PRT
<213> ORGANISM: Artificial Sequence
<220> FEATURE:
<223> OTHER INFORMATION: chemically synthesized

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ala Ser Thr Gly Ser Gly Lys Ser Phe
210                 215                 220

Lys Ala Gly Val Cys Pro Pro Lys Lys Ser Ala Gln Cys Leu Arg Tyr
225                 230                 235                 240

Lys Lys Pro Glu Cys Gln Ser Asp Trp Gln Cys Pro Gly Lys Lys Arg
                245                 250                 255

Cys Cys Pro Asp Thr Cys Gly Ile Lys Cys Leu Asp Pro Val Asp Thr
            260                 265                 270

Pro Asn Pro Thr Arg Arg Lys Pro Gly Lys Cys Pro Val Thr Tyr Gly
        275                 280                 285

Gln Cys Leu Met Leu Asn Pro Pro Asn Phe Cys Glu Met Asp Gly Gln
290                 295                 300

Cys Lys Arg Asp Leu Lys Cys Cys Met Gly Met Cys Gly Lys Ser Cys
305                 310                 315                 320

Val Ser Pro Val Lys Ala
            325
```

<210> SEQ ID NO 28
<211> LENGTH: 566
<212> TYPE: PRT
<213> ORGANISM: Artificial Sequence
<220> FEATURE:
<223> OTHER INFORMATION: chemically synthesized

<400> SEQUENCE: 28

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Ala Ile Thr Trp Asn Ser Gly His Ile Asp Tyr Ala Asp Ser Val
    50                  55                  60
Glu Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly Lys Gly Gly Ser Gly Gly Ser Ser Gly Lys Ser Phe
    450                 455                 460

Lys Ala Gly Val Cys Pro Pro Lys Lys Ser Ala Gln Cys Leu Arg Tyr
465                 470                 475                 480

Lys Lys Pro Glu Cys Gln Ser Asp Trp Gln Cys Pro Gly Lys Lys Arg
            485                 490                 495

Cys Cys Pro Asp Thr Cys Gly Ile Lys Cys Leu Asp Pro Val Asp Thr
            500                 505                 510

Pro Asn Pro Thr Arg Arg Lys Pro Gly Lys Cys Pro Val Thr Tyr Gly
            515                 520                 525

Gln Cys Leu Met Leu Asn Pro Pro Asn Phe Cys Glu Met Asp Gly Gln
            530                 535                 540

Cys Lys Arg Asp Leu Lys Cys Cys Met Gly Met Cys Gly Lys Ser Cys
545                 550                 555                 560

Val Ser Pro Val Lys Ala
                565

<210> SEQ ID NO 29
<211> LENGTH: 563
<212> TYPE: PRT
<213> ORGANISM: Artificial Sequence
<220> FEATURE:
<223> OTHER INFORMATION: chemically synthesized

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ala Ser Thr Gly Ser Ser Gly Lys Ser Phe Lys Ala Gly
    450                 455                 460

Val Cys Pro Pro Lys Ser Ala Gln Cys Leu Arg Tyr Lys Lys Pro
465                 470                 475                 480

Glu Cys Gln Ser Asp Trp Gln Cys Pro Gly Lys Arg Cys Cys Pro
                485                 490                 495

Asp Thr Cys Gly Ile Lys Cys Leu Asp Pro Val Asp Thr Pro Asn Pro
            500                 505                 510

Thr Arg Arg Lys Pro Gly Lys Cys Pro Val Thr Tyr Gly Gln Cys Leu
        515                 520                 525

Met Leu Asn Pro Pro Asn Phe Cys Glu Met Asp Gly Gln Cys Lys Arg
    530                 535                 540

Asp Leu Lys Cys Cys Met Gly Met Cys Gly Lys Ser Cys Val Ser Pro
545                 550                 555                 560

Val Lys Ala

<210> SEQ ID NO 30
<211> LENGTH: 582
<212> TYPE: PRT
<213> ORGANISM: Artificial Sequence
<220> FEATURE:
<223> OTHER INFORMATION: chemically synthesized
```

```
<400> SEQUENCE: 30

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65              70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145             150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225             230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Gln Val Lys Phe Asn Trp Tyr Val Asp Gly Val Gln Val
    290                 295                 300

His Asn Ala Lys Thr Lys Pro Arg Glu Gln Gln Tyr Asn Ser Thr Tyr
305             310                 315                 320

Arg Val Val Ser Val Leu Thr Val Leu His Gln Asn Trp Leu Asp Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385             390                 395                 400

Trp Glu Ser Asn Gly Gln Pro Glu Asn Asn Tyr Lys Thr Thr Pro Pro
                405                 410                 415
```

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys Gly Gly Gly Ser Gly Gly Gly Ser Ser Gly Lys Ser Phe
465                 470                 475                 480

Lys Ala Gly Val Cys Pro Pro Lys Lys Ser Ala Gln Cys Leu Arg Tyr
            485                 490                 495

Lys Lys Pro Glu Cys Gln Ser Asp Trp Gln Cys Pro Gly Lys Lys Arg
            500                 505                 510

Cys Cys Pro Asp Thr Cys Gly Ile Lys Cys Leu Asp Pro Val Asp Thr
            515                 520                 525

Pro Asn Pro Thr Arg Arg Lys Pro Gly Lys Cys Pro Val Thr Tyr Gly
            530                 535                 540

Gln Cys Leu Met Leu Asn Pro Pro Asn Phe Cys Glu Met Asp Gly Gln
545                 550                 555                 560

Cys Lys Arg Asp Leu Lys Cys Cys Met Gly Met Cys Gly Lys Ser Cys
            565                 570                 575

Val Ser Pro Val Lys Ala
            580

<210> SEQ ID NO 31
<211> LENGTH: 579
<212> TYPE: PRT
<213> ORGANISM: Artificial Sequence
<220> FEATURE:
<223> OTHER INFORMATION: chemically synthesized

<400> SEQUENCE: 31

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
            130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Gln Val Lys Phe Asn Trp Tyr Val Asp Gly Val Gln Val
290                 295                 300

His Asn Ala Lys Thr Lys Pro Arg Glu Gln Gln Tyr Asn Ser Thr Tyr
305                 310                 315                 320

Arg Val Val Ser Val Leu Thr Val Leu His Gln Asn Trp Leu Asp Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys Ala Ser Thr Gly Ser Ser Gly Lys Ser Phe Lys Ala Gly
465                 470                 475                 480

Val Cys Pro Pro Lys Ser Ala Gln Cys Leu Arg Tyr Lys Lys Pro
            485                 490                 495

Glu Cys Gln Ser Asp Trp Gln Cys Pro Gly Lys Lys Arg Cys Cys Pro
            500                 505                 510

Asp Thr Cys Gly Ile Lys Cys Leu Asp Pro Val Asp Thr Pro Asn Pro
        515                 520                 525

Thr Arg Arg Lys Pro Gly Lys Cys Pro Val Thr Tyr Gly Gln Cys Leu
530                 535                 540

Met Leu Asn Pro Pro Asn Phe Cys Glu Met Asp Gly Gln Cys Lys Arg
545                 550                 555                 560

Asp Leu Lys Cys Cys Met Gly Met Cys Gly Lys Ser Cys Val Ser Pro
            565                 570                 575

Val Lys Ala

<210> SEQ ID NO 32
<211> LENGTH: 738
<212> TYPE: PRT
<213> ORGANISM: Artificial Sequence
<220> FEATURE:
<223> OTHER INFORMATION: chemically synthesized

<400> SEQUENCE: 32

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415

Pro Ser Val Phe Leu Phe Pro Pro Lys Pro Lys Asp Thr Leu Met Ile
            420                 425                 430

Ser Arg Thr Pro Glu Val Thr Cys Val Val Val Asp Val Ser His Glu
        435                 440                 445

Asp Pro Glu Val Lys Phe Asn Trp Tyr Val Asp Gly Val Glu Val His
    450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
        515                 520                 525

Thr Leu Pro Pro Ser Arg Asp Glu Leu Thr Lys Asn Gln Val Ser Leu
    530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
    595                 600                 605

Glu Ala Leu His Asn His Tyr Thr Gln Lys Ser Leu Ser Leu Ser Pro
    610                 615                 620

Gly Lys Ala Ser Thr Gly Ser Ser Gly Lys Ser Phe Lys Ala Gly Val
625                 630                 635                 640

Cys Pro Pro Lys Lys Ser Ala Gln Cys Leu Arg Tyr Lys Lys Pro Glu
                645                 650                 655

Cys Gln Ser Asp Trp Gln Cys Pro Gly Lys Lys Arg Cys Cys Pro Asp
            660                 665                 670

Thr Cys Gly Ile Lys Cys Leu Asp Pro Val Asp Thr Pro Asn Pro Thr
    675                 680                 685

Arg Arg Lys Pro Gly Lys Cys Pro Val Thr Tyr Gly Gln Cys Leu Met
    690                 695                 700

Leu Asn Pro Pro Asn Phe Cys Glu Met Asp Gly Gln Cys Lys Arg Asp
705                 710                 715                 720

Leu Lys Cys Cys Met Gly Met Cys Gly Lys Ser Cys Val Ser Pro Val
                725                 730                 735

Lys Ala

<210> SEQ ID NO 33
<211> LENGTH: 726
<212> TYPE: PRT
<213> ORGANISM: Artificial Sequence
<220> FEATURE:
<223> OTHER INFORMATION: chemically synthesized

```
<400> SEQUENCE: 33

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
                405                 410                 415
```

```
Pro Ser Val Phe Leu Phe Pro Pro Lys Pro Lys Asp Thr Leu Met Ile
            420                 425                 430

Ser Arg Thr Pro Glu Val Thr Cys Val Val Asp Val Ser His Glu
        435                 440                 445

Asp Pro Glu Val Lys Phe Asn Trp Tyr Val Asp Gly Val Glu Val His
    450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
                485                 490                 495

Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
        515                 520                 525

Thr Leu Pro Pro Ser Arg Asp Glu Leu Thr Lys Asn Gln Val Ser Leu
    530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
        595                 600                 605

Glu Ala Leu His Asn His Tyr Thr Gln Lys Ser Leu Ser Leu Ser Pro
    610                 615                 620

Gly Lys Ala Ser Thr Gly Ser Ala Val Thr Gly Val Pro Val Lys Gly
625                 630                 635                 640

Gln Asp Thr Val Lys Gly Arg Val Pro Phe Asn Gly Gln Asp Pro Val
                645                 650                 655

Lys Gly Gln Val Ser Val Lys Gly Gln Asp Lys Val Lys Ala Gln Glu
            660                 665                 670

Pro Val Lys Gly Pro Val Ser Thr Lys Pro Gly Ser Cys Pro Ile Ile
    675                 680                 685

Leu Ile Arg Cys Ala Met Leu Asn Pro Pro Asn Arg Cys Leu Lys Asp
690                 695                 700

Thr Asp Cys Pro Gly Ile Lys Lys Cys Cys Glu Gly Ser Cys Gly Met
705                 710                 715                 720

Ala Cys Phe Val Pro Gln
                725

<210> SEQ ID NO 34
<211> LENGTH: 697
<212> TYPE: PRT
<213> ORGANISM: Artificial Sequence
<220> FEATURE:
<223> OTHER INFORMATION: chemically synthesized

<400> SEQUENCE: 34

Ser Gly Lys Ser Phe Lys Ala Gly Val Cys Pro Pro Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45
```

```
Asp Pro Val Asp Thr Pro Asn Pro Thr Arg Arg Lys Pro Gly Lys Cys
 50                  55                  60
Pro Val Thr Tyr Gly Gln Cys Leu Met Leu Asn Pro Pro Asn Phe Cys
 65                  70                  75                  80
Glu Met Asp Gly Gln Cys Lys Arg Asp Leu Lys Cys Cys Met Gly Met
                 85                  90                  95
Cys Gly Lys Ser Cys Val Ser Pro Val Lys Ala Ala Ser Thr Gly Ser
            100                 105                 110
Asp Ala His Lys Ser Glu Val Ala His Arg Phe Lys Asp Leu Gly Glu
            115                 120                 125
Glu Asn Phe Lys Ala Leu Val Leu Ile Ala Phe Ala Gln Tyr Leu Gln
        130                 135                 140
Gln Cys Pro Phe Glu Asp His Val Lys Leu Val Asn Glu Val Thr Glu
145                 150                 155                 160
Phe Ala Lys Thr Cys Val Ala Asp Glu Ser Ala Glu Asn Cys Asp Lys
                165                 170                 175
Ser Leu His Thr Leu Phe Gly Asp Lys Leu Cys Thr Val Ala Thr Leu
            180                 185                 190
Arg Glu Thr Tyr Gly Glu Met Ala Asp Cys Cys Ala Lys Gln Glu Pro
        195                 200                 205
Glu Arg Asn Glu Cys Phe Leu Gln His Lys Asp Asp Asn Pro Asn Leu
        210                 215                 220
Pro Arg Leu Val Arg Pro Glu Val Asp Val Met Cys Thr Ala Phe His
225                 230                 235                 240
Asp Asn Glu Glu Thr Phe Leu Lys Lys Tyr Leu Tyr Glu Ile Ala Arg
                245                 250                 255
Arg His Pro Tyr Phe Tyr Ala Pro Glu Leu Leu Phe Phe Ala Lys Arg
            260                 265                 270
Tyr Lys Ala Ala Phe Thr Glu Cys Cys Gln Ala Ala Asp Lys Ala Ala
        275                 280                 285
Cys Leu Leu Pro Lys Leu Asp Glu Leu Arg Asp Glu Gly Lys Ala Ser
290                 295                 300
Ser Ala Lys Gln Arg Leu Lys Cys Ala Ser Leu Gln Lys Phe Gly Glu
305                 310                 315                 320
Arg Ala Phe Lys Ala Trp Ala Val Ala Arg Leu Ser Gln Arg Phe Pro
                325                 330                 335
Lys Ala Glu Phe Ala Glu Val Ser Lys Leu Val Thr Asp Leu Thr Lys
            340                 345                 350
Val His Thr Glu Cys Cys His Gly Asp Leu Leu Glu Cys Ala Asp Asp
        355                 360                 365
Arg Ala Asp Leu Ala Lys Tyr Ile Cys Glu Asn Gln Asp Ser Ile Ser
        370                 375                 380
Ser Lys Leu Lys Glu Cys Cys Glu Lys Pro Leu Leu Glu Lys Ser His
385                 390                 395                 400
Cys Ile Ala Glu Val Glu Asn Asp Glu Met Pro Ala Asp Leu Pro Ser
                405                 410                 415
Leu Ala Ala Asp Phe Val Glu Ser Lys Asp Val Cys Lys Asn Tyr Ala
            420                 425                 430
Glu Ala Lys Asp Val Phe Leu Gly Met Phe Leu Tyr Glu Tyr Ala Arg
        435                 440                 445
Arg His Pro Asp Tyr Ser Val Val Leu Leu Leu Arg Leu Ala Lys Thr
450                 455                 460
```

Tyr Glu Thr Thr Leu Glu Lys Cys Cys Ala Ala Asp Pro His Glu
465                 470                 475                 480

Cys Tyr Ala Lys Val Phe Asp Glu Phe Lys Pro Leu Val Glu Pro
            485                 490                 495

Gln Asn Leu Ile Lys Gln Asn Cys Glu Leu Phe Glu Gln Leu Gly Glu
        500                 505                 510

Tyr Lys Phe Gln Asn Ala Leu Leu Val Arg Tyr Thr Lys Lys Val Pro
    515                 520                 525

Gln Val Ser Thr Pro Thr Leu Val Glu Val Ser Arg Asn Leu Gly Lys
530                 535                 540

Val Gly Ser Lys Cys Cys Lys His Pro Glu Ala Lys Arg Met Pro Cys
545                 550                 555                 560

Ala Glu Asp Tyr Leu Ser Val Val Leu Asn Gln Leu Cys Val Leu His
            565                 570                 575

Glu Lys Thr Pro Val Ser Asp Arg Val Thr Lys Cys Cys Thr Glu Ser
        580                 585                 590

Leu Val Asn Arg Arg Pro Cys Phe Ser Ala Leu Glu Val Asp Glu Thr
    595                 600                 605

Tyr Val Pro Lys Glu Phe Asn Ala Glu Thr Phe Thr Phe His Ala Asp
610                 615                 620

Ile Cys Thr Leu Ser Glu Lys Glu Arg Gln Ile Lys Lys Gln Thr Ala
625                 630                 635                 640

Leu Val Glu Leu Val Lys His Lys Pro Lys Ala Thr Lys Glu Gln Leu
            645                 650                 655

Lys Ala Val Met Asp Asp Phe Ala Ala Phe Val Glu Lys Cys Cys Lys
        660                 665                 670

Ala Asp Asp Lys Glu Thr Cys Phe Ala Glu Glu Gly Lys Lys Leu Val
    675                 680                 685

Ala Ala Ser Gln Ala Ala Leu Gly Leu
690                 695

<210> SEQ ID NO 35
<211> LENGTH: 308
<212> TYPE: PRT
<213> ORGANISM: Artificial Sequence
<220> FEATURE:
<223> OTHER INFORMATION: chemically synthesized

<400> SEQUENCE: 35

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65              70                  75                  80

Glu Met Asp Gly Gln Cys Lys Arg Asp Leu Lys Cys Cys Met Gly Met
            85                  90                  95

Cys Gly Lys Ser Cys Val Ser Pro Val Lys Ala Ala Ser Thr Gly Ser
        100                 105                 110

Glu Glu Pro Gln Asn Leu Ile Lys Gln Asn Cys Glu Leu Phe Glu Gln
    115                 120                 125

```
Leu Gly Glu Tyr Lys Phe Gln Asn Ala Leu Leu Val Arg Tyr Thr Lys
        130                 135                 140

Lys Val Pro Gln Val Ser Thr Pro Thr Leu Val Glu Val Ser Arg Asn
145                 150                 155                 160

Leu Gly Lys Val Gly Ser Lys Cys Cys Lys His Pro Glu Ala Lys Arg
                165                 170                 175

Met Pro Cys Ala Glu Asp Tyr Leu Ser Val Val Leu Asn Gln Leu Cys
            180                 185                 190

Val Leu His Glu Lys Thr Pro Val Ser Asp Arg Val Thr Lys Cys Cys
        195                 200                 205

Thr Glu Ser Leu Val Asn Arg Arg Pro Cys Phe Ser Ala Leu Glu Val
210                 215                 220

Asp Glu Thr Tyr Val Pro Lys Glu Phe Asn Ala Glu Thr Phe Thr Phe
225                 230                 235                 240

His Ala Asp Ile Cys Thr Leu Ser Glu Lys Glu Arg Gln Ile Lys Lys
                245                 250                 255

Gln Thr Ala Leu Val Glu Leu Val Lys His Lys Pro Lys Ala Thr Lys
            260                 265                 270

Glu Gln Leu Lys Ala Val Met Asp Asp Phe Ala Ala Phe Val Glu Lys
        275                 280                 285

Cys Cys Lys Ala Asp Asp Lys Glu Thr Cys Phe Ala Glu Glu Gly Lys
290                 295                 300

Lys Leu Val Ala
305

<210> SEQ ID NO 36
<211> LENGTH: 685
<212> TYPE: PRT
<213> ORGANISM: Artificial Sequence
<220> FEATURE:
<223> OTHER INFORMATION: chemically synthesized

<400> SEQUENCE: 36

Ala Val Thr Gly Val Pro Val Lys Gly Gln Asp Thr Val Lys Gly Arg
1               5                   10                  15

Val Pro Phe Asn Gly Gln Asp Pro Val Lys Gly Gln Val Ser Val Lys
                20                  25                  30

Gly Gln Asp Lys Val Lys Ala Gln Glu Pro Val Lys Gly Pro Val Ser
            35                  40                  45

Thr Lys Pro Gly Ser Cys Pro Ile Ile Leu Ile Arg Cys Ala Met Leu
        50                  55                  60

Asn Pro Pro Asn Arg Cys Leu Lys Asp Thr Asp Cys Pro Gly Ile Lys
65                  70                  75                  80

Lys Cys Cys Glu Gly Ser Cys Gly Met Ala Cys Phe Val Pro Gln Ala
                85                  90                  95

Ser Thr Gly Ser Asp Ala His Lys Ser Glu Val Ala His Arg Phe Lys
            100                 105                 110

Asp Leu Gly Glu Glu Asn Phe Lys Ala Leu Val Leu Ile Ala Phe Ala
        115                 120                 125

Gln Tyr Leu Gln Gln Cys Pro Phe Glu Asp His Val Lys Leu Val Asn
130                 135                 140

Glu Val Thr Glu Phe Ala Lys Thr Cys Val Ala Asp Glu Ser Ala Glu
145                 150                 155                 160

Asn Cys Asp Lys Ser Leu His Thr Leu Phe Gly Asp Lys Leu Cys Thr
                165                 170                 175
```

-continued

Val Ala Thr Leu Arg Glu Thr Tyr Gly Met Ala Asp Cys Cys Ala
            180                 185                 190

Lys Gln Glu Pro Glu Arg Asn Glu Cys Phe Leu Gln His Lys Asp Asp
            195                 200                 205

Asn Pro Asn Leu Pro Arg Leu Val Arg Pro Glu Val Asp Val Met Cys
210                 215                 220

Thr Ala Phe His Asp Asn Glu Glu Thr Phe Leu Lys Lys Tyr Leu Tyr
225                 230                 235                 240

Glu Ile Ala Arg Arg His Pro Tyr Phe Tyr Ala Pro Glu Leu Leu Phe
            245                 250                 255

Phe Ala Lys Arg Tyr Lys Ala Ala Phe Thr Glu Cys Cys Gln Ala Ala
            260                 265                 270

Asp Lys Ala Ala Cys Leu Leu Pro Lys Leu Asp Glu Leu Arg Asp Glu
            275                 280                 285

Gly Lys Ala Ser Ser Ala Lys Gln Arg Leu Lys Cys Ala Ser Leu Gln
            290                 295                 300

Lys Phe Gly Glu Arg Ala Phe Lys Ala Trp Ala Val Ala Arg Leu Ser
305                 310                 315                 320

Gln Arg Phe Pro Lys Ala Glu Phe Ala Glu Val Ser Lys Leu Val Thr
            325                 330                 335

Asp Leu Thr Lys Val His Thr Glu Cys Cys His Gly Asp Leu Leu Glu
            340                 345                 350

Cys Ala Asp Asp Arg Ala Asp Leu Ala Lys Tyr Ile Cys Glu Asn Gln
            355                 360                 365

Asp Ser Ile Ser Ser Lys Leu Lys Glu Cys Cys Glu Lys Pro Leu Leu
            370                 375                 380

Glu Lys Ser His Cys Ile Ala Glu Val Glu Asn Asp Glu Met Pro Ala
385                 390                 395                 400

Asp Leu Pro Ser Leu Ala Ala Asp Phe Val Glu Ser Lys Asp Val Cys
            405                 410                 415

Lys Asn Tyr Ala Glu Ala Lys Asp Val Phe Leu Gly Met Phe Leu Tyr
            420                 425                 430

Glu Tyr Ala Arg Arg His Pro Asp Tyr Ser Val Val Leu Leu Leu Arg
            435                 440                 445

Leu Ala Lys Thr Tyr Glu Thr Thr Leu Glu Lys Cys Cys Ala Ala Ala
450                 455                 460

Asp Pro His Glu Cys Tyr Ala Lys Val Phe Asp Glu Phe Lys Pro Leu
465                 470                 475                 480

Val Glu Glu Pro Gln Asn Leu Ile Lys Gln Asn Cys Glu Leu Phe Glu
            485                 490                 495

Gln Leu Gly Glu Tyr Lys Phe Gln Asn Ala Leu Leu Val Arg Tyr Thr
            500                 505                 510

Lys Lys Val Pro Gln Val Ser Thr Pro Thr Leu Val Glu Val Ser Arg
            515                 520                 525

Asn Leu Gly Lys Val Gly Ser Lys Cys Cys Lys His Pro Glu Ala Lys
            530                 535                 540

Arg Met Pro Cys Ala Glu Asp Tyr Leu Ser Val Val Leu Asn Gln Leu
545                 550                 555                 560

Cys Val Leu His Glu Lys Thr Pro Val Ser Asp Arg Val Thr Lys Cys
            565                 570                 575

Cys Thr Glu Ser Leu Val Asn Arg Arg Pro Cys Phe Ser Ala Leu Glu
            580                 585                 590

```
Val Asp Glu Thr Tyr Val Pro Lys Glu Phe Asn Ala Glu Thr Phe Thr
            595                 600                 605

Phe His Ala Asp Ile Cys Thr Leu Ser Glu Lys Glu Arg Gln Ile Lys
    610                 615                 620

Lys Gln Thr Ala Leu Val Glu Leu Val Lys His Lys Pro Lys Ala Thr
625                 630                 635                 640

Lys Glu Gln Leu Lys Ala Val Met Asp Asp Phe Ala Ala Phe Val Glu
                645                 650                 655

Lys Cys Cys Lys Ala Asp Asp Lys Glu Thr Cys Phe Ala Glu Glu Gly
            660                 665                 670

Lys Lys Leu Val Ala Ala Ser Gln Ala Ala Leu Gly Leu
                675                 680                 685

<210> SEQ ID NO 37
<211> LENGTH: 296
<212> TYPE: PRT
<213> ORGANISM: Artificial Sequence
<220> FEATURE:
<223> OTHER INFORMATION: chemically synthesized

<400> SEQUENCE: 37

Ala Val Thr Gly Val Pro Val Lys Gly Gln Asp Thr Val Lys Gly Arg
1               5                   10                  15

Val Pro Phe Asn Gly Gln Asp Pro Val Lys Gly Gln Val Ser Val Lys
                20                  25                  30

Gly Gln Asp Lys Val Lys Ala Gln Glu Pro Val Lys Gly Pro Val Ser
            35                  40                  45

Thr Lys Pro Gly Ser Cys Pro Ile Ile Leu Ile Arg Cys Ala Met Leu
50                  55                  60

Asn Pro Pro Asn Arg Cys Leu Lys Asp Thr Asp Cys Pro Gly Ile Lys
65                  70                  75                  80

Lys Cys Cys Glu Gly Ser Cys Gly Met Ala Cys Phe Val Pro Gln Ala
                85                  90                  95

Ser Thr Gly Ser Glu Glu Pro Gln Asn Leu Ile Lys Gln Asn Cys Glu
            100                 105                 110

Leu Phe Glu Gln Leu Gly Glu Tyr Lys Phe Gln Asn Ala Leu Leu Val
        115                 120                 125

Arg Tyr Thr Lys Lys Val Pro Gln Val Ser Thr Pro Thr Leu Val Glu
    130                 135                 140

Val Ser Arg Asn Leu Gly Lys Val Gly Ser Lys Cys Cys Lys His Pro
145                 150                 155                 160

Glu Ala Lys Arg Met Pro Cys Ala Glu Asp Tyr Leu Ser Val Val Leu
                165                 170                 175

Asn Gln Leu Cys Val Leu His Glu Lys Thr Pro Val Ser Asp Arg Val
            180                 185                 190

Thr Lys Cys Cys Thr Glu Ser Leu Val Asn Arg Arg Pro Cys Phe Ser
        195                 200                 205

Ala Leu Glu Val Asp Glu Thr Tyr Val Pro Lys Glu Phe Asn Ala Glu
    210                 215                 220

Thr Phe Thr Phe His Ala Asp Ile Cys Thr Leu Ser Glu Lys Glu Arg
225                 230                 235                 240

Gln Ile Lys Lys Gln Thr Ala Leu Val Glu Leu Val Lys His Lys Pro
                245                 250                 255

Lys Ala Thr Lys Glu Gln Leu Lys Ala Val Met Asp Asp Phe Ala Ala
            260                 265                 270
```

```
Phe Val Glu Lys Cys Cys Lys Ala Asp Asp Lys Glu Thr Cys Phe Ala
        275                 280                 285

Glu Glu Gly Lys Lys Leu Val Ala
        290                 295

<210> SEQ ID NO 38
<211> LENGTH: 25
<212> TYPE: PRT
<213> ORGANISM: Artificial Sequence
<220> FEATURE:
<223> OTHER INFORMATION: chemically synthesized

<400> SEQUENCE: 38

Gly Thr Glu Ala Ala Gly Ala Glu Phe Leu Glu Ala Ile Pro Leu Ser
1               5                   10                  15

Ile Pro Pro Glu Val Lys Phe Asn Lys
            20                  25

<210> SEQ ID NO 39
<211> LENGTH: 107
<212> TYPE: PRT
<213> ORGANISM: Artificial Sequence
<220> FEATURE:
<223> OTHER INFORMATION: chemically synthesized

<400> SEQUENCE: 39

Ser Gly Lys Ser Phe Lys Ala Gly Val Cys Pro Pro Lys Lys Ser Ala
1               5                   10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Leu
                85                  90                  95

Cys Gly Lys Ser Cys Val Ser Pro Val Lys Ala
            100                 105

<210> SEQ ID NO 40
<211> LENGTH: 217
<212> TYPE: PRT
<213> ORGANISM: Artificial Sequence
<220> FEATURE:
<223> OTHER INFORMATION: chemically synthesized

<400> SEQUENCE: 40

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215
```

<210> SEQ ID NO 41
<211> LENGTH: 217
<212> TYPE: PRT
<213> ORGANISM: Artificial Sequence
<220> FEATURE:
<223> OTHER INFORMATION: chemically synthesized

<400> SEQUENCE: 41

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Leu His Glu Ala Leu His Ser His Tyr Thr Gln
        195                 200                 205
Lys Ser Leu Ser Leu Ser Pro Gly Lys
    210                 215
```

```
<210> SEQ ID NO 42
<211> LENGTH: 107
<212> TYPE: PRT
<213> ORGANISM: Artificial Sequence
<220> FEATURE:
<223> OTHER INFORMATION: chemically synthesized

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: chemically synthesized

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 44
<211> LENGTH: 116
<212> TYPE: PRT
<213> ORGANISM: Artificial Sequence
<220> FEATURE:
<223> OTHER INFORMATION: chemically synthesized

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45
```

```
Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu
        115

<210> SEQ ID NO 45
<211> LENGTH: 335
<212> TYPE: PRT
<213> ORGANISM: Artificial Sequence
<220> FEATURE:
<223> OTHER INFORMATION: chemically synthesized

<400> SEQUENCE: 45

Val Thr Val Ser Ser Ala Ser Thr Lys Gly Pro Ser Val Phe Pro Leu
 1               5                  10                  15

Ala Pro Ser Ser Lys Ser Thr Ser Gly Gly Thr Ala Ala Leu Gly Cys
                 20                  25                  30

Leu Val Lys Asp Tyr Phe Pro Glu Pro Val Thr Val Ser Trp Asn Ser
             35                  40                  45

Gly Ala Leu Thr Ser Gly Val His Thr Phe Pro Ala Val Leu Gln Ser
 50                  55                  60

Ser Gly Leu Tyr Ser Leu Ser Ser Val Val Thr Val Pro Ser Ser Ser
 65                  70                  75                  80

Leu Gly Thr Gln Thr Tyr Ile Cys Asn Val Asn His Lys Pro Ser Asn
                 85                  90                  95

Thr Lys Val Asp Lys Lys Val Glu Pro Lys Ser Cys Asp Lys Thr His
                100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285
```

```
Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 46
<211> LENGTH: 235
<212> TYPE: PRT
<213> ORGANISM: Artificial Sequence
<220> FEATURE:
<223> OTHER INFORMATION: chemically synthesized

<400> SEQUENCE: 46

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 47
<211> LENGTH: 218
<212> TYPE: PRT
<213> ORGANISM: Artificial Sequence
<220> FEATURE:
<223> OTHER INFORMATION: chemically synthesized

<400> SEQUENCE: 47

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
                20                  25                  30
```

```
Val Val Val Asp Val Ser His Glu Asp Pro Gln Val Lys Phe Asn Trp
         35                  40                  45
Tyr Val Asp Gly Val Gln Val His Asn Ala Lys Thr Lys Pro Arg Glu
 50                  55                  60
Gln Gln Tyr Asn Ser Thr Tyr Arg Val Val Ser Val Leu Thr Val Leu
 65                  70                  75                  80
His Gln Asn Trp Leu Asp Gly Lys Glu Tyr Lys Cys Lys Val Ser Asn
                 85                  90                  95
Lys Ala Leu Pro Ala Pro Ile Glu Lys Thr Ile Ser Lys Ala Lys Gly
                100                 105                 110
Gln Pro Arg Glu Pro Gln Val Tyr Thr Leu Pro Pro Ser Arg Glu Glu
            115                 120                 125
Met Thr Lys Asn Gln Val Ser Leu Thr Cys Leu Val Lys Gly Phe Tyr
        130                 135                 140
Pro Ser Asp Ile Ala Val Glu Trp Glu Ser Asn Gly Gln Pro Glu Asn
145                 150                 155                 160
Asn Tyr Lys Thr Thr Pro Pro Val Leu Asp Ser Asp Gly Ser Phe Phe
                165                 170                 175
Leu Tyr Ser Lys Leu Thr Val Asp Lys Ser Arg Trp Gln Gln Gly Asn
                180                 185                 190
Val Phe Ser Cys Ser Val Met His Glu Ala Leu His Asn His Tyr Thr
            195                 200                 205
Gln Lys Ser Leu Ser Leu Ser Pro Gly Lys
        210                 215

<210> SEQ ID NO 48
<211> LENGTH: 15
<212> TYPE: PRT
<213> ORGANISM: Artificial Sequence
<220> FEATURE:
<223> OTHER INFORMATION: hinge region

<400> SEQUENCE: 48

Glu Pro Lys Ser Cys Asp Lys Thr His Thr Cys Pro Pro Cys Pro
1               5                   10                  15

<210> SEQ ID NO 49
<211> LENGTH: 12
<212> TYPE: PRT
<213> ORGANISM: Artificial Sequence
<220> FEATURE:
<223> OTHER INFORMATION: hinge region

<400> SEQUENCE: 49

Glu Arg Lys Cys Cys Val Glu Cys Pro Pro Cys Pro
1               5                   10

<210> SEQ ID NO 50
<211> LENGTH: 5
<212> TYPE: PRT
<213> ORGANISM: Artificial Sequence
<220> FEATURE:
<223> OTHER INFORMATION: linker

<400> SEQUENCE: 50

Ala Ser Thr Gly Ser
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: linker

<400> SEQUENCE: 51

Gly Gly Gly Ser Gly Gly Gly Ser
1               5
```

WAP DOMAIN FUSION POLYPEPTIDES AND METHODS OF USE THEREOF

RELATED APPLICATIONS

This application is a continuation of U.S. application Ser. No. 13/536,987, filed Jun. 28, 2012, which claims the benefit of U.S. Provisional Application No. 61/502,052, filed Jun. 28, 2011; U.S. Provisional Application No. 61/565,625, filed Dec. 1, 2011; and U.S. Provisional Application No. 61/638,168, filed Apr. 25, 2012; and U.S. Provisional Application No. 61/638,516, filed Apr. 26, 2012. The contents of each of these applications are hereby incorporated by reference in their entirety.

INCORPORATION-BY-REFERENCE OF SEQUENCE LISTING

The contents of the text file named "INHI001C01US_SeqList.txt", which was created on Feb. 6, 2015 and is 128 B in size, are hereby incorporated by reference in their entirety.

FIELD OF THE INVENTION

This invention relates to molecules, particularly polypeptides, more particularly fusion proteins that include a whey acidic protein (WAP) domain-containing polypeptide or an amino acid sequence that is derived from a WAP domain-containing polypeptide, and second polypeptide. Additionally, the invention relates to fusion proteins that include a WAP domain-containing polypeptide or an amino acid sequence that is derived from a WAP domain-containing polypeptide, a second polypeptide, and a third polypeptide. Specifically, this invention relates to fusion proteins that include WAP domain-containing polypeptides and a second polypeptide or fusion proteins that include WAP domain-containing polypeptides, a second polypeptide, and a third polypeptide, where the second and third polypeptides of the fusion proteins of the invention can be at least one of the following: an Fc polypeptide or an amino acid this derived from an Fc polypeptide; an albumin polypeptide, or an amino acid sequence that is derived from an albumin polypeptide; a cytokine targeting polypeptides or an amino acid sequence that is derived from a cytokine targeting polypeptide; and a serpin polypeptide or an amino acid sequence that is derived from a serpin polypeptide. This invention also relates to methods of using such molecules in a variety of therapeutic and diagnostic indications, as well as methods of producing such molecules.

BACKGROUND OF THE INVENTION

Aberrant serine protease activity or an imbalance of protease-to-protease inhibitor can lead to protease-mediated tissue destruction and inflammatory responses. Accordingly, there exists a need for therapeutics and therapies that target aberrant serine protease activity and/or imbalance of protease-to-protease inhibitor.

SUMMARY OF THE INVENTION

The fusion proteins described herein include at least a whey acidic protein (WAP) domain-containing polypeptide or an amino acid sequence that is derived from a WAP domain-containing polypeptide (Polypeptide 1), and second polypeptide (Polypeptide 2). Additionally the fusion proteins described herein include a whey acidic protein (WAP) domain-containing polypeptide or an amino acid sequence that is derived from a WAP domain-containing polypeptide (Polypeptide 1), a second polypeptide (Polypeptide 2), and a third polypeptide (Polypeptide 3). Specifically, this invention relates to fusion proteins that include a WAP domain-containing polypeptide and a second polypeptide or a WAP domain-containing polypeptide, a second polypeptide, and a third polypeptide, where the second and third polypeptides can include at least one of the following: an Fc polypeptide or an amino acid this derived from an Fc polypeptide; an albumin polypeptide or an amino acid sequence that is derived from an albumin polypeptide; a cytokine targeting polypeptides or an amino acid sequence that is derived from a cytokine targeting polypeptide; and a serpin polypeptide or an amino acid sequence that is derived from a serpin polypeptide.

As used interchangeably herein, the terms "fusion protein" and "fusion polypeptide" refer to a WAP domain-containing polypeptide or an amino acid sequence derived from a WAP domain-containing polypeptide operably linked to at least a second polypeptide or an amino acid sequence derived from a second polypeptide. The individualized elements of the fusion protein can be linked in any of a variety of ways, including for example, direct attachment, the use of an intermediate or spacer peptide, the use of a linker region, the use of a hinge region, or the use of both a linker and a hinge region. In some embodiments, the linker region may fall within the sequence of the hinge region, or alternatively, the hinge region may fall within the sequence of the linker region. Preferably, the linker region is a peptide sequence. For example, the linker peptide includes anywhere from zero to 40 amino acids, e.g., from zero to 35 amino acids, from zero to 30 amino acids, from zero to 25 amino acids, or from zero to 20 amino acids. Preferably, the hinge region is a peptide sequence. For example, the hinge peptide includes anywhere from zero to 75 amino acids, e.g., from zero to 70 amino acids, from zero to 65 amino acids or from zero to 62 amino acids. In embodiments where the fusion protein includes both a linker region and hinge region, preferably each of the linker region and the hinge region is a peptide sequence. In these embodiments, the hinge peptide and the linker peptide together include anywhere from zero to 90 amino acids, e.g., from zero to 85 amino acids or from zero to 82 amino acids.

In some embodiments, the WAP domain-based portion and the second polypeptide-based portion of the fusion protein can be linked non-covalently through an intermediate binding polypeptide. In some embodiments, the WAP domain-based portion and the second polypeptide-based portion of the fusion protein may be non-covalently linked.

In some embodiments, fusion proteins according to the invention can have one of the following formulae, in an N-terminus to C-terminus direction or in a C-terminus to N-terminus direction:

Polypeptide $1_{(a)}$-hinge$_m$-Polypeptide $2_{(b)}$

Polypeptide $1_{(a)}$-linker$_n$-Polypeptide $2_{(b)}$

Polypeptide $1_{(a)}$-linker$_n$-hinge$_m$-Polypeptide $2_{(b)}$

Polypeptide $1_{(a)}$-hinge$_m$-linker$_n$-Polypeptide $2_{(b)}$

Polypeptide $1_{(a)}$-Polypeptide $2_{(b)}$-Polypeptide $3_{(c)}$

Polypeptide $1_{(a)}$-hinge$_m$-Polypeptide $2_{(b)}$-hinge$_m$-Polypeptide $3_{(c)}$ Polypeptide $1_{(a)}$-linker$_n$-Polypeptide $2_{(b)}$-linker$_n$-Polypeptide $3_{(c)}$ Polypeptide $1_{(a)}$-hinge$_m$-linker$_n$-Polypeptide $2_{(b)}$-hinge$_m$-linker$_n$-Polypeptide $3_{(c)}$ Polypeptide $1_{(a)}$-linker$_n$-hinge$_m$-Polypeptide $2_{(b)}$-linker$_n$-hinge$_m$-Polypeptide $3_{(c)}$ where n is an integer from zero to 20, where m is an integer from 1 to 62 and where a, b, and c are an integer of at least one. These embodiments include the above formulations and any variation or combination thereof. For example, the order of polypeptides in the formulae also includes Polypeptide $3_{(c)}$-Polypeptide $1_{(a)}$-Polypeptide $2_{(b)}$, Polypeptide $2_{(b)}$-Polypeptide $3_{(c)}$-Polypeptide $1_{(a)}$, or any variation or combination thereof.

In some embodiments, the Polypeptide 1 sequence includes a whey acidic protein (WAP) domain-containing polypeptide. The WAP domain is an evolutionarily conserved sequence motif of 50 amino acids containing eight cysteines found in a characteristic 4-disulfide core arrangement (also called a four-disulfide core motif). The WAP domain sequence motif is a functional motif characterized by serine protease inhibition activity in a number of proteins. WAP domain-containing polypeptides suitable for use in the fusion proteins provided herein include, by way of non-limiting example, secretory leukocyte protease inhibitor (SLPI), Elafin, and Eppin.

In some embodiments, the Polypeptide 1 sequence includes a secretory leukocyte protease inhibitor (SLPI) polypeptide sequence or an amino acid sequence that is derived from SLPI. In some embodiments, the Polypeptide 1 sequence includes a portion of the SLPI protein, such as for example, the WAP2 domain or a sub-portion thereof. In a preferred embodiment, the SLPI polypeptide sequence or an amino acid sequence that is derived from SLPI that is derived from a human SLPI polypeptide sequence.

In some embodiments, the fusion protein includes a full-length human SLPI polypeptide sequence having the following amino acid sequence:

```
                                                          (SEQ ID NO: 1)
  1 MKSSGLFPFL VLLALGTLAP WAVEGSGKSF KAGVCPPKKS AQCLRYKKPE CQSDWQCPGK

61 KRCCPDTCGI KCLDPVDTPN PTRRKPGKCP VTYGQCLMLN PPNFCEMDGQ CKRDLKCCMG

121 MCGKSCVSPV KA
```

In some embodiments, the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 1.

In some embodiments, the fusion protein includes a portion of the full-length human SLPI polypeptide sequence, where the portion has the following amino acid sequence:

```
                                                          (SEQ ID NO: 2)
  1 SGKSFKAGVC PPKKSAQCLR YKKPECQSDW QCPGKKRCCP DTCGIKCLDP VDTPNPTRRK

61 PGKCPVTYGQ CLMLNPPNFC EMDGQCKRDL KCCMGMCGKS CVSPVKA
```

In some embodiments, the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 2.

In some embodiments, the fusion protein includes the WAP2 domain of the full-length human SLPI polypeptide sequence, where the WAP2 domain has the following amino acid sequence:

```
                                                          (SEQ ID NO: 3)
  1 TRRKPGKCPV TYGQCLMLNP PNFCEMDGQC KRDLKCCMGM CGKSCVSPVK A
```

In some embodiments, the fusion protein includes a human SLPI polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 3.

In some embodiments, the SLPI polypeptide sequence is or the amino acid sequence derived from an SLPI polypeptide is derived from, one or more of the human SLPI polypeptide sequences shown in GenBank Accession Nos. CAA28187.1, NP_003055.1, EAW75869.1, P03973.2, AAH20708.1, CAB64235.1, CAA28188.1, AAD19661.1, and/or BAG35125.1.

In some embodiments, the fusion protein includes a full-length human elafin polypeptide sequence having the following amino acid sequence:

```
                                                              (SEQ ID NO: 4)
 1  MRASSFLIVV VFLIAGTLVL EAAVTGVPVK GQDTVKGRVP FNGQDPVKGQ VSVKGQDKVK

61  AQEPVKGPVS TKPGSCPIIL IRCAMLNPPN RCLKDTDCPG IKKCCEGSCG MACFVPQ
```

In some embodiments, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 4.

In some embodiments, the fusion protein includes a portion of the full-length human elafin polypeptide sequence, where the portion has the following amino acid sequence:

```
                                                              (SEQ ID NO: 5)
 1  AVTGVPVKGQ DTVKGRVPFN GQDPVKGQVS VKGQDKVKAQ EPVKGPVSTK PGSCPIILIR

61  CAMLNPPNRC LKDTDCPGIK KCCEGSCGMA CFVPQ
```

In some embodiments, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 5.

In some embodiments, the fusion protein includes the WAP domain of the full-length human elafin polypeptide sequence, where the WAP domain has the following amino acid sequence:

```
                                                              (SEQ ID NO: 6)
 1  VSTKPGSCPI ILIRCAMLNP PNRCLKDTDC PGIKKCCEGS CGMACFVPQ
```

In some embodiments, the fusion protein includes a human elafin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 6.

In some embodiments, the Elafin polypeptide sequence is or the amino acid sequence derived from an Elafin polypeptide is derived from, one or more of the human elafin polypeptide sequences shown in GenBank Accession Nos. P19957.3, NP_002629.1, BAA02441.1, EAW75814.1, EAW75813.1, Q8IUB2.1, and/or NP_542181.1.

In some embodiments, the Polypeptide 1 sequence includes an Eppin polypeptide sequence or an amino acid sequence that is derived from Eppin. In some embodiments, the Polypeptide 1 sequence includes a portion of the Eppin protein, such as for example, the WAP domain or a subportion thereof. In a preferred embodiment, the Eppin polypeptide sequence is or an amino acid sequence that is derived from Eppin is derived from, a human Eppin polypeptide sequence.

In some embodiments, the Eppin polypeptide sequence is or the amino acid sequence derived from an Eppin polypeptide is derived from one or more of the human Eppin polypeptide sequences shown in GenBank Accession Nos. O95925.1, NP_065131.1, AAH44829.2, AAH53369.1, AAG00548.1, AAG00547.1, and/or AAG00546.1.

In some embodiments, the fusion proteins contain one or more mutations. For example, the fusion protein contains at least one mutation at a methionine (Met) residue in the non-Fc portion of the fusion protein, for example in the SLPI portion of the fusion protein. In these Met mutations, the Met residue can be substituted with any amino acid. For example, the Met residue can be substituted with an amino acid with a hydrophobic side chain, such as, for example, leucine (Leu, L) or valine (Val, V). Without wishing to be bound by theory, the Met mutation(s) prevent oxidation and subsequent inactivation of the inhibitory activity of the fusion proteins of the invention. In some embodiments, the Met mutation is at position 98 of an SLPI polypeptide, for example, the Met mutation is Met98Leu (M98L) in SEQ ID NO: 8.

In some embodiments, the fusion proteins are modified to increase or otherwise inhibit proteolytic cleavage, for example, by mutating proteolytic cleavage sites. In some embodiments, the proteolytic cleavage site mutation occurs at a residue in the SLPI portion of the fusion protein. For example, the proteolytic cleavage site mutation occurs at a residue in the amino acid sequence of SEQ ID NO: 2 selected from Ser15, Ala16, Glu17, and combinations thereof.

In some embodiments, the second polypeptide (Polypeptide 2) of the WAP domain-containing fusion protein is an Fc polypeptide or derived from an Fc polypeptide. These embodiments are referred to collectively herein as "WAP-Fc fusion proteins." The WAP-Fc fusion proteins described herein include at least a WAP domain-containing polypeptide or an amino acid sequence that is derived from a WAP domain-containing polypeptide and an Fc polypeptide or an amino acid sequence that is derived from an Fc polypeptide.

In some embodiments, the WAP-Fc fusion protein includes a single WAP domain containing polypeptide. In other embodiments, the WAP-Fc fusion proteins include more than one WAP domain containing polypeptide, collectively referred to herein as "WAP$_{(a')}$-Fc fusion protein," where (a') is an integer of at least 2. In some embodiments, WAP domain containing polypeptides in a WAP$_{(a')}$-Fc fusion protein can include the same amino acid sequence. For example, the WAP domain-containing polypeptides of the WAP$_{(a')}$-Fc fusion protein can be derived from a SLPI or an Elafin polypeptide, but not both (e.g., Elafin-Fc-Elafin, or SLPI-Fc-SLPI). In other embodiments of WAP domain containing polypeptides in a WAP$_{(a')}$-Fc fusion protein can include distinct amino acid sequences. For example, the fusion protein incorporates amino acid sequences derived from both SLPI and Elafin (e.g., SLPI-Fc-Elafin, or Elafin-Fc-SLPI).

In some embodiments, the WAP domain-containing polypeptide of the WAP-Fc fusion protein is derived from any one of the amino acid sequences of SEQ ID NOs 1-6. In some embodiments, the WAP domain-containing polypeptide of the WAP-Fc fusion protein has at least 50%, 60%, 65%, 70%, 75%, 80%, 85%, 90%, 91%, 92%, 93%, 94%, 95%, 96%, 97%, 98% or 99% sequence identity to any one of the amino acid sequences having SEQ ID NO. 1, 2, 3, 4, 5 or 6.

In some embodiments, the WAP domain-containing polypeptide sequence of the WAP-Fc fusion protein is or is derived from sequences shown in GenBank Accession Nos. CAA28187.1, NP_003055.1, EAW75869.1, P03973.2, AAH20708.1, CAB64235.1, CAA28188.1, AAD19661.1, BAG35125.1., P19957.3, NP_002629.1, BAA02441.1, EAW75814.1, EAW75813.1, Q8IUB2.1, and/or NP_542181.1., O95925.1, NP_065131.1, AAH44829.2, AAH53369.1, AAG00548.1, AAG00547.1, and/or AAG00546.1.

In some embodiments, the Fc polypeptide of the WAP-Fc fusion protein is a human Fc polypeptide, for example, a human IgG Fc polypeptide sequence or an amino acid sequence that is derived from a human IgG Fc polypeptide sequence. In some embodiments, the Fc polypeptide is a human IgG1 Fc polypeptide or an amino acid sequence that is derived from a human IgG1 Fc polypeptide sequence. In some embodiments, the Fc polypeptide is a human IgG2 Fc polypeptide or an amino acid sequence that is derived from a human IgG2 Fc polypeptide sequence. In some embodiments, the Fc polypeptide is a human IgG3 Fc polypeptide or an amino acid sequence that is derived from a human IgG3 Fc polypeptide sequence. In some embodiments, the Fc polypeptide is a human IgG4 Fc polypeptide or an amino acid sequence that is derived from a human IgG4 Fc polypeptide sequence. In some embodiments, the Fc polypeptide is a human IgM Fc polypeptide or an amino acid sequence that is derived from a human IgM Fc polypeptide sequence.

In some embodiments where the fusion protein of the invention includes an Fc polypeptide, the Fc polypeptide of the fusion protein includes a human IgG1 Fc polypeptide sequence having the following amino acid sequence:

```
                                                            (SEQ ID NO: 7)
  1 APELLGGPSV FLFPPKPKDT LMISRTPEVT CVVVDVSHED PEVKFNWYVD GVEVHNAKTK

61 PREEQYNSTY RVVSVLTVLH QDWLNGKEYK CKVSNKALPA PIEKTISKAK GQPREPQVYT

121 LPPSRDELTK NQVSLTCLVK GFYPSDIAVE WESNGQPENN YKTTPPVLDS DGSFFLYSKL

181 TVDKSRWQQG NVFSCSVMHE ALHNHYTQKS LSLSPGK
```

In some embodiments, where the fusion protein of the invention includes an Fc polypeptide, the Fc polypeptide of the fusion protein includes a human IgG1 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 7.

In some embodiments where the fusion protein of the invention includes an Fc polypeptide, the Fc polypeptide of the fusion protein includes a human IgG2 Fc polypeptide sequence having the following amino acid sequence:

```
                                                            (SEQ ID NO: 8)
  1 APPVAGPSVF LFPPKPKDTL MISRTPEVTC VVVDVSHEDP EVQFNWYVDG VEVHNAKTKP

61 REEQFNSTFR VVSVLTVVHQ DWLNGKEYKC KVSNKGLPAP IEKTISKTKG QPREPQVYTL

121 PPSREEMTKN QVSLTCLVKG FYPSDIAVEW ESNGQPENNY KTTPPMLDSD GSFFLYSKLT

181 VDKSRWQQGN VFSCSVMHEA LHNHYTQKSL SLSPGK
```

In some embodiments where the fusion protein of the invention includes an Fc polypeptide, the Fc polypeptide of the fusion protein includes a human IgG2 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 8.

In some embodiments where the fusion protein of the invention includes an Fc polypeptide, the Fc polypeptide of fusion protein includes a human IgG3 Fc polypeptide sequence having the following amino acid sequence:

```
                                                            (SEQ ID NO: 9)
  1 APELLGGPSV FLFPPKPKDT LMISRTPEVT CVVVDVSHED PEVQFKWYVD GVEVHNAKTK

61 PREEQYNSTF RVVSVLTVLH QDWLNGKEYK CKVSNKALPA PIEKTISKTK GQPREPQVYT

121 LPPSREEMTK NQVSLTCLVK GFYPSDIAVE WESSGQPENN YNTTPPMLDS DGSFFLYSKL

181 TVDKSRWQQG NIFSCSVMHE ALHNRFTQKS LSLSPGK
```

In some embodiments where the fusion protein of the invention includes an Fc polypeptide, the Fc polypeptide of the fusion protein includes a human IgG3 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 9.

In some embodiments where the fusion protein of the invention includes an Fc polypeptide, the Fc polypeptide of the fusion protein includes a human IgG4 Fc polypeptide sequence having the following amino acid sequence:

```
                                                       (SEQ ID NO: 10)
  1 APEFLGGPSV FLFPPKPKDT LMISRTPEVT CVVVDVSQED PEVQFNWYVD GVEVHNAKTK

61 PREEQFNSTY RVVSVLTVLH QDWLNGKEYK CKVSNKGLPS SIEKTISKAK GQPREPQVYT

121 LPPSQEEMTK NQVSLTCLVK GFYPDIAVEW ESNGQPENNY KTTPPVLDSD GSFFLYSRLT

181 VDKSRWQEGN VFSCSVMHEA LHNHYTQKSL SLSLGK
```

In some embodiments where the fusion protein of the invention includes an Fc polypeptide, the Fc polypeptide of the fusion protein includes a human IgG4 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 10.

In some embodiments where the fusion protein of the invention includes an Fc polypeptide, the Fc polypeptide of the fusion protein includes a human IgM Fc polypeptide sequence having the following amino acid sequence:

```
                                                       (SEQ ID NO: 11)
  1 IAELPPKVSV FVPPRDGFFG NPRKSKLICQ ATGFSPRQIQ VSWLREGKQV GSGVTTDQVQ

61 AEAKESGPTT YKVTSTLTIK ESDWLGQSMF TCRVDHRGLT FQQNASSMCV PDQDTAIRVF

121 AIPPSFASIF LTKSTKLTCL VTDLTTYDSV TISWTRQNGE AVKTHTNISE SHPNATFSAV

181 GEASICEDDW NSGERFTCTV THTDLPSPLK QTISRPKG
```

In some embodiments, where the fusion protein of the invention includes an Fc polypeptide, the Fc polypeptide of the fusion protein includes a human IgM Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 11.

In some embodiments of the fusion proteins provided herein, the second polypeptide (Polypeptide 2) of the WAP domain containing fusion protein is a cytokine targeting polypeptide, or derived from a cytokine targeting polypeptide. These embodiments are referred to collectively herein as "WAP-cytokine targeting polypeptide fusion proteins." The WAP-cytokine targeting polypeptide fusion proteins described herein include at least a WAP domain containing polypeptide or an amino acid sequence that is derived from a WAP domain containing polypeptide and a cytokine targeting polypeptide, or derivation thereof. In some embodiments, the WAP-cytokine targeting polypeptide fusion protein includes a single WAP domain containing polypeptide. In other embodiments, the WAP-cytokine targeting polypeptide fusion protein includes more than one WAP domain containing polypeptide, and these embodiments are collectively referred to herein as "WAP$_{(a')}$-cytokine targeting polypeptide fusion proteins," wherein (a') is an integer of at least 2. In some embodiments, each WAP domain containing polypeptide in a WAP$_{(a')}$-cytokine targeting polypeptide fusion protein can include the same amino acid sequence. In other embodiments, each WAP domain containing polypeptide of a WAP$_{(a')}$-cytokine targeting polypeptide fusion protein can include distinct amino acid sequences.

In some embodiments, the WAP domain-containing polypeptide of the WAP-cytokine targeting polypeptide fusion protein is derived from any one of the amino acid sequences of SEQ ID NOs 1-6. In some embodiments, the WAP domain-containing polypeptide of the WAP-cytokine targeting polypeptide fusion protein has at least 50%, 60%, 65%, 70%, 75%, 80%, 85%, 90%, 91%, 92%, 93%, 94%, 95%, 96%, 97%, 98% or 99% sequence identity to any one of the amino acid sequences having SEQ ID NO. 1, 2, 3, 4, 5 or 6.

In some embodiments, the WAP domain-containing polypeptide sequence of the WAP-cytokine targeting polypeptide fusion protein is or is derived from sequences shown in GenBank Accession Nos. CAA28187.1, NP_003055.1, EAW75869.1, P03973.2, AAH20708.1, CAB64235.1, CAA28188.1, AAD19661.1, BAG35125.1., P19957.3, NP_002629.1, BAA02441.1, EAW75814.1, EAW75813.1, Q8IUB2.1, and/or NP_542181.1., O95925.1, NP_065131.1, AAH44829.2, AAH53369.1, AAG00548.1, AAG00547.1, and/or AAG00546.1.

In some embodiments, the cytokine targeting polypeptide of the WAP-cytokine targeting polypeptide fusion protein is a cytokine receptor or derived from a cytokine receptor. In a preferred embodiment, the cytokine targeting polypeptide is or an amino acid sequence that is derived from the cytokine receptor is derived from a human cytokine receptor sequence. In other embodiments, the cytokine targeting polypeptide is an antibody or antibody fragment, for example an anti-cytokine antibody or anti-cytokine antibody fragment. The term antibody fragment includes single chain, Fab fragment, a F(ab')$_2$ fragment, a scFv, a scAb, a dAb, a single domain heavy chain antibody, and a single domain light chain antibody. In a preferred embodiment, the cytokine targeting polypeptide is or an amino acid sequence that is derived from the antibody or antibody fragment is derived from a chimeric, humanized, or fully human antibody sequence. In other embodiments, the cytokine targeting polypeptide binds a cytokine receptor and prevents binding of a cytokine to the receptor.

The WAP-cytokine targeting polypeptide fusion protein can incorporate a portion of a WAP-Fc fusion protein. For example, an antibody contains an Fc polypeptide. Therefore, in some embodiments, where the cytokine targeting polypeptide is a cytokine-targeting antibody, the WAP-cytokine targeting polypeptide fusion protein will incorporate a portion of the WAP-Fc fusion protein. Furthermore, most receptor fusion proteins that are of therapeutic utility, are Fc fusion proteins. Thus, in some embodiments, wherein the WAP-cytokine targeting polypeptide fusion protein is a WAP-cytokine receptor fusion protein, the WAP-cytokine targeting polypeptide fusion protein may incorporate an Fc polypeptide in addition to the WAP domain-containing polypeptide portion and the cytokine receptor portion.

In some embodiments, where the WAP-cytokine targeting polypeptide fusion protein includes an Fc polypeptide sequence, the Fc polypeptide sequence is derived from any one of the amino acid sequences having the SEQ ID NO. 7, 8, 9, 10, or 11. In some embodiments, where the WAP-cytokine targeting fusion protein includes an Fc polypeptide sequence, the Fc polypeptide sequence has at least 50%, 60%, 65%, 70%, 75%, 80%, 85%, 90%, 91%, 92%, 93%, 94%, 95%, 96%, 97%, 98% or 99% sequence identity to the amino acid sequence of any one of the sequences having the SEQ ID NO. 7, 8, 9, 10, or 11.

In some embodiments, the WAP domain containing polypeptide and the cytokine targeting polypeptide are operably linked via a linker region, for example, a glycine-serine linker or glycine-serine based linker. In some embodiments, the WAP domain containing polypeptide and the cytokine targeting polypeptide are operably linked via a hinge region. In some embodiments, the WAP domain containing polypeptide and the cytokine targeting polypeptide are operably linked via a linker region and a hinge region. In other embodiments, the serpin polypeptide and the cytokine targeting polypeptide are directly attached.

In some embodiments of the fusion proteins provided herein, the second polypeptide (Polypeptide 2) of the WAP domain containing fusion protein is a serpin polypeptide, or derived from a serpin polypeptide. These embodiments are referred to collectively herein as "WAP-serpin fusion proteins." The WAP-serpin fusion proteins described herein include at least a WAP domain containing polypeptide or an amino acid sequence that is derived from a WAP domain containing polypeptide, and a serpin polypeptide or an amino acid sequence that is derived from a serpin polypeptide.

In some embodiments, the WAP domain-containing polypeptide of the WAP-serpin fusion protein is derived from any one of the amino acid sequences of SEQ ID NOs 1-6. In some embodiments, the WAP domain-containing polypeptide of the WAP-serpin fusion protein has at least 50%, 60%, 65%, 70%, 75%, 80%, 85%, 90%, 91%, 92%, 93%, 94%, 95%, 96%, 97%, 98% or 99% sequence identity to any one of the amino acid sequences having SEQ ID NO. 1, 2, 3, 4, 5 or 6.

In some embodiments, the WAP domain-containing polypeptide sequence of the WAP-serpin fusion protein is or is derived from sequences shown in GenBank Accession Nos. CAA28187.1, NP_003055.1, EAW75869.1, P03973.2, AAH20708.1, CAB64235.1, CAA28188.1, AAD19661.1, BAG35125.1., P19957.3, NP_002629.1, BAA02441.1, EAW75814.1, EAW75813.1, Q8IUB2.1, and/or NP_542181.1., O95925.1, NP_065131.1, AAH44829.2, AAH53369.1, AAG00548.1, AAG00547.1, and/or AAG00546.1.

The WAP-serpin fusion proteins described herein include a WAP domain-containing polypeptide and a serpin polypeptide or an amino acid sequence that is derived from a serpin polypeptide. Serpins are a group of proteins with similar structures that were first identified as a set of proteins able to inhibit proteases. Serpin proteins suitable for use in the fusion proteins provided herein include, by way of non-limiting example, alpha-1 antitrypsin (AAT), antitrypsin-related protein (SERPINA2), alpha 1-antichymotrypsin (SERPINA3), kallistatin (SERPINA4), monocyte neutrophil elastase inhibitor (SERPINB1), PI-6 (SERPINB6), antithrombin (SERPINC1), plasminogen activator inhibitor 1 (SERPINE1), alpha 2-antiplasmin (SERPINF2), complement 1-inhibitor (SERPING1), and neuroserpin (SERPINI1).

In some embodiments, the serpin polypeptide sequence comprises an alpha-1 antitrypsin (AAT) polypeptide sequence or an amino acid sequence that is derived from AAT. In some embodiments, the serpin polypeptide sequence comprises a portion of the AAT protein. In some embodiments, the serpin polypeptide sequence comprises at least the reactive site loop portion of the AAT protein. In some embodiments where the fusion protein of the invention includes a serpin polypeptide, the serpin polypeptide of the fusion protein includes the reactive site loop portion of the AAT protein or includes at least the amino acid sequence GTEAAGAMFLEAIPMSIPPEVKFNK (SEQ ID NO: 12). In a preferred embodiment, the AAT polypeptide sequence is or an amino acid sequence that is derived from AAT is derived from a human AAT polypeptide sequence. In some embodiments where the fusion protein of the invention includes a serpin polypeptide, the serpin polypeptide of the fusion protein includes a modified variant of the reactive site loop portion of the AAT protein or includes at least the amino acid sequence GTEAAGAEFLEAIPLSIPPEVKFNK (SEQ ID NO: 38).

In some embodiments of the WAP-serpin fusion proteins, the serpin polypeptide includes a full-length human AAT polypeptide sequence having the following amino acid sequence:

(SEQ ID NO: 13)

```
  1 EDPQGDAAQK TDTSHHDQDH PTFNKITPNL AEFAFSLYRQ LAHQSNSTNI FFSPVSIATA

61 FAMLSLGTKA DTHDEILEGL NFNLTEIPEA QIHEGFQELL RTLNQPDSQL QLTTGNGLFL

121 SEGLKLVDKF LEDVKKLYHS EAFTVNFGDT EEAKKQINDY VEKGTQGKIV DLVKELDRDT

181 VFALVNYIFF KGKWERPFEV KDTEEEDFHV DQVTTVKVPM MKRLGMFNIQ HCKKLSSWVL

241 LMKYLGNATA IFFLPDEGKL QHLENELTHD IITKFLENED RRSASLHLPK LSITGTYDLK

301 SVLGQLGITK VFSNGADLSG VTEEAPLKLS KAVHKAVLTI DEKGTEAAGA MFLEAIPMSI

361 PPEVKFNKPF VFLMIEQNTK SPLFMGKVVN PTQK
```

In some embodiments of the WAP-serpin fusion proteins, the serpin polypeptide includes a human AAT polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 13.

In some embodiments of the WAP-serpin fusion proteins, the serpin polypeptide includes the AAT polypeptide sequence or the amino acid sequence derived from an AAT polypeptide or is derived from one or more of the human AAT polypeptide sequences shown in GenBank Accession Nos. AAB59495.1, CAJ15161.1, P01009.3, AAB59375.1, AAA51546.1, CAA25838.1, NP_001002235.1, CAA34982.1, NP_001002236.1, NP_000286.3, NP_001121179.1, NP_001121178.1, NP_001121177.1, NP_001121176.16, NP_001121175.1, NP_001121174.1, NP_001121172.

In some embodiments, the WAP-serpin domain fusion protein can also include an Fc polypeptide or an amino acid sequence that is derived from an Fc polypeptide. These embodiments are referred to collectively herein as "WAP-Fc-serpin fusion proteins." In these embodiments, no particular order is to be construed by this terminology. For example, the order of the fusion protein can be WAP-Fc-serpin, serpin-WAP-Fc, or any variation or combination thereof. The WAP-Fc-serpin fusion proteins described herein include at least a WAP domain-containing polypeptide or an amino acid sequence that is derived from a WAP domain-containing polypeptide, a serpin polypeptide or an amino acid sequence that is derived from a serpin polypeptide, and an Fc polypeptide or an amino acid sequence that is derived from an Fc polypeptide.

In some embodiments, where the WAP-serpin polypeptide fusion protein includes an Fc polypeptide sequence, the Fc polypeptide sequence is derived from any one of the amino acid sequences having the SEQ ID NO. 7, 8, 9, 10, or 11. In some embodiments, where the WAP-serpin fusion protein includes an Fc polypeptide sequence, the Fc polypeptide sequence has at least 50%, 60%, 65%, 70%, 75%, 80%, 85%, 90%, 91%, 92%, 93%, 94%, 95%, 96%, 97%, 98% or 99% sequence identity to the amino acid sequence of any one of the sequences having the SEQ ID NO. 7, 8, 9, 10, or 11.

In some embodiments, the WAP-serpin domain fusion protein can also include an albumin polypeptide or an amino acid sequence that is derived from an albumin polypeptide. These embodiments are referred to collectively herein as "WAP-albumin-serpin fusion proteins." In these embodiments, no particular order is to be construed by this terminology. For example, the order of the fusion protein can be WAP-albumin-serpin, serpin-albumin-WAP, or any variation combination thereof. The WAP-albumin-serpin fusion proteins described herein include at least a WAP domain-containing polypeptide or an amino acid sequence that is derived from a WAP domain-containing polypeptide, a serpin polypeptide or an amino acid sequence that is derived from a serpin, and an albumin polypeptide or an amino acid sequence that is derived from an albumin polypeptide.

In some embodiments, where the WAP-serpin domain fusion protein includes an albumin polypeptide sequence, the albumin polypeptide sequence is derived from any one of the amino acid sequences of SEQ ID NO. 14-15, described herein. In other embodiments, where the serpin-WAP domain fusion protein includes an albumin polypeptide sequence, the albumin polypeptide sequence has at least 50%, 60%, 65%, 70%, 75%, 80%, 85%, 90%, 91%, 92%, 93%, 94%, 95%, 96%, 97%, 98% or 99% sequence identity to any one of the amino acid sequences having SEQ ID NO. 14 or 15.

In some embodiments of the fusion protein provided herein, the second polypeptide (Polypeptide 2) of the WAP domain containing fusion protein is an albumin polypeptide or is derived from an albumin polypeptide. These embodiments are referred to collectively herein as "WAP-albumin fusion proteins." The WAP-albumin fusion proteins described herein include at least a WAP domain containing polypeptide or an amino acid sequence that is derived from a WAP domain containing polypeptide and an albumin polypeptide or an amino acid sequence that is derived from an albumin polypeptide. In addition this invention relates to WAP domain containing polypeptide albumin binding polypeptide fusion proteins, wherein the albumin is operably linked to the WAP domain containing polypeptide via an intermediate binding molecule. Herein, the WAP domain containing polypeptide is non-covalently or covalently bound to human serum albumin.

In some embodiments, the WAP domain-containing polypeptide of the WAP-albumin fusion protein is derived from any one of the amino acid sequences of SEQ ID NOs 1-6. In some embodiments, the WAP domain-containing polypeptide of the WAP-albumin fusion protein has at least 50%, 60%, 65%, 70%, 75%, 80%, 85%, 90%, 91%, 92%, 93%, 94%, 95%, 96%, 97%, 98% or 99% sequence identity to any one of the amino acid sequences having SEQ ID NO. 1, 2, 3, 4, 5 or 6.

In some embodiments, the WAP domain-containing polypeptide sequence of the WAP-albumin fusion protein is or is derived from sequences shown in GenBank Accession Nos. CAA28187.1, NP_003055.1, EAW75869.1, P03973.2, AAH20708.1, CAB64235.1, CAA28188.1, AAD19661.1, BAG35125.1., P19957.3, NP_002629.1, BAA02441.1, EAW75814.1, EAW75813.1, Q8IUB2.1, and/or NP_542181.1., O95925.1, NP_065131.1, AAH44829.2, AAH53369.1, AAG00548.1, AAG00547.1, and/or AAG00546.1.

In some embodiments where the fusion protein of the invention includes an albumin polypeptide sequence, the albumin polypeptide sequence of the fusion protein is a human serum albumin (HSA) polypeptide or an amino acid sequence derived from HSA. In some embodiments where the fusion protein of the invention includes an albumin polypeptide sequence, the albumin polypeptide sequence of the fusion protein, the fusion protein includes a HSA polypeptide sequence having the following amino acid sequence:

```
                                         (SEQ ID NO: 14)
DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK
```

-continued
EFNAETFTFHADICTLSEKERQIKKQTALVELVKHKPKATKEQLKAVMDD

FAAFVEKCCKADDKETCFAEEGKKLVAASQAALGL

In some embodiments where the fusion protein of the invention includes an albumin polypeptide sequence, the albumin polypeptide sequence of the fusion protein includes a human serum albumin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 14.

In some embodiments of the WAP-albumin fusion proteins, the albumin polypeptide sequence includes a domain 3 of human serum albumin polypeptide sequence having the following amino acid sequence:

(SEQ ID NO: 15)
EEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESL

VNRRPCFSALEVDETYVPKEFNAETFTFHADICTLSEKERQIKKQTALVE

LVKHKPKATKEQLKAVMDDFAAFVEKCCKADDKETCFAEEGKKLVA

In some embodiments of the WAP-albumin fusion proteins, the albumin polypeptide sequence includes a human serum albumin polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 15.

In some embodiment the WAP domain-containing polypeptide is linked to the human serum albumin via an intermediate albumin binding polypeptide. The albumin binding polypeptide can be an antibody or an antibody fragment or derived from an antibody or antibody fragment. In a preferred embodiment, the albumin binding polypeptide is or an amino acid sequence that is derived from the antibody or antibody fragment is derived from a chimeric, humanized, or fully human antibody sequence. The term antibody fragment includes single chain, Fab fragment, a F(ab')$_2$ fragment, a scFv, a scAb, a dAb, a single domain heavy chain antibody, and a single domain light chain antibody. In addition the albumin binding polypeptide can be an albumin binding peptide. Another embodiment of the this invention is a WAP domain-containing polypeptide-albumin binding polypeptide fusion, wherein the albumin binding polypeptide is the domain 3 of streptococcal protein G or a sequence derived from domain 3 of streptococcal protein G. In other embodiments the WAP domain-containing polypeptide and the human serum albumin is directly attached.

In some embodiments, the fusion proteins contain one or more mutations. For example, the fusion protein contains at least one mutation at a methionine (Met) residue in the non-Fc portion of the fusion protein, for example in the SLPI portion of the fusion protein. In these Met mutations, the Met residue can be substituted with any amino acid. For example, the Met residue can be substituted with an amino acid with a hydrophobic side chain, such as, for example, leucine (Leu, L) or valine (Val, V). Without wishing to be bound by theory, the Met mutation(s) prevent oxidation and subsequent inactivation of the inhibitory activity of the fusion proteins of the invention. In some embodiments, the Met mutation is at position 98 of an SLPI polypeptide. For example, a Met mutation that occurs at a residue in the amino acid sequence of SEQ ID NO: 8 is Met98Leu (M98L).

In some embodiments, the fusion proteins are modified to increase or otherwise inhibit proteolytic cleavage, for example, by mutating proteolytic cleavage sites. In some embodiments, the proteolytic cleavage site mutation occurs at a residue in the SLPI portion of the fusion protein. For example, the proteolytic cleavage site mutation occurs at a residue in the amino acid sequence of SEQ ID NO: 2 selected from Ser15, Ala16, Glu17, and combinations thereof.

In some embodiments, the fusion proteins are modified to alter or otherwise modulate an Fc effector function of the fusion protein, while simultaneously retaining binding and inhibitory function as compared to an unaltered fusion protein. Fc effector functions include, by way of non-limiting examples, Fc receptor binding, prevention of proinflammatory mediator release upon binding to the Fc receptor, phagocytosis, modified antibody-dependent cell-mediated cytotoxicity (ADCC), modified complement-dependent cytotoxicity (CDC), modified glycosylation at Asn297 residue (EU index of Kabat numbering, Kabat et at 1991 Sequences of Proteins of Immunological Interest) of the Fc polypeptide. In some embodiments, the fusion proteins are mutated or otherwise modified to influence Fc receptor binding. In some embodiments, the Fc polypeptide is modified to enhance FcRn binding. Examples of Fc polypeptide mutations that enhance binding to FcRn are Met252Tyr, Ser254Thr, Thr256Glu (M252Y, S256T, T256E) (Kabat numbering, Dall'Acqua et at 2006, *J. Biol Chem* Vol 281(33) 23514-23524), or Met428Leu and Asn434Ser (M428L, N434S) (Zalevsky et at 2010 *Nature Biotech*, Vol 28(2) 157-159). (EU index of Kabat et at 1991 *Sequences of Proteins of Immunological Interest*).

The fusion proteins and variants thereof provided herein exhibit inhibitory activity, for example by inhibiting a serine protease such as human neutrophil elastase (NE), a chemotrypsin-fold serine protease that is secreted by neutrophils during an inflammatory response. The fusion proteins provided herein completely or partially reduce or otherwise modulate serine protease expression or activity upon binding to, or otherwise interacting with, a serine protease, e.g., a human serine protease. The reduction or modulation of a biological function of a serine protease is complete or partial upon interaction between the fusion proteins and the human serine protease protein, polypeptide and/or peptide. The fusion proteins are considered to completely inhibit serine protease expression or activity when the level of serine protease expression or activity in the presence of the fusion protein is decreased by at least 95%, e.g., by 96%, 97%, 98%, 99% or 100% as compared to the level of serine protease expression or activity in the absence of interaction, e.g., binding, with a fusion protein described herein. The fusion proteins are considered to partially inhibit serine protease expression or activity when the level of serine protease expression or activity in the presence of the fusion protein is decreased by less than 95%, e.g., 10%, 20%, 25%, 30%, 40%, 50%, 60%, 75%, 80%, 85% or 90% as compared to the level of serine protease expression or activity in the absence of interaction, e.g., binding, with a fusion protein described herein.

The fusion proteins described herein are useful in a variety of therapeutic, diagnostic and prophylactic indications. For example, the fusion proteins are useful in treating a variety of diseases and disorders in a subject. In some embodiments, the fusion proteins described herein, are useful in treating, alleviating a symptom of, ameliorating and/or delaying the progression of a disease or disorder in a subject suffering from or identified as being at risk for a disease or disorder selected from alpha-1-antitrypsin (AAT) deficiency, emphysema, chronic obstructive pulmonary disease (COPD), acute respiratory distress syndrome (ARDS), allergic asthma, cystic fibrosis, cancers of the lung, ischemia-reperfusion injury, including, e.g., ischemia/reperfusion injury following cardiac transplantation, myocardial infarction, arthritis, rheumatoid arthritis, septic arthritis, psoriatic arthritis, ankylosing spondylitis, Crohn's disease, psoriasis, type I and/or type II diabetes, bacterial infections, fungal infections, viral infections, pneumonia, sepsis, graft versus host disease (GVHD), wound healing, Systemic lupus erythematosis, and Multiple sclerosis.

The fusion proteins and variants thereof provided herein exhibit inhibitory activity, for example by inhibiting a serine protease. The fusion proteins provided herein completely or partially reduce or otherwise modulate serine protease expression or activity upon binding to, or otherwise interacting with, a serine protease, e.g., a human serine protease. The reduction or modulation of a biological function of a serine protease is complete or partial upon interaction between the fusion proteins and the human serine protease protein, polypeptide and/or peptide. The fusion proteins are considered to completely inhibit serine protease expression or activity when the level of serine protease expression or activity in the presence of the fusion protein is decreased by at least 95%, e.g., by 96%, 97%, 98%, 99% or 100% as compared to the level of serine protease expression or activity in the absence of interaction, e.g., binding, with a fusion protein described herein. The fusion proteins are considered to partially inhibit serine protease expression or activity when the level of serine protease expression or activity in the presence of the fusion protein is decreased by less than 95%, e.g., 10%, 20%, 25%, 30%, 40%, 50%, 60%, 75%, 80%, 85% or 90% as compared to the level of serine protease expression or activity in the absence of interaction, e.g., binding, with a fusion protein described herein.

Pharmaceutical compositions according to the invention can include a fusion protein of the invention, including modified fusion proteins and other variants, along with a suitable carrier. These pharmaceutical compositions can be included in kits, such as, for example, diagnostic kits.

DETAILED DESCRIPTION OF THE INVENTION

Figure 1A:
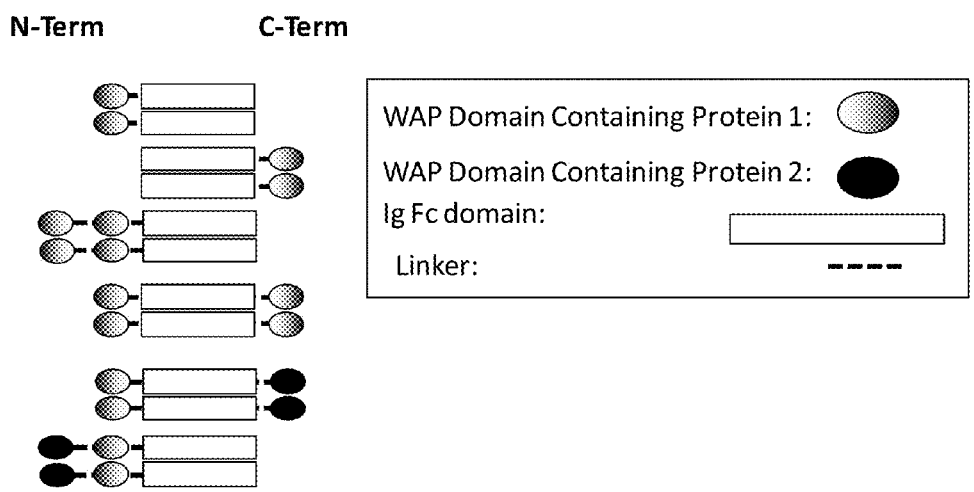
FIG. 1A is a schematic representation of some embodiments of WAP domain containing polypeptide-Fc fusion proteins according to the invention. The WAP domain containing polypeptide can be located at any position within the fusion protein. Variants of these fusion proteins incorporating more than one WAP domain containing polypeptide are also represented.

The whey acidic protein (WAP) domain is motif of approximately 50 amino acids characterized by eight conserved cysteines at defined positions, which form four disulfide bonds (Ranganathan et at 1999 *J. Mol. Graphics Modell.* 17, 134-136). The most well characterized function of the WAP domain is serine protease inhibition. Several WAP domain containing proteins are involved in innate immune protection of multiple epithelia; surfaces (Abe et at 1991 *J. Clin. Invest.* 87(6): 2207-15; Maruyama et at 1994 *J Clin Invest.* 94(1):368-375; Si-Tahar et al 2000 *Gastroenterology* 118(6): 1061-71; King et at 2003 *Reproductive Biology and Endocrinology* 1:116). Some of these proteins have been shown to possess antibacterial activities. Exemplary WAP domain containing proteins are secretory leukocyte protease inhibitor (SLPI), Elafin, and Eppin.

The SLPI and Elafin genes are members of the trappin gene family. Proteins encoded by members of the trappin genes, are characterized by an N-terminal transglutaminase domain substrate and a C-terminal WAP domain (Schalkwijk et at 1999 *Biochem. J.* 340:569-577). SLPI and Elafin are inhibitors of neutrophil serine proteases, yet have slightly distinct target proteases. While SLPI and Elafin are both potent inhibitors of neutrophil elastase, SLPI has also inhibits Cathepsin G but not Proteinase-3, and Elafin inhibits Proteinase-3, but not Cathepsin G (Eisenberg, et al. 1990 *J. Biol. Chem.* 265, 7976-7981, Rao et at 1993 *Am. J. Respir. Cell Mol. Biol.* 8, 612-616, Ying et at 2001 *Am. J. Respir. Cell Mol. Biol.* 24, 83-89). In addition, Elafin inhibits endogenous vascular elastase (EVE), a serine protease produced by diseased vascular tissue (Rabinovitch, M. 1999 *Am. J. Physiol. Lung Cell. Mol. Physiol.* 277, L5-L12; Cowan, et at 1996 *J. Clin. Invest.* 97, 2452-2468).

During inflammation and injury proteases released from neutrophils generally serve to amplify the inflammatory response, through degradation the ECM, generation of chemotactic peptides, MMP activation, and the induction of proteolytic and pro-inflammatory cytokine signaling cascades. SLPI and Elafin represent endogenous regulators of inflammatory signaling that serve to prevent excess inflammation and protect tissues from proteolytic destruction at sites of local inflammation.

In numerous in vitro and in vivo both SLPI and Elafin demonstrated to maintain board anti-inflammatory properties (Doumas et al. 2005. *Infect Immun* 73, 1271-1274; Williams et at 2006 *Clin Sci* (Loud) 110, 21-35, Scott et at 2011 *Biochem. Soc. Trans.* 39(5) 1437-1440; Shaw and Wiedow, 2011 *Biochem. Soc. Trans.* 39, 1450-1454). While many of the anti-inflammatory activities of these proteins are due to protease inhibition, both SLPI and Elafin possess anti-inflammatory capacities that are independent of direct protease inhibition. For instance both bind bacterial LPS and prevent its binding to CD14 and downstream signaling by macrophages (Ding et at 1999 *Infect. Immun.* 67 4485-4489, McMichael et at 2005 *Am. J. Respir. Cell Mol. Biol.* 32 443-452). Studies using human monocytes exposed to LPS, have shown that SLPI inhibited Toll-like receptor and NF-κB activation and subsequent IL-8 and TNFα production signaling in monocytes exposed to LPS (Lentsch et at 1999 *Am. J. Pathol.* 154, 239-247; Taggart et at 2005 *J. Exp. Med.* 202, 1659-1668). SLPI deficient mice are significantly more susceptible to LPS induced endotoxin shock and had higher rates of mortality (Nakamura et al 2003 *J. Exp. Med.* 197, 669-674). Similarly, mice that overexpressed Elafin displayed reduced pro-inflammatory cytokines, including TNFα, MIP-2 and MCP-1, compared to than wild-type mice following LPS challenge (Sallenave et at 2003 *Infect. Immun.* 71, 3766-3774).

In addition to their anti-protease and anti-inflammatory activities, SLPI and Elafin possess anti-infective functionalities against a board class of pathogens, including viruses, bacteria, and fungi. Both SLPI and Elafin have demonstrated antibacterial activity against Gram-positive and Gram-negative species. SLPI has been found to be effective against pathogenic species common in the upper airways such as *Pseudomonas aeruginosa* and *Staphylococcus aureus*, in addition to *Staphylococcus epidermidis* and *Escherichia coli*. While Elafin also exhibits bactericidal activity against *Ps. aeruginosa* and *S. aureus* (Hiemstra, et at 1996 *Infect. Immun.* 64, 4520-4524; Wiedow et at 1998 *Biochem. Biophys. Res. Commun.* 248, 904-909; Simpson et at 2001 *Hum. Gene Ther.* 12, 1395-1406; Meyer-Hoffert et al. 2003 *Exp. Dermatol.* 12, 418-425; Simpson et at 1999 *FEBS Lett.* 452, 309-313). SLPI has been demonstrated to have fungicidal activity against the pathogenic fungi *Aspergillus fumigatus* and *Candida albicans* (Tomee et at 1997 *J. Infect. Dis.* 176:740-747; Chattopadhyay et at 2004 *Infect. Immun.* 72:1956-1963). SLPI also been shown to have anti-HIV activity (McNeely et at 1995 *J. Clin. Investig.* 96:456-464; McNeely et at 1997 *Blood* 90:1141-1149; Hocini et at 2002 *Clin. Diagn. Lab. Immunol.* 7:515-518; Pillay et at 2001 *J. Infect. Dis.* 183:653-656).

Based upon reported studies, it has been suggested that recombinant human SLPI may be useful in the treatment of allergic asthma, emphysema, cystic fibrosis, AAT deficiency, COPD, ARDS, arthritis, bacterial, fungal, and viral infections, spinal cord injuries, wound healing, and ischemia/reperfusion injury following cardiac transplantation (Lucey, E. C., Stone, P. J., Ciccolella, D. E., Breuer, R., Christensen, T. G., Thompson, R. C., and Snider, G. L. (1990). Recombinant human secretory leukocyte-protease inhibitor: in vitro properties, and amelioration of human neutrophil elastase-induced emphysema and secretory cell metaplasia in the hamster. J Lab Clin Med 115, 224-232; Stolk, J., Rudolphus, A., and Kramps, J. A. (1991). Lipopolysaccharide-induced alveolar wall destruction in the hamster is inhibited by intratracheal treatment with r-secretory leukocyte protease inhibitor Ann N Y Acad Sci 624, 350-352; Stromatt, S. C. (1993). Secretory leukocyte protease inhibitor in cystic fibrosis. Agents Actions Suppl 42, 103-110; Watterberg, K. L., Carmichael, D. F., Gerdes, J. S., Werner, S., Backstrom, C., and Murphy, S. (1994). Secretory leukocyte protease inhibitor and lung inflammation in developing bronchopulmonary dysplasia. J Pediatr 125, 264-269; McNeely, T. B., Dealy, M., Dripps, D. J., Orenstein, J. M., Eisenberg, S. P., and Wahl, S. M. (1995). Secretory leukocyte protease inhibitor: a human saliva protein exhibiting anti-human immunodeficiency virus 1 activity in vitro. J Clin Invest 96, 456-464; Fath, M. A., Wu, X., Hileman, R. E., Linhardt, R. J., Kashem, M. A., Nelson, R. M., Wright, C. D., and Abraham, W. M. (1998). Interaction of secretory leukocyte protease inhibitor with heparin inhibits proteases involved in asthma. J Biol Chem 273, 13563-13569; Jin, F., Nathan, C. F., Radzioch, D., and Ding, A. (1998). Lipopolysaccharide-related stimuli induce expression of the secretory leukocyte protease inhibitor, a macrophage-derived lipopolysaccharide inhibitor. Infect Immun 66, 2447-2452; Song, X., Zeng, L., Jin, W., Thompson, J., Mizel, D. E., Lei, K., Billinghurst, R. C., Poole, A. R., and Wahl, S. M. (1999). Secretory leukocyte protease inhibitor suppresses the inflammation and joint damage of bacterial cell wall-induced arthritis. J Exp Med 190, 535-542; Wright, C. D., Havill, A. M., Middleton, S. C., Kashem, M. A., Lee, P. A., Dripps, D. J., O'Riordan, T. G., Bevilacqua, M. P., and Abraham, W. M. (1999). Secretory leukocyte protease inhibitor prevents allergen-induced pulmonary responses in animal models of asthma. J Pharmacol Exp Ther 289, 1007-1014; Ashcroft, G. S., Lei, K., Jin, W., Longenecker, G., Kulkarni, A. B., Greenwell-Wild, T., Hale-Donze, H., McGrady, G., Song, X. Y., and Wahl, S. M. (2000). Secretory leukocyte protease inhibitor mediates non-redundant functions necessary for normal wound healing. Nat Med 6, 1147-1153; Mulligan, M. S., Lentsch, A. B., Huber-Lang, M., Guo, R. F., Sarma, V., Wright, C. D., Ulich, T. R., and Ward, P. A. (2000). Anti-inflammatory effects of mutant forms of secretory leukocyte protease inhibitor. Am J Pathol 156, 1033-1039; Forteza, R. M., Ahmed, A., Lee, T., and Abraham, W. M. (2001). Secretory leukocyte protease inhibitor, but not alpha-1 protease inhibitor, blocks tryptase-induced bronchoconstriction. Pulm Pharmacol Ther 14, 107-110; Pillay, K., Coutsoudis, A., Agadzi-Naqvi, A. K., Kuhn, L., Coovadia, H. M., and Janoff, E. N. (2001). Secretory leukocyte protease inhibitor in vaginal fluids and perinatal human immunodeficiency virus type 1 transmission. J Infect Dis 183, 653-656; Feuerstein, G. (2006). Inflammation and stroke: therapeutic effects of adenoviral expression of secretory Leukocyte Protease Inhibitor. Front Biosci 11, 1750-1757; Weldon, S., McGarry, N., Taggart, C. C., and McElvaney, N. G. (2007). The role of secretory leucoprotease inhibitor in the resolution of inflammatory responses. Biochem Soc Trans 35, 273-276; Nishimura, J., Saiga, H., Sato, S., Okuyama, M., Kayama, H., Kuwata, H., Matsumoto, S., Nishida, T., Sawa, Y., Akira, S., Yoshikai, Y., Yamamoto, M., and Takeda, K. (2008). Potent antimycobacterial activity of mouse secretory leukocyte protease inhibitor. J Immunol 180, 4032-4039; Schneeberger, S., Hautz, T., Wahl, S. M., Brandacher, G., Sucher, R., Steinmassl, O., Steinmassl, P., Wright, C. D., Obrist, P., Werner, E. R., Mark, W., Troppmair, J., Margreiter, R., and Amberger, A. (2008). The effect of secretory leukocyte protease inhibitor (SLPI) on ischemia/reperfusion injury in cardiac transplantation. Am J Transplant 8, 773-782; Ghasemlou, N., Bouhy, D., Yang, J., Lopez-Vales, R., Haber, M., Thuraisingam, T., He, G., Radzioch, D., Ding, A., and David, S. (2010). Beneficial effects of secretory leukocyte protease inhibitor after spinal cord injury. Brain 133, 126-138; Marino, R., Thuraisingam, T., Camateros, P., Kanagaratham, C., Xu, Y. Z., Henri, J., Yang, J., He, G., Ding, A., and Radzioch, D. (2011). Secretory leukocyte protease inhibitor plays an important role in the regulation of allergic asthma in mice. J Immunol 186, 4433-4442).

Recombinant versions of SLPI and Elafin have be generated the administered to man. In fact recombinant Elafin is currently being evaluated in a human clinical trial to treat the inflammatory component of various types of vascular injuries (ref). The recombinant version of both SLPI and Elafin display very short serum halves (<3 hours, Bergenfeldt et at 1990 *Scand J Clin Lab Invest.* 50(7):729-37, WO/2011/107505). The short half-life represents a major limitation to the therapeutic use of these proteins. Thus effective treatment with these version of the protein would require frequent dosing (multiple doses per day).

The fusion proteins of the present invention were generated to enhance therapeutic potential of SLPI and Elafin. To extend the half-life of recombinant SLPI and Elafin, Fc and albumin fusion proteins were created. While it was known that fusion of Fc domains or albumin to some proteins, protein domains or peptides could extend their half-lives (see e.g., Jazayeri, J. A., and Carroll, G. J. (2008). Fc-based cytokines: prospects for engineering superior therapeutics. BioDrugs 22, 11-26; Huang, C. (2009). Receptor-Fc fusion therapeutics, traps, and MIMETIBODY technology. Curr Opin Biotechnol 20, 692-699; Kontermann, R. E. (2009). Strategies to extend plasma half-lives of recombinant antibodies. BioDrugs 23, 93-109; Schmidt, S. R. (2009). Fusion-proteins as biopharmaceuticals—applications and challenges. Curr Opin Drug Discov Devel 12, 284-295), it was unknown, prior to the studies described herein, whether a Fc domain or albumin fused to SLPI or Elafin, would disable their capacity to inhibit neutrophil elastase or have the desired effect of increasing serum half-life. The studies described herein demonstrate that the fusion proteins of the present invention are capable of potent NE inhibition and display enhanced serum half-lives. These fusions proteins of the present invention provide more effective therapeutics over the previous unmodified versions of SLPI or Elafin.

In some embodiments, the WAP domain fusion proteins include SLPI or Elafin polypeptide sequences fused to a cytokine targeting protein.

In some embodiments, the fusion proteins described herein include at least a WAP domain containing polypeptide or an amino acid sequence that is derived from a WAP domain containing polypeptide and a cytokine targeting polypeptide or an amino acid sequence that is derived from a cytokine targeting polypeptide. For example, the invention provides WAP domain containing polypeptide or a sequence derived from a WAP domain containing polypeptide fused to a human cytokine receptor or derivative thereof. Another embodiment of the invention provides WAP domain containing polypeptide or a sequence derived from a WAP domain containing polypeptide fused to a cytokine targeting antibody, e.g., an anti-cytokine antibody, or a sequence derived from of a cytokine targeting antibody, e.g., an anti-cytokine antibody, or sequence derived from a fragment of cytokine targeting antibody, e.g., a fragment of an anti-cytokine antibody. For example, the invention provides a WAP domain containing polypeptide or a sequence derived from a WAP domain containing polypeptide fused to a cytokine targeting polypeptide in which the cytokine targeting polypeptide binds any of the following human cytokines: TNFα, IgE, IL-12, IL-23, IL-6, IL-1α, IL-1β, IL-17, IL-13, the p40 subunit of IL-12 and IL-23, IL-4, IL-10, IL-2, IL-18, IL-27, or IL-32.

For example, in some embodiments, the cytokine targeting polypeptide targets TNFα and includes any of the following TNFα-targeting polypeptide or sequences derived from the following TNFα-targeting polypeptides: Remicade®, Humira®, Simponi®, Cimiza®, or Enbrel®.

For example, in some embodiments, the cytokine targeting polypeptide targets IgE and includes any of the following IgE-targeting polypeptide or sequences derived from the following IgE-targeting polypeptides: Xolair® or FcεRI.

For example, in some embodiments, the cytokine targeting polypeptide targets the shared p40 subunit of IL-12 and IL-23 and includes the Stelara® polypeptide or sequences derived from the Stelara® polypeptide.

For example, Stelara®, the cytokine targeting polypeptide targets IL-13 and includes the CDP7766 polypeptide or sequences derived from the CDP7766 polypeptide.

The invention provides a WAP domain containing polypeptide or a sequence derived from a WAP domain containing polypeptide fused to a cytokine targeting polypeptide in which the cytokine targeting polypeptide binds any of the following human cytokine receptors of TNFα, IgE, IL-12, IL-23, IL-6, IL-1α, IL-1β, IL-17, IL-13, the p40 subunit of IL-12 and IL-23, IL-4, IL-10, IL-2, IL-18, IL-27, or IL-32, thereby preventing binding between receptor and cytokine.

In some embodiments, the fusion proteins described herein include at least a SLPI polypeptide or an amino acid sequence that is derived from SLPI and a cytokine targeting polypeptide or an amino acid sequence that is derived from a cytokine targeting polypeptide. For example, the invention provides SLPI fused a cytokine targeting polypeptide in which the cytokine targeting polypeptide binds any of the following human cytokines: TNFα, IgE, IL-6, IL-1α, IL-1β, IL-12, IL-17, IL-13, IL-23, the p40 subunit of IL-12 and IL-23, IL-4, IL-10, IL-2, IL-18, IL-27, or IL-32.

In some embodiments, the fusion proteins described herein include at least an Elafin polypeptide or an amino acid sequence that is derived from Elafin and a cytokine targeting polypeptide or an amino acid sequence that is derived from a cytokine targeting polypeptide. For example, the invention provides Elafin fused a cytokine targeting polypeptide in which the cytokine targeting polypeptide binds any of the following human cytokines: TNFα, IgE, IL-6, IL-1α, IL-1β, IL-12, IL-17, IL-13, IL-23, the p40 subunit of IL-12 and IL-23, IL-4, IL-10, IL-2, IL-18, IL-27, or IL-32.

In some embodiments the cytokine targeting polypeptide binds a cytokine receptor and prevents binding between receptor and cytokine. For example, the present invention includes a serpin fused to a cytokine receptor targeting antibody. For example, the invention provides SLPI fused a cytokine targeting polypeptide in which the cytokine targeting polypeptide binds the receptor of any of the following human cytokines: TNFα, IgE, IL-6, IL-1α, IL-1β, IL-12, IL-17, IL-13, IL-23, the p40 subunit of IL-12 and IL-23, IL-4, IL-10, IL-2, IL-18, IL-27, or IL-32. For example, the invention provides Elafin fused a cytokine targeting polypeptide in which the cytokine targeting polypeptide binds the receptor of any of the following human cytokines: TNFα, IgE, IL-6, IL-1α, IL-1β, IL-12, IL-17, IL-13, IL-23, the p40 subunit of IL-12 and IL-23, IL-4, IL-10, IL-2, IL-18, IL-27, or IL-32.

For example, in some embodiments, the cytokine targeting polypeptide targets the IL-6 receptor and includes the Actmera® polypeptide or sequences derived from the Actemra® polypeptide. For example, Actemra® the cytokine targeting polypeptide targets the IL-6 receptor and includes the tocilizumab polypeptide or sequences derived from the tocilizumab polypeptide.

The targeting of inflammatory cytokines and immune-stimulating agents by protein therapeutics has demonstrated clinical success in numerous inflammatory conditions. The most common proteins used as cytokine targeting agents are the soluble cytokine receptors and monoclonal antibodies and fragments thereof. A significant drawback with targeting cytokines is the increased risk of infection in these patients, as evidenced by the TNFα targeting biologics, Remicade®, Humira®, Simponi®, Cimiza®, and Enbrel®, and the IL-12/23 p40 targeting antibody, Stelara®. This is likely to be a common problem of targeting inflammatory cytokines leading to immune suppression in patients. As mentioned above, SLPI and Elafin demonstrate both anti-infective and anti-inflammatory activities. Thus, the WAP domain containing polypeptide-cytokine targeting polypeptide fusion proteins of this invention can dampen aberrant cytokine activities while alleviating the risk of infections.

In some embodiments, the fusion proteins described herein include at least the following components: a WAP domain containing polypeptide or an amino acid sequence that is derived from a WAP domain containing, a serpin polypeptide or an amino acid sequence that is derived from a serpin and an Fc polypeptide or an amino acid sequence that is derived from an Fc polypeptide. For example, the invention provides a WAP domain-containing polypeptide, serpin polypeptide, and human IgG1-Fc, IgG2-Fc, IgG3-Fc, IgG4-Fc or IgM-Fc derivatives operably linked together in any functional combination. In some embodiments, the serpin polypeptide is human AAT or derived from AAT. The WAP-Fc-serpin fusion proteins of the invention are expected to have enhanced anti-protease, anti-infective, and anti-inflammatory properties over fusion proteins composed of only a WAP domain containing polypeptide or a serpin polypeptide.

In some embodiments the fusion proteins described herein include at least a WAP domain containing polypeptide or an amino acid sequence that is derived from a WAP domain containing and a human serum albumin (HSA) polypeptide or an amino acid sequence that is derived from a HSA polypeptide. Further embodiments of invention include WAP domain containing polypeptide-albumin binding polypeptide fusion proteins, wherein the albumin binding polypeptide is responsible for the association of the WAP domain containing polypeptide and HSA. Thereby the invention includes both covalent and non-covalent linkages of the serpin polypeptide and the HSA polypeptide or sequences derived from the WAP domain containing polypeptide or an HSA polypeptide. For example, the invention provides a WAP domain containing polypeptide fused to human HSA, or HSA derivatives, or HSA binding peptide or polypeptides.

In some embodiments, the fusion proteins described herein include at least a SLPI polypeptide or an amino acid sequence that is derived from SLPI and a HSA polypeptide or an amino acid sequence that is derived from a HSA polypeptide. For example, the invention provides SLPI fused to HSA or a fragment derived from HSA, or an albumin binding polypeptide. In some embodiments, the fusion proteins described herein include at least a Elafin polypeptide or an amino acid sequence that is derived from Elafin and a HSA polypeptide or an amino acid sequence that is derived from an HSA polypeptide. For example, the invention provides Elafin fused to HSA or a fragment derived from HSA, or an albumin binding polypeptide.

The fusion proteins and fusion protein derivatives described herein are expected to be useful in treating a variety of indications, including, by way of non-limiting example, alpha-1-antitrypsin (AAT) deficiency, emphysema, chronic obstructive pulmonary disease (COPD), ischemia-reperfusion injury, including, e.g., ischemia/reperfusion injury following cardiac transplantation, arthritis, allergic asthma, acute respiratory distress syndrome (ARDS), cystic fibrosis, type I and/or type II diabetes, deficiency, bacterial, fungal, and viral infections, spinal cord injury, wound healing, graft rejection, graft versus host disease (GVHD), pulmonary arterial hypertension (PAH), chronic thrombo-embolic pulmonary hypertension and ischemia/reperfusion injury following cardiac transplantation.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. The term patient includes human and veterinary subjects.

It will be appreciated that administration of therapeutic entities in accordance with the invention will be administered with suitable carriers, buffers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a fusion protein of the invention, are used to treat or alleviate a symptom associated with a disease or disorder associated with aberrant serine protease activity in a subject. The present invention also provides methods of treating or alleviating a symptom associated with a disease or disorder associated with aberrant serine protease activity in a subject. A therapeutic regimen is carried out by identifying a subject, e.g., a human patient suffering from (or at risk of developing) a disease or disorder associated with aberrant serine protease activity, using standard methods, including any of a variety of clinical and/or laboratory procedures. The term patient includes human and veterinary subjects. The term subject includes humans and other mammals.

Efficaciousness of treatment is determined in association with any known method for diagnosing or treating the particular disease or disorder associated with aberrant serine protease activity. Alleviation of one or more symptoms of the disease or disorder associated with aberrant serine protease activity indicates that the fusion protein confers a clinical benefit.

Methods for the screening of fusion proteins that possess the desired specificity include, but are not limited to, enzyme linked immunosorbent assay (ELISA), enzymatic assays, flow cytometry, and other immunologically mediated techniques known within the art.

The fusion proteins described herein may be used in methods known within the art relating to the localization and/or quantitation of a target such as a serine protease, e.g., for use in measuring levels of these targets within appropriate physiological samples, for use in diagnostic methods, for use in imaging the protein, and the like). The terms "physiological sample" and "biological sample," used interchangeably, herein are intended to include tissues, cells and biological fluids isolated from a subject, as well as tissues, cells and fluids present within a subject. Included within the usage of the terms "physiological sample" and "biological sample", therefore, is blood and a fraction or component of blood including blood serum, blood plasma, or lymph.

In a given embodiment, fusion proteins specific for a given target, or derivative, fragment, analog or homolog thereof, that contain the target-binding domain, are utilized as pharmacologically active compounds (referred to hereinafter as "Therapeutics").

A fusion protein of the invention can be used to isolate a particular target using standard techniques, such as immunoaffinity, chromatography or immunoprecipitation. Detection can be facilitated by coupling (i.e., physically linking) the fusion protein to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

A therapeutically effective amount of a fusion protein of the invention relates generally to the amount needed to achieve a therapeutic objective. As noted above, this may be a binding interaction between the fusion protein and its target that, in certain cases, interferes with the functioning of the target. The amount required to be administered will furthermore depend on the binding affinity of the fusion protein for its specific target, and will also depend on the rate at which an administered fusion protein is depleted from the free volume other subject to which it is administered. Common ranges for therapeutically effective dosing of a fusion protein or fragment thereof invention may be, by way of nonlimiting example, from about 0.1 mg/kg body weight to about 250 mg/kg body weight. Common dosing frequencies may range, for example, from twice daily to once a month.

Where fusion protein fragments are used, the smallest inhibitory fragment that specifically binds to the target is preferred. For example, peptide molecules can be designed that retain the ability to bind the target. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, growth-inhibitory agent, an anti-inflammatory agent or anti-infective agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the fusion protein, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

Pharmaceutical Compositions

The fusion proteins of the invention (also referred to herein as "active compounds"), and derivatives, fragments, analogs and homologs thereof, can be incorporated into pharmaceutical compositions suitable for administration. Such compositions typically comprise the fusion protein and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: SLPI-Fc and Elafin-Fc Fusion Proteins and Variants

Exemplary, but non-limiting examples of SLPI-Fc and Elafin Fc fusion proteins according to the invention include the following sequences, where the SLPI or Elafin polypeptide portion of the fusion protein is shown in bold, the WAP domain is underlined, the IgG-Fc polypeptide portion of the fusion protein is italicized, the Met98Leu (ML) mutation in SLPI is boxed, the Fc mutations Met252Tyr, Ser254Thr, Thr256Glu (YTE) or Met428Leu, Asn434Ser (LS) which enhance FcRn binding are boxed, in bold text, and shaded in grey. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence. For example, the polypeptide components can be directly attached.

An exemplary SLPI-Fc fusion protein is the SLPI-hFc. As shown below, the SLPI polypeptide portion of the fusion protein is shown in bold (SEQ ID NO: 2), the WAP domain is underlined, the hinge region is shown in normal text (SEQ ID NO: 48), and the IgG-Fc polypeptide portion of the fusion protein is italicized (SEQ ID NO: 7).

SLPI-hFc1 (human IgG1 Fc, long Hinge (SEQ ID NO: 48))
(SEQ ID NO: 16)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCMGMCGKS

CVSPVKA**EPKSCDKTHTCPPCP*APELLGGPSVFLFPPKPKDTLMISRTPE*

*VTCVVVDVSHEDPEVKFNWYVDGVEVHNAKTKPREEQYNSTYRVVSVLTV*

*LHQDWLNGKEYKCKVSNKALPAPIEKTISKAKGQPREPQVYTLPPSRDEL*

*TKNQVSLTCLVKGFYPSDIAVEWESNGQPENNYKTTPPVLDSDGSFFLYS*

*KLTVDKSRWQQGNVFSCSVMHEALHNHYTQKSLSLSPGK* (SEQ ID NO: 16)

An exemplary SLPI-Fc fusion protein is the SLPI-hFc2 (human IgG2 Fc, long Hinge). As shown below, the SLPI polypeptide portion of the fusion protein is shown in bold (SEQ ID NO: 2), the WAP domain is underlined, the hinge region is shown in normal text (SEQ ID NO: 49), and the IgG-Fc polypeptide portion of the fusion protein is italicized (SEQ ID NO: 8).

SLPI-hFc2 (human IgG2 Fc, long Hinge (SEQ ID NO: 49))
(SEQ ID NO: 17)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCMGMCGKS

CVSPVKA**ERKCCVECPPCP*APPVAGPSVFLFPPKPKDTLMISRTREVTCV*

*VVDVSHEDPEVQFNWYVDGVEVHNAKTKPREEQFNSTFRVVSVLTVVHQD*

*WLNGKEYKCKVSNKGLPAPIEKTISKTKGQPREPQVYTLPPSREEMTKNQ*

*VSLTCLVKGFYPSDIAVEWESNGQPENNYKTTPPMLDSDGSFFLYSKLTV*

*DKSRWQQGNVFSCSVMHEALHNHYTQKSLSLSPGK* (SEQ ID NO: 17)

An exemplary SLPI-Fc fusion protein is the SLPI-ML-hFc1. As shown below, the SLPI polypeptide portion of the fusion protein is shown in bold (SEQ ID NO: 39), the WAP domain is underlined, the hinge region is shown in normal text (SEQ ID NO: 48), the IgG-Fc polypeptide portion of the fusion protein is italicized (SEQ ID NO: 7), and Met98Leu (ML) mutation in SLPI is boxed.

SLPI-ML-hFc1 (human IgG1 Fc, Met98Leu)
(SEQ ID NO: 18)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCM[L]CGKS

CVSPVKA**EPKSCDKTHTCPPCP*APELLGGPSVFLFPPKPKDTLMISRTPE*

*VTCVVVDVSHEDPEVKFNWYVDGVEVHNAKTKPREEQYNSTYRVVSVLTV*

*LHQDWLNGKEYKCKVSNKALPAPIEKTISKAKGQPREPQVYTLPPSRDEL*

*TKNQVSLTCLVKGFYPSDIAVEWESNGQPENNYKTTPPVLDSDGSFFLYS*

*KLTVDKSRWQQGNVFSCSVMHEALHNHYTQKSLSLSPGK* (SEQ ID NO: 18)

An exemplary SLPI-Fc fusion protein is the SLPI-hFc1-YTE. As shown below, the SLPI polypeptide portion of the fusion protein is shown in bold (SEQ ID NO: 39), the WAP domain is underlined, the hinge region is shown in normal text (SEQ ID NO: 48), the IgG-Fc polypeptide portion of the fusion protein is italicized (SEQ ID NO: 40), and the Fc mutations Met252Tyr, Ser254Thr, Thr256Glu (YTE) are boxed, in bold text, and shaded in grey.

SLPI-hFc1-YTE (human IgG1 Fc, Met252Tyr, Ser254Thr, Thr256Glu)
(SEQ ID NO: 19)

(SEQ ID NO: 19)

SGKSFKAGVCPPKKSAQCLRYKKPECQSDWQCPGKKRCCPDTCGIKCLDPVDTPNP<u>TRRKPGKC</u>

<u>PVTYGQCLMLNPPNFCEMDGQCKRDLKCCMGLCGKSCVSPVKAE</u>PKSCDKTHTCPPC*PAPELLG*

*GPSVFLFPPKPKDTLYITREPEVTCVVVDVSHEDPEVKFNWYVDGVEVHNAKTKPREEQYNSTY*

*RVVSVLTVLHQDWLNGKEYKCKVSNKALPAPIEKTISKAKGQPREPQVYTLPPSRDELTKNQVS*

*LTCLVKGFYPSDIAVEWESNGQPENNYKTTPPVLDSDGSFFLYSKLTVDKSRWQQGNVFSCSVM*

*HEALHNHYTQKSLSLSPGK*

An exemplary SLPI-Fc fusion protein is the SLPI-hFc1-LS. As shown below, the SLPI polypeptide portion of the fusion protein is shown in bold (SEQ ID NO: 39), the WAP domain is underlined, the hinge region is shown in normal text (SEQ ID NO: 48), the IgG-Fc polypeptide portion of the fusion protein is italicized (SEQ ID NO: 41), and Met428Leu, Asn434Ser (LS) which enhance FcRn binding are boxed, in bold text, and shaded in grey.

SLPI-hFc1-LS (human IgG1 Fc, Met428Leu, Asn434Ser)
(SEQ ID NO: 20)

SGKSFKAGVCPPKKSAQCLRYKKPECQSDWQCPGKKRCCPDTCGIKCLDPVDTPNP<u>TRRKPGKC</u>

<u>PVTYGQCLMLNPPNFCEMDGQCKRDLKCCMGLCGKSCVSPVKAE</u>PKSCDKTHTCPPC*PAPELLG*

*GPSVFLFPPKPKDTLMISRTPEVTCVVVDVSHEDPEVKFNWYVDGVEVHNAKTKPREEQYNSTY*

*RVVSVLTVLHQDWLNGKEYKCKVSNKALPAPIEKTISKAKGQPREPQVYTLPPSRDELTKNQVS*

*LTCLVKGFYPSDIAVEWESNGQPENNYKTTPPVLDSDGSFFLYSKLTVDKSRWQQGNVFSCSVL*

*HEALHSHYTQKSLSLSPGK*

An exemplary Elafin-Fc fusion protein is the Elafin-hFc1. As shown below, the Elafin polypeptide portion of the fusion protein is shown in bold (SEQ ID NO: 5), the WAP domain is underlined, the hinge region is shown in normal text (SEQ ID NO: 48), the IgG-Fc polypeptide portion of the fusion protein is italicized (SEQ ID NO: 41), and the Asn434Ser (LS) which enhance FcRn binding are boxed, in bold text, and shaded in grey.

Elafin-hFc1 (human IgG1)
(SEQ ID NO: 21)

AVTGVPVKGQDTVKGRVPFNGQDPVKGQVSVKGQDKVKAQEPVKGPVS<u>TKPGSCPIILIRCAML</u>

<u>NPPNRCLKDTDCPGIKKCCEGSCGMACFVPQ</u>EPKSCDKTHTCPPC*PAPELLGGPSVFLFPPKPK*

*DTLMISRTPEVTCVVVDVSHEDPEVKFNWYVDGVEVHNAKTKPREEQYNSTYRVVSVLTVLHQD*

*WLNGKEYKCKVSNKALPAPIEKTISKAKGQPREPQVYTLPPSRDELTKNQVSLTCLVKGFYPSD*

*IAVEWESNGQPENNYKTTPPVLDSDGSFFLYSKLTVDKSRWQQGNVFSCSVLHEALHSHYTQKS*

*LSLSPGK*

An exemplary SLPI-Fc fusion protein is the SLPI-hFc1-SLPI. As shown below, the SLPI polypeptide portion of the fusion protein is shown in bold (SEQ ID NO: 39), the WAP domain is underlined, the hinge region is shown in normal text (SEQ ID NO: 48), the IgG-Fc polypeptide portion of the fusion protein is italicized (SEQ ID NO: 7), and the ASTGS linker is shown in normal text (SEQ ID NO: 50).

SLPI-hFc1-SLPI (human IgG1)
(SEQ ID NO: 22)

SGKSFKAGVCPPKKSAQCLRYKKPECQSDWQCPGKKRCCPDTCGIKCLDP

VDTPNP<u>TRRKPGKCPVTYGQCLMLNPPNFCEMDGQCKRDLKCCMGLCGKS</u>

-continued

CVSPVKAEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYS

KLTVDKSRWQQGNVFSCSVMHEALHNHYTQKSLSLSPGKASTGSSGKSFK

AGVCPPKKSAQCLRYKKPECQSDWQCPGKKRCCPDTCGIKCLDPVDTPNP

TRRKPGKCPVTYGQCLMLNPPNFCEMDGQCKRDLKCCMGLCGKSCVSPVK

A

An exemplary Elafin-Fc fusion protein is the Elafin-hFc1-Elafin. As shown below, the Elafin polypeptide portion of the fusion protein is shown in bold (SEQ ID NO: 5), the WAP domain is underlined, the hinge region is shown in normal text (SEQ ID NO: 48), the IgG-Fc polypeptide portion of the fusion protein is italicized (SEQ ID NO: 7), and the ASTGS linker is shown in normal text (SEQ ID NO: 50).

Elafin-hFc1-Elafin (human IgG1)
(SEQ ID NO: 23)
AVTGVPVKGQDTVKGRVPFNGQDPVKGQVSVKGQDKVKAQEPVKGPVSTK

PGSCPIILIRCAMLNPPNRCLKDTDCPGIKKCCEGSCGMACFVPQEPKSC

DKIHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGKASTGSAVTGVPVKGQDTVKGRVP

FNGQDPVKGQVSVKGQDKVKAQEPVKGPVSTKPGSCPIILIRCAMLNPPN

RCLKDTDCPGIKKCCEGSCGMACFVPQ

An exemplary Elafin-Fc fusion protein is the Elafin-hFc1-SLPI. As shown below, the SLPI polypeptide (SEQ ID NO: 39) portion of the fusion protein is shown in bold, with the WAP domain underlined, the Elafin (SEQ ID NO: 5) polypeptide portion of the fusion protein is shown in bold and italics, the WAP domain is underlined, the IgG-Fc polypeptide portion of the fusion protein is italicized (SEQ ID NO: 7), the hinge region is shown in normal text (SEQ ID NO: 48), and the ASTGS linker is shown in normal text (SEQ ID NO: 50).

Elafin-hFc1-SLPI (human IgG1)
(SEQ ID NO: 24)
AVTGVPVKGQDTVKGRVPFNGQDPVKGQVSVKGQDKVKAQEPVKGPVSTK

PGSCPIILIRCAMLNPPNRCLKDTDCPGIKKCCEGSCGMACFVPQEPKSCD

KIHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGN

VFSCSVMHEALHNHYTQKSLSLSPGKASTGSSGKSFKAGVCPPKKSAQCL

RYKKPECQSDWQCPGKKRCCPDTCGIKCLDPVDTPNPTRRKPGKCPVTYG

QCLMLNPPNFCEMDGQCKRDLKCCMGLCGKSCVSPVKA

An exemplary SLPI-Fc fusion protein is the SLPI-hFc1-Elafin. As shown below, the SLPI (SEQ ID NO: 39) portion of the fusion protein is shown in bold, with the WAP domain underlined, the Elafin (SEQ ID NO: 5) polypeptide portion of the fusion protein is shown in bold and italics, the WAP domain is underlined, and the IgG-Fc polypeptide portion of the fusion protein is italicized (SEQ ID NO: 7), the hinge region is shown in normal text (SEQ ID NO: 48), and the ASTGS linker is shown in normal text (SEQ ID NO: 50).

SLPI-hFc1-Elafin (human IgG1)
(SEQ ID NO: 25)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCMGLCGKS

CVSPVKAEPKSCDKIHTCPPCPAPELLGGPSVFLFPPKPKDTLMISRTPE

VTCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYS

KLTVDKSRWQQGNVFSCSVMHEALHNHYTQKSLSLSPGKASTGSAVTGVP

VKGQDTVKGRVPFNGQDPVKGQVSVKGQDKVKAQEPVKGPVSTKPGSCPI

ILIRCAMLNPPNRCLKDTDCPGIKKCCEGSCGMACFVPQ

These exemplary SLPI-Fc and Elafin-Fc fusion proteins were made using the following techniques.

Figure 1B:
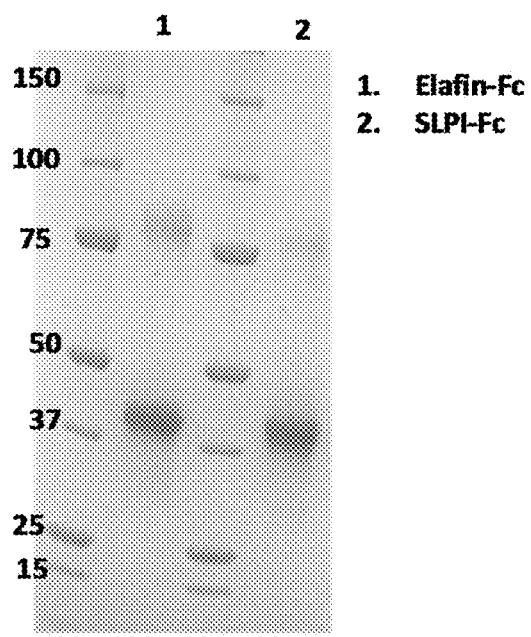
FIG. 1B is a photograph of a SDS-PAGE gel showing Elafin-Fc1 (lane 1, human IgG1 Fc), and SLPI-Fc1 (lane 2, human IgG1 Fc).
Figure 1C:
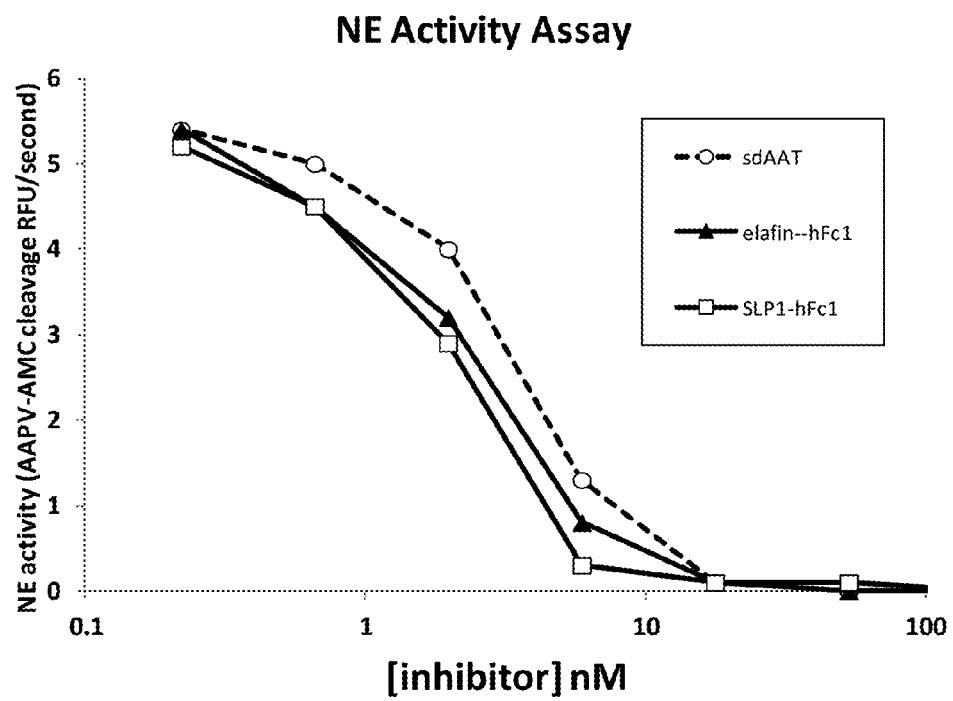
FIG. 1C is a graph showing the inhibition of neutrophil elastase activity by Elafin-Fc and SLPI-Fc fusion proteins.
Figure 1D:
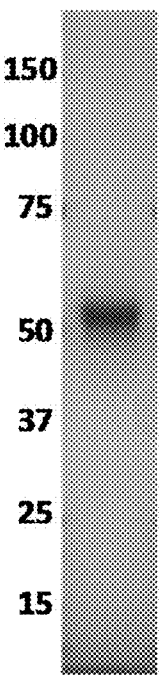
FIG. 1D is a photograph of a SDS-PAGE gel showing the fusion protein consisting Elafin-Fc-SLPI.

The genes encoding human SLPI and Elafin were PCR amplified from human spleen cDNA (Zyagen). Specific point mutations within the gene encoding SLPI, Elafin or the Fc region were generated by overlapping PCR. The SLPI or Elafin encoding gene was cloned in frame with a gene encoding the hinge region, followed by a CH2 domain, and a CH3 domain of human IgG1, IgG2, IgG3, IgG4, or IgM into a mammalian expression vector, containing a mammalian secretion signal sequence up stream of the SLPI or Elafin gene insertion site. In some cases, these vectors were further modified, wherein the gene encoding a linker sequence and either SLPI or Elafin was cloned in frame to the 3' end of the CH3 domain, to generate SLPI-Fc-SLPI, Elafin-Fc-Elafin, SLPI-Fc-Elafin, or Elafin-Fc-SLPI. These expression vectors were transfected into mammalian cells (specifically HEK293 or CHO cells) and grown for several days in 8% $CO_2$ at 37° C. The recombinant SLPI-Fc and Elafin-Fc fusion proteins were purified from the expression cell supernatant by protein A chromatography. FIG. 1B shows a reducing SDS-PAGE gel of the Elafin-Fc (SEQ ID NO:21, lane 1) and SLPI-Fc (SEQ ID NO:16, lane 2) fusion proteins. FIG. 1D shows a reducing SDS-PAGE gel of the Elafin-Fc-SLPI (SEQ ID NO:24). The proteins were visualized by staining with coomassie blue.

Figure 1E:
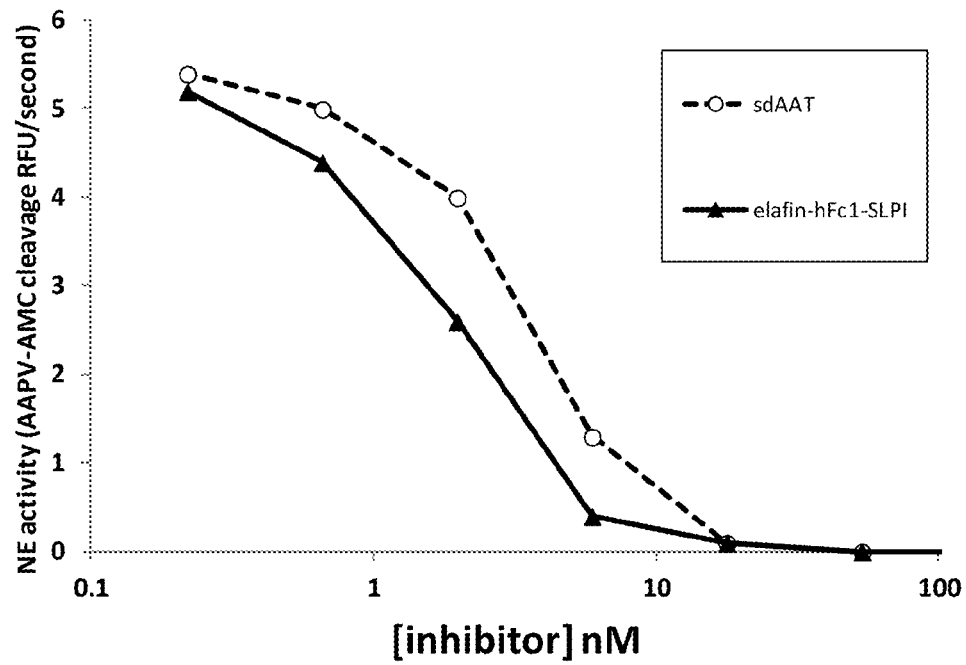
FIG. 1E is a graph showing the inhibition of neutrophil elastase activity by Elafin-Fc-SLPI. Serum derived AAT is shown as a control for NE inhibition.

To monitor human Neutrophil Elastase (NE) activity a fluorescent microplate assay was used. Inhibitory activity was measured by a concomitant decrease in the residual NE activity using the following assay. This assay buffer is composed of 100 mM Tris pH 7.4, 500 mM NaCl, and 0.0005% Triton X-100. Human NE is used at a final concentration of 5 nM (but can also be used from 1-20 nM). The fluorescent peptide substrate AAVP-AMC is used at a final concentration of 100 µM in the assay. The Gemini EM plate reader from Molecular Devices is used to read the assay kinetics using excitation and emission wavelengths of 370 nm and 440 nm respectively, and a cutoff of 420 nm. The assay is read for 10 min at room temperature scanning every 5 to 10 seconds. The Vmax per second corresponds to the residual NE activity, which is plotted for each concentration of inhibitor. The intercept with the x-axis indicates the concentration of inhibitor needed to fully inactivate the starting concentration of NE in the assay. Human serum derived AAT (sdAAT) was used as a positive control for NE inhibition in these assays. The Elafin-Fc and SLPI-Fc fusion proteins display potent inhibition of NE (FIG. 1C). The Elafin-Fc-SLPI fusion protein also was a potent inhibitor of NE (FIG. 1E).

Figure 1F:
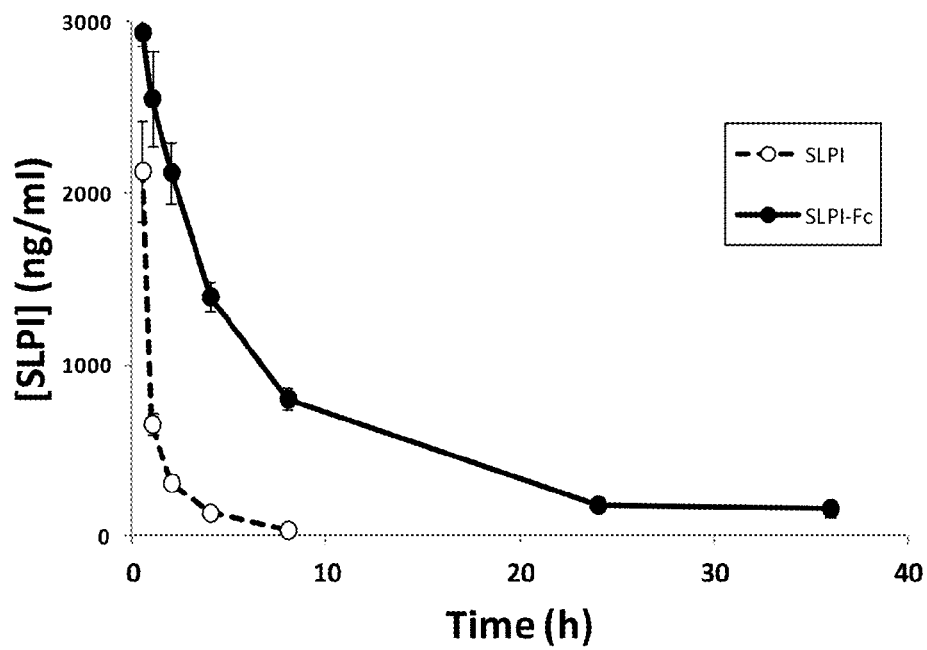
FIG. 1F is a graph depicting the serum concentrations over time of recombinant SLPI compared to SLPI-Fc in rats (3 per test protein) dosed with 10 mg/kg protein. The half-life of SLPI-Fc is substantially longer than that of recombinant SLPI.

Furthermore, the SLPI-Fc fusion protein displayed a longer serum half-life in rats compared to *E. coli* produced unmodified SLPI (FIG. 1F), demonstrating that the fusion proteins of the invention have improved pharmacokinetic properties and are a superior therapeutic format over unmodified versions of SLPI and Elafin, for treating numerous human inflammatory conditions Example 2: SLPI-TNFα Targeting Molecule Fusion Proteins The studies presented herein describe several, non-limiting examples of recombinant SLPI derivatives comprising human SLPI fused to an anti-TNFα antibody or a derivative of a TNFα receptor. These examples are provided below to further illustrate different features of the present invention. The examples also illustrate useful methodology for practicing the invention. These examples do not and are not intended to limit the claimed invention.

The fusion proteins below include cytokine targeting polypeptide sequences that are from or are derived from (i) the anti-TNFα antibody D2E7 (also known as Adalimumab or Humira®), or (ii) the extracellular domain of Type 2 TNFα Receptor (TNFR2-ECD). The SLPI polypeptide portion of the fusion protein is in bold text, the WAP domain is underlined, the antibody constant regions (CH1-hinge-CH2-CH3, or CL) are italicized, and D2E7-VH, D2E7-VK, and TNFR2-ECD are shaded in grey and in bold text. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence. For example, the polypeptide components can be directly attached.

An exemplary SLPI-TNFα Targeting Molecule fusion protein is D2E7-Light Chain-SLPI (G₃S)₂ Linker. As shown below the SLPI polypeptide portion of the fusion protein is in bold text (SEQ ID NO: 2), the WAP domain is underlined, the antibody constant regions (CH1-hinge-CH2-CH3, or CL) are italicized (SEQ ID NO: 43), and D2E7-VK is shaded in grey and in bold text (SEQ ID NO: 42).

D2E7-Light Chain-SLPI (G₃S)₂ Linker
(SEQ ID NO: 26)
DIQMTQSPSSLSASVGDRVTITCRASQGIRNYLAWYQQKPGKAPKLLIYAASTLQSGVPSRFSG

SGSGTDFTLTISSLQPEDVATYYCQRYNRAPYTFGQGTKVEIK*RTVAAPSVFIFPPSDEQLKSG*

*TASVVCLLNNFYPREAKVQWKVDNALQSGNSQESVTEQDSKDSTYSLSSTLTLSKADYEKHKVY*

*ACEVTHQGLSSPVTKSFNRGEC*GGGSGGGSSGKSFKAGVCPPKKSAQCLRYKKPECQSDWQCPG

KKRCCPDTCGIKCLDPVDTPNPTRRKPGKCPVTYGQCLMLNPPNFCEMDGQCKRDLKCCMGMCG

KSCVSPVKA

An exemplary SLPI-TNFα Targeting Molecule fusion protein is D2E7-Light Chain-SLPI ASTGS Linker. As shown below the SLPI polypeptide portion of the fusion protein is in bold text (SEQ ID NO: 2), the WAP domain is underlined, the antibody constant regions (CH1-hinge-CH2-CH3, or CL) are italicized (SEQ ID NO: 43), and D2E7-VK is shaded in grey and in bold text (SEQ ID NO: 42).

D2E7-Light Chain-SLPI ASTGS Linker
(SEQ ID NO: 27)
DIQMTQSPSSLSASVGDRVTITCRASQGIRNYLAWYQQKPGKAPKLLIYAASTLQSGVPSRFSG

SGSGTDFTLTISSLQPEDVATYYCQRYNRAPYTFGQGTKVEIK*RTVAAPSVFIFPPSDEQLKSG*

*TASVVCLLNNFYPREAKVQWKVDNALQSGNSQESVTEQDSKDSTYSLSSTLTLSKADYEKHKVY*

*ACEVTHQGLSSPVTKSFNRGEC*ASTGSSGKSFKAGVCPPKKSAQCLRYKKPECQSDWQCPGKKR

CCPDTCGIKCLDPVDTPNPTRRKPGKCPVTYGQCLMLNPPNFCEMDGQCKRDLKCCMGMCGKSC

VSPVKA

An exemplary SLPI-TNFα Targeting Molecule fusion protein is D2E7-Heavy Chain-SLPI (G₃S)₂ Linker. As shown below the SLPI polypeptide portion of the fusion protein is in bold text (SEQ ID NO: 2), the WAP domain is underlined, the antibody constant regions (CH1-hinge-CH2-CH3, or CL) are italicized (SEQ ID NO: 45), and D2E7-VH is shaded in grey and in bold text (SEQ ID NO: 44).

D2E7-Heavy Chain-SLPI (G₃S)₂ Linker (SEQ ID NO: 28)

EVQLVESGGGLVQPGRSLRLSCAASGFTFDDYAMHWVRQAPGKGLEWVSAITWNSGHIDYADSV

EGRFTISRDNAKNSLYLQMNSLRAEDTAVYYCAKVSYLSTASSLDYWGQGTL*VTVSSASTKGPS*

*VFPLAPSSKSTSGGTAALGCLVKDYFPEPVTVSWNSGALTSGVHTFPAVLQSSGLYSLSSVVTV*

*PSSSLGTQTYICNVNHKPSNTKVDKKVEPKSCDKTHTCPPCPAPELLGGPSVFLFPPKPKDTLM*

*ISRTPEVTCVVVDVSHEDPEVKFNWYVDGVEVHNAKTKPREEQYNSTYRVVSVLTVLHQDWLNG*

*KEYKCKVSNKALPAPIEKTISKAKGQPREPQVYTLPPSRDELTKNQVSLTCLVKGFYPSDIAVE*

*WESNGQPENNYKTTPPVLDSDGSFFLYSKLTVDKSRWQQGNVFSCSVMHEALHNHYTQKSLSLS*

*PGKGGGSGGGS*SGKSFKAGVCPPKKSAQCLRYKKPECQSDWQCPGKKRCCPDTCGIKCLDPVDT

PNP<u>TRRKPGKCPVTYGQCLMLNPPNFCEMDGQCKRDLKCCMGMCGKSCVSPVKA</u>

An exemplary SLPI-TNFα Targeting Molecule fusion protein is D2E7-Heavy Chain-SLPI ASTGS Linker. As shown below the SLPI polypeptide portion of the fusion protein is in bold text (SEQ ID NO: 2), the WAP domain is underlined, the antibody constant regions (CH1-hinge-CH2-CH3, or CL) are italicized (SEQ ID NO: 45), and D2E7-VH is shaded in grey and in bold text (SEQ ID NO: 44).

D2E7-Heavy Chain-SLPI ASTGS Linker (SEQ ID NO: 29)

EVQLVESGGGLVQPGRSLRLSCAASGFTFDDYAMHWVRQAPGKGLEWVSAITWNSGHIDYADSV

EGRFTISRDNAKNSLYLQMNSLRAEDTAVYYCAKVSYLSTASSLDYWGQGTL*VTVSSASTKGPS*

*VFPLAPSSKSTSGGTAALGCLVKDYFPEPVTVSWNSGALTSGVHTFPAVLQSSGLYSLSSVVTV*

*PSSSLGTQTYICNVNHKPSNTKVDKKVEPKSCDKTHTCPPCPAPELLGGPSVFLFPPKPKDTLM*

*ISRTPEVTCVVVDVSHEDPEVKFNWYVDGVEVHNAKTKPREEQYNSTYRVVSVLTVLHQDWLNG*

*KEYKCKVSNKALPAPIEKTISKAKGQPREPQVYTLPPSRDELTKNQVSLTCLVKGFYPSDIAVE*

*WESNGQPENNYKTTPPVLDSDGSFFLYSKLTVDKSRWQQGNVFSCSVMHEALHNHYTQKSLSLS*

*PGK*ASTGSSGKSFKAGVCPPKKSAQCLRYKKPECQSDWQCPGKKRCCPDTCGIKCLDPVDTPNP

<u>TRRKPGKCPVTYGQCLMLNPPNFCEMDGQCKRDLKCCMGMCGKSCVSPVKA</u>

An exemplary SLPI-TNFα Targeting Molecule fusion protein is TNFR2-ECD-Fc1-SLPI(G₃S)₂ Linker. As shown below, the SLPI polypeptide portion of the fusion protein is in bold text, (SEQ ID NO: 2), the WAP domain is underlined, the Fc polypeptide portion is italicized (SEQ ID NO: 47), the TNFR2-ECD is shaded in grey and in bold text (SEQ ID NO: 46), the hinge region is shown in normal text (SEQ ID NO: 48), and the (G3S)₂ linker is shown in normal text (SEQ ID NO: 51).

TNFR2-ECD-Fc1-SLPI(G₃S)₂ Linker (SEQ ID NO: 30)

LPAQVAFTPYAPEPGSTCRLREYYDQTAQMCCSKCSPGQHAKVFCTKTSDTVCDSCEDSTYTQL

WNWVPECLSCGSRCSSDQVETQACTREQNRICTCRPGWYCALSKQEGCRLCAPLRKCRPGFGVA

-continued

RPGTETSDVVCKPCAPGTFSNTTSSTDICRPHQICNVVAIPGNASMDAVCTSTSPTRSMAPGAV

HLPQPVSTRSQHTQPTPEPSTAPSTSFLLPMGPSPPAEGSTGDEPKSCDKTHTCPPCPAPELLG

GPSVFLFPPKPKDTLMISRTPEVTCVVVDVSHEDPQVKFNWYVDGVQVHNAKTKPREQQYNSTY

RVVSVLTVLHQNWLDGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDKSRWQQGNVFSCSVM

HEALHNHYTQKSLSLSPGKGGGSGGGSSGKSFKAGVCPPKKSAQCLRYKKPECQSDWQCPGKKR

CCPDTCGIKCLDPVDTPNPTRRKPGKCPVTYGQCLMLNPPNFCEMDGQCKRDLKCCMGMCGKSC

VSPVKA

An exemplary SLPI-TNFα Targeting Molecule fusion protein is TNFR2-ECD-

Figure 2A:
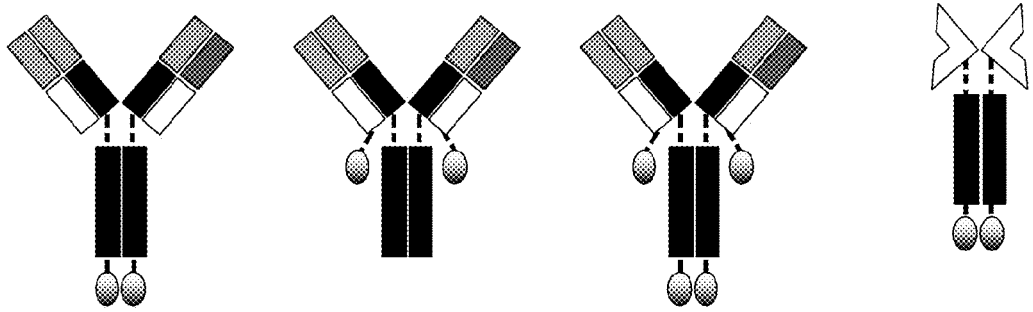
FIG. 2A is a schematic representation of some embodiments of the WAP domain containing polypeptide-cytokine targeting fusion proteins of the invention. The WAP domain containing polypeptide can be fused to either the heavy chain, the light chain, or both of an antibody. WAP domain containing polypeptide-cytokine receptor fusion proteins are also depicted.
Figure 2A:
Figure 2A:
Figure 2A:
Figure 2A:
Figure 2A:
Figure 2A:
Figure 2A:
Figure 2B:
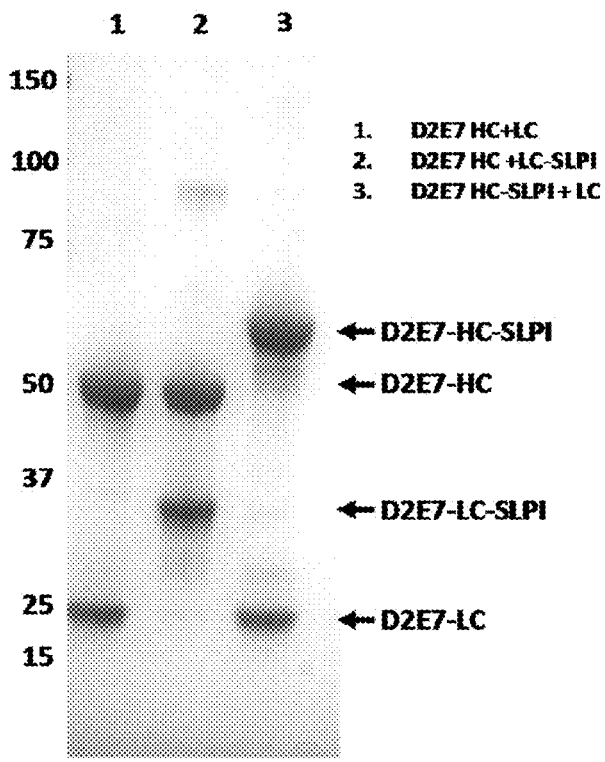
FIG. 2B is a photograph of a SDS-PAGE gel showing the D2E7 antibody (lane 1), the D2E7 antibody with-SLPI fused to heavy chain (lane 2), and the D2E7 antibody with SLPI fused to the light chain (lane 3).

A chromatography. FIG. 2B shows a reducing SDS-PAGE gel of the D2E7 antibody alone (lane 1), the D2E7 antibody with SLPI fused to the light chain (SEQ ID NO: 27 co-transfected with D2E7 heavy chain, lane 2), the D2E7 antibody with SLPI fused to the heavy chain (SEQ ID NO: 29 co-transfected with D2E7 light chain, lane 3). Arrows denote modified (SLPI fused) and unmodified (no SLPI) heavy and light chains. The proteins were visualized by staining with coomassie blue.

Figure 2C:
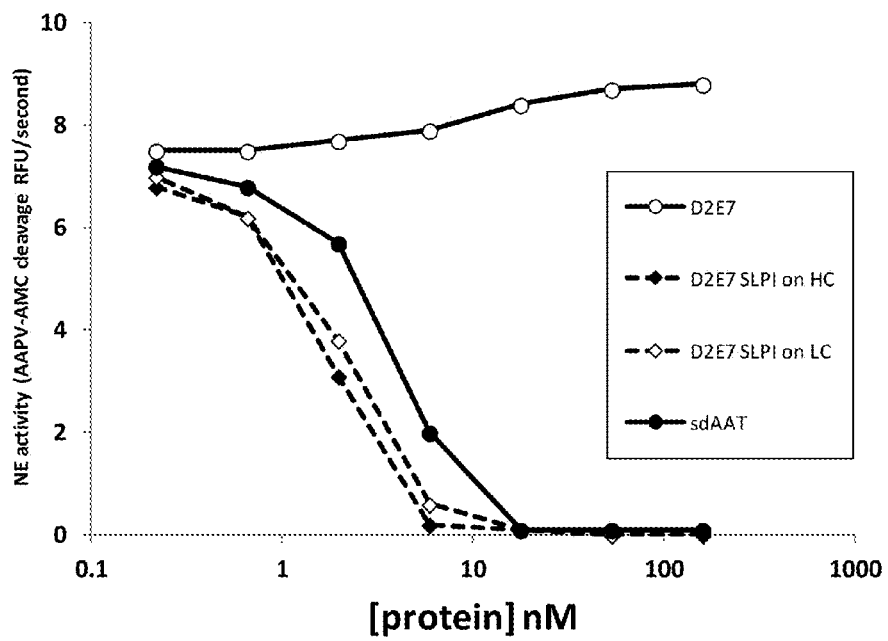
FIG. 2C is a graph showing the inhibition of neutrophil elastase activity by a D2E7 antibody fused to SLPI on either the heavy chain or the light chain. Serum derived AAT is shown and positive control, whereas the D2E7 antibody alone is shown as a negative control for NE inhibition.

The purified SLPI-TNFα targeting molecule fusion proteins were tested for activity by determining their ability to inhibit neutrophil elastase. Human serum derived AAT (sdAAT) was used as a positive control in these assays. (FIG. 2C). Relative to serum derived AAT, the D2E7-antibody-SLPI fusion proteins show similar inhibition of neutrophil elastase, indicating that the inhibitory capacity of SLPI has not been compromised by its fusion to an antibody. The NE inhibition assays were conducted as described above.

Example 3: AAT-Fc-SLPI and AAT-Fc-Elafin

The studies presented herein describe several, non-limiting examples of recombinant AAT derivatives comprising human AAT fused a WAP domain containing protein. These examples are provided below to further illustrate different features of the present invention. The examples also illustrate useful methodology for practicing the invention. The AAT polypeptide portion of the fusion protein is shown in bold text and shaded in grey, the Fc portion is italicized, the SLPI and Elafin portion are in bold text, and the WAP domain containing polypeptide is underlined. While these examples include a hinge sequence and/or a linker sequence, fusion proteins of the invention can be made using any hinge sequence and/or a linker sequence suitable in length and/or flexibility. Alternatively fusion proteins can be made without using a hinge and/or a linker sequence. For example, the polypeptide components can be directly attached.

An exemplary AAT-Fc-SLPI fusion protein is AAT-hFc1-SLPI (human IgG1 Fc). As shown below, the AAT polypeptide portion of the fusion protein is shown in bold text and shaded in grey (SEQ ID NO:13), the Fc portion is italicized (SEQ ID NO: 7), the SLP1 portion is in bold text (SEQ ID NO: 2), the WAP domain containing polypeptide is underlined (SEQ ID NO: 3), the hinge region is shown in normal text (SEQ ID NO: 48), and the ASTGS linker is shown in normal text (SEQ ID NO: 50).

AAT-hFc1-SLPI (human IgG1 Fc)
(SEQ ID NO: 32)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

KFLEDVKKLYHSEAFTVNFGDTEEAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGAMFLEAIPMSIPPEVKFNKPFVFLMIEQNTKSPLF

MGKVVNPTQKEPKSCDKTHTCPPC*PAPELLGGPSVFLFPPKPKDTLMISRTPEVTCVVVDVSHE*

*DPEVKFNWYVDGVEVHNAKTKPREEQYNSTYRVVSVLTVLHQDWLNGKEYKCKVSNKALPAPIE*

*KTISKAKGQPREPQVYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGK**ASTGS**SGKSFKAGV*

CPPKKSAQCLRYKKPECQSDWQCPGKKRCCPDTCGIKCLDPVDTPNPTRRKPGKCPVTYGQCLM

LNPPNFCEMDGQCKRDLKCCMGMCGKSCVSPVKA

An exemplary AAT-Fc-Elafin fusion protein is AAT-hFc1-Elafin. As shown below, the AAT polypeptide portion of the fusion protein is shown in bold text and shaded in grey (SEQ ID NO: 13), the Fc portion is italicized (SEQ ID NO: 7), the Elafin portion is in bold text (SEQ ID NO: 5), the WAP domain containing polypeptide is underlined (SEQ ID NO: 6), the hinge region is shown in normal text (SEQ ID NO: 48), and the ASTGS linker is shown in normal text (SEQ ID NO: 50).

AAT-hFc1-Elafin (human IgG1 Fc)
(SEQ ID NO: 33)

EDPQGDAAQKTDTSHHDQDHPTFNKITPNLAEFAFSLYRQLAHQSNSTNIFFSPVSIATAFAML

SLGTKADTHDEILEGLNFNLTEIPEAQIHEGFQELLRTLNQPDSQLQLTTGNGLFLSEGLKLVD

-continued

KFLEDVKKLYHSEAFTVNFGDTEEAAKKQINDYVEKGTQGKIVDLVKELDRDTVFALVNYIFFKG

KWERPFEVKDTEEEDFHVDQVTTVKVPMMKRLGMFNIQHCKKLSSWVLLMKYLGNATAIFFLPD

EGKLQHLENELTHDIITKFLENEDRRSASLHLPKLSITGTYDLKSVLGQLGITKVFSNGADLSG

VTEEAPLKLSKAVHKAVLTIDEKGTEAAGAMFLEAIPMSIPPEVKFNKPFVFLMIEQNTKSPLF

MGKVVNPTQKEPKSCDKTHTCPPC*PAPELLGGPSVFLFPPKPKDTLMISRTPEVTCVVVDVSHE*

*DPEVKFNWYVDGVEVHNAKTKPREEQYNSTYRVVSVLTVLHQDWLNGKEYKCKVSNKALPAPIE*

*KTISKAKGQPREPQVYTLPPSRDELTKNQVSLTCLVKGFYPSDIAVEWESNGQPENNYKTTPPV*

*LDSDGSFFLYSKLTVDKSRWQQGNVFSCSVMHEALHNHYTQKSLSLSPGKASTGSA*VTGVPVKG

QDTVKGRVPFNGQDPVKGQVSVKGQDKVKAQEPVKGPVSTKPGSCPIILIRCAMLNPPNRCLKD

TDCPGIKKCCEGSCGMACFVPQ

Figure 3A:
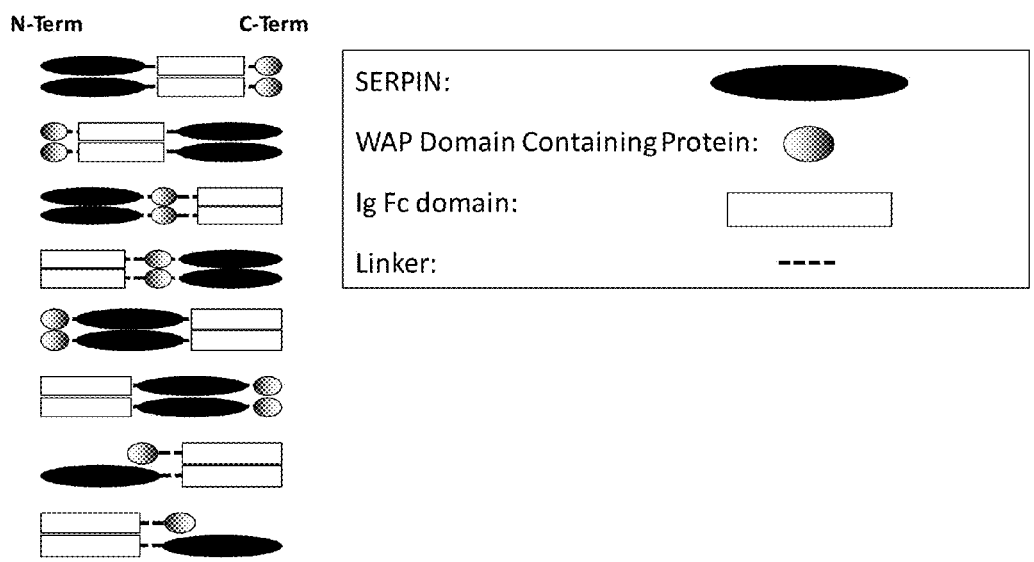
FIG. 3A is a schematic representation of some embodiments of the serpin-Fc-WAP fusion proteins.
Figure 3B:
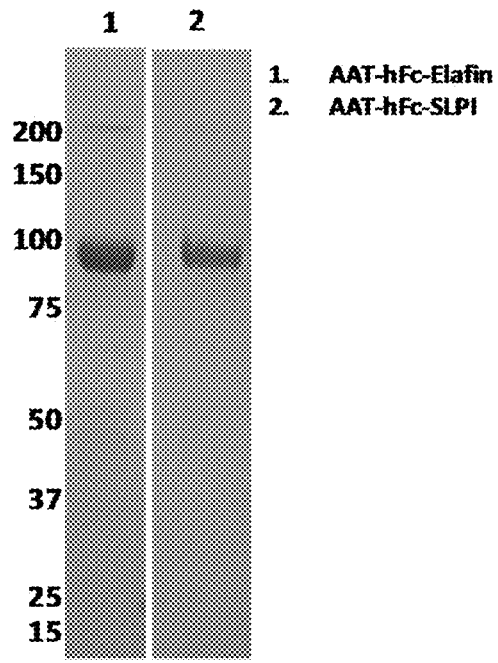
FIG. 3B is a photograph of a SDS-PAGE gel showing AAT-Fc-Elafin (lane 1) and AAT-Fc-SLPI (lane 2).

The genes encoding the SLPI and Elafin were PCR amplified from human spleen cDNA (Zyagen). These genes and flanking linker sequences were cloned in frame into mammalian expression vectors containing the genes encoding AAT and an Ig Fc region, wherein a mammalian secretion precedes the AAT gene. These expression vectors were transfected into mammalian cells (specifically HEK293 or CHO cells) and grown for several days in 8% CO₂ at 37° C. The recombinant AAT-Fc-WAP domain fusion proteins were purified from the expression cell supernatant by protein A chromatography. A near neutral pH buffer was used (Gentle Ag/Ab Elution Buffer, Thermo Scientific) to elute the AAT-Fc-WAP domain fusion protein from the protein A resin. FIG. 3B shows a reducing SDS-PAGE gel of the purified fusion proteins: AAT-Fc-Elafin (SEQ ID NO: 33, lane 1) and AAT-Fc-SLPI (SEQ ID NO: 32, lane 2).

Figure 3C:
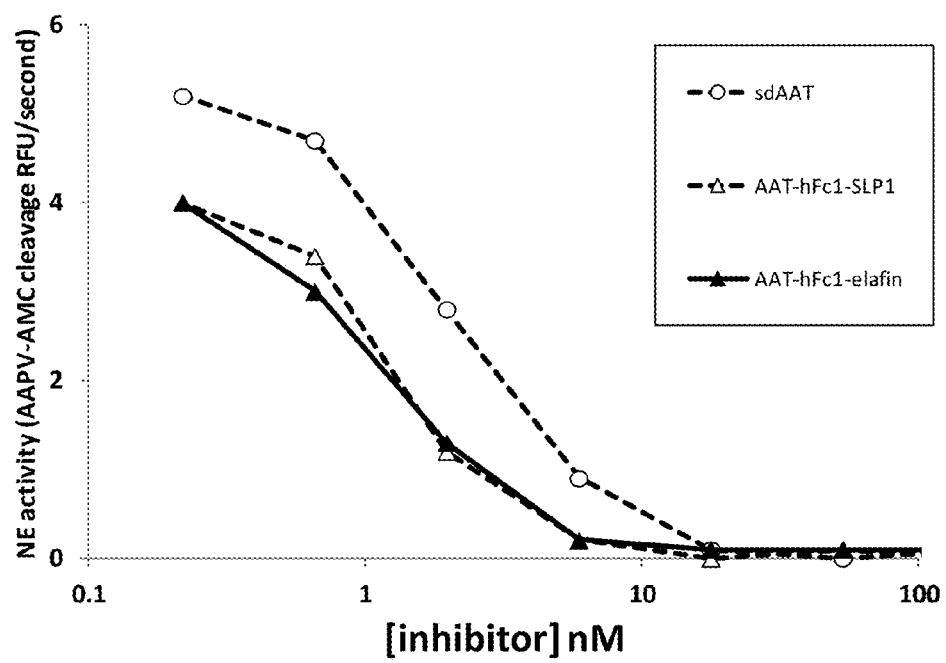
FIG. 3C is a graph showing the inhibition of neutrophil elastase activity by an AAT-Fc-Elafin fusion protein and an AAT-Fc-SLPI fusion protein. An AAT-Fc fusion protein and serum derived AAT are included for comparison.
Figure 4:
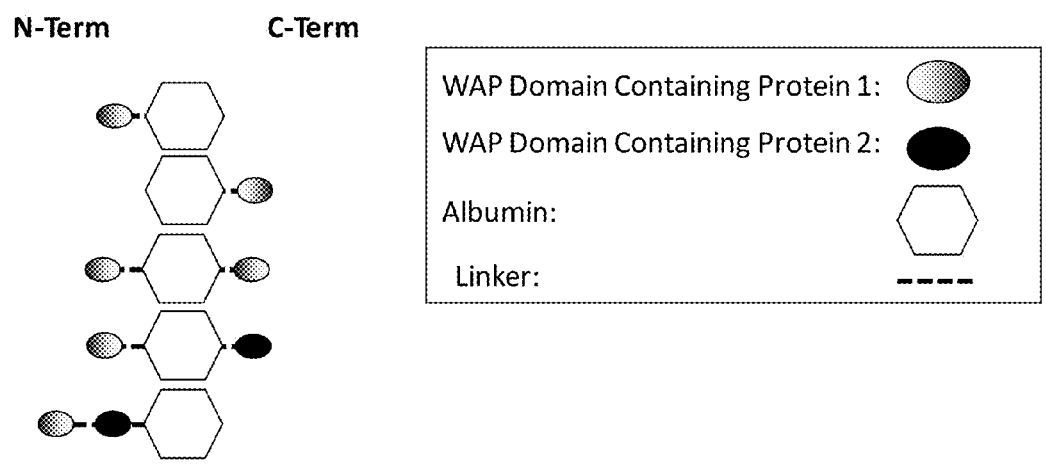
FIG. 4 is a schematic representation of some embodiments of the WAP domain containing polypeptide-HSA fusion proteins.

The purified AAT-Fc-WAP domain fusion proteins were tested for activity by determining their ability to inhibit neutrophil elastase. Human serum derived AAT (sdAAT) was used as a positive control in these assays. (FIG. 3C). Relative to serum derived AAT, the AAT-Fc-WAP targeting molecule fusion proteins display enhanced potency of NE inhibition of neutrophil elastase. NE inhibition assays were conducted as described above.

Example 4: SLPI-Albumin and Elafin-Albumin

The studies presented herein describe several, non-limiting examples of recombinant AAT derivatives comprising human SLPI fused an albumin polypeptide. These examples are provided below to further illustrate different features of the present invention. The examples also illustrate useful methodology for practicing the invention. These examples do not and are not intended to limit the claimed invention. The AAT portion is in bold text, the albumin portion is italicized, and the WAP domain is underlined. While these examples include a linker sequence, fusion proteins of the invention can be made using any linker sequence suitable in length and/or flexibility. Alternatively fusion proteins can be made without using a linker sequence.

An exemplary SLPI-Albumin fusion protein is SLPI-HSA. As shown below, the SLPI portion is in bold text (SEQ ID NO: 2), and the albumin portion is italicized (SEQ ID NO: 14).

SLPI-HSA
(SEQ ID NO: 34)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCMGMCGKS

CVSPVKA*ASTGSDAHKSEVAHRFKDLGEENFKALVLIAFAQYLQQCPFED*

*HVKLVNEVTEFAKTCVADESAENCDKSLHTLFGDKLCTVATLRETYGEMA*

*DCCAKQEPERNECFLQHKDDNPNLPRLVRPEVDVMCTAFHDNEETFLKKY*

*LYEIARRHPYFYAPELLFFAKRYKAAFTECCQAADKAACLLPKLDELRDE*

*GKASSAKQRLKCASLQKFGERAFKAWAVARLSQRFPKAEFAEVSKLVTDL*

*TKVHTECCHGDLLECADDRADLAKYICENQDSISSKLKECCEKPLLEKSH*

*CIAEVENDEMPADLPSLAADFVESKDVCKNYAEAKDVFLGMFLYEYARRH*

*PDYSVVLLLRLAKTYETTLEKCCAAADPHECYAKVFDEFKPLVEEPQNLI*

*KQNCELFEQLGEYKFQNALLVRYTKKVPQVSTPTLVEVSRNLGKVGSKCC*

*KHPEAKRMPCAEDYLSVVLNQLCVLHEKTPVSDRVTKCCTESLVNRRPCF*

*SALEVDETYVPKEFNAETFTFHADICTLSEKERQIKKQTALVELVKHKPK*

*ATKEQLKAVMDDFAAFVEKCCKADDKETCFAEEGKKLVAASQAALGL*

An exemplary SLPI-Albumin fusion protein is SLPI-HSA Domain 3. As shown below, the SLPI portion is in bold text (SEQ ID NO: 2), and the albumin portion is italicized (SEQ ID NO: 15).

SLPI-HSA Domain 3
(SEQ ID NO: 35)
SGKSFKAGVCPPKKSAQCLRYKKPECQSDWQCPGKKRCCPDTCGIKCLDP

VDTPNPTRRKPGKCPVTYGQCLMLNPPNFCEMDGQCKRDLKCCMGMCGKS

CVSPVKA*ASTGSEEPQMLIKQNCELFEQLGEYKFQNALLVRYTKKVPQVS*

*TPTLVEVSRMLGKVGSKCCKHPEAKRMPCAEDYLSVVLNQLCVLHEKTPV*

*SDRVTKCCTESLVNRRPCFSALEVDETYVPKEFNAETFTFHADICTLSEK*

*ERQIKKQTALVELVKHKPKATKEQLKAVMDDFAAFVEKCCKADDKETCFA*

*EEGKKLVA*

An exemplary SLPI-Albumin fusion protein is Elafin-HSA. As shown below, the Elafin portion is in bold text (SEQ ID NO: 5), the albumin portion is italicized (SEQ ID NO: 14), and the WAP domain is underlined.

SLPI-HSA
(SEQ ID NO: 36)
AVTGVPVKGQDTVKGRVPFNGQDPVKGQVSVKGQDKVKAQEPVKGPV<u>STK</u>

<u>PGSCPIILIRCAMLNPPNRCLKDTDCPGIKKCCEGSCGMACFVPQ</u>ASTGS

DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

EFNAETFTFHADICTLSEKERQIKKQTALVELVKHKPKATKEQLKAVMDD

FAAFVEKCCKADDKETCFAEEGKKLVAASQAALGL

An exemplary Elafin-Albumin fusion protein is Elafin-HSA domain 3. As shown below, the Elafin portion is in bold text (SEQ ID NO: 5), the albumin portion is italicized (SEQ ID NO: 15), and the WAP domain is underlined (SEQ ID NO: 6).

Elafin-HSA Domain 3
(SEQ ID NO: 37)
AVTGVPVKGQDTVKGRVPFNGQDPVKGQVSVKGQDKVKAQEPVKGPV<u>STK</u>

<u>PGSCPIILIRCAMLNPPNRCLKDTDCPGIKKCCEGSCGMACFVPQ</u>ASTGS

EEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESL

VNRRPCFSALEVDETYVPKEFNAETFTFHADICTLSEKERQIKKQTALVE

LVKHKPKATKEQLKAVMDDFAAFVEKCCKADDKETCFAEEGKKLVA

The gene encoding human serum albumin (HSA) was PCR amplified from human liver cDNA (Zyagen). A mammalian expression vector was generated, wherein gene encoding HSA or the domain 3 of HSA, was cloned in frame to the 3' end of the SLPI or Elafin encoding gene, containing a mammalian secretion signal sequence up stream of SLPI or Elafin.

These expression vectors were transfected into mammalian cells (specifically HEK293 or CHO cells) and grown for several days in 8% $CO_2$ at 37° C. The recombinant SLPI-HSA and Elafin-HSA fusion proteins were purified from the expression cell supernatant using the phenyl-sepharose.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fusion protein comprising at least one human secretory leukocyte proteinase inhibitor (SLPI) polypeptide, a human serpin polypeptide, and an immunoglobulin Fc polypeptide, wherein at least two of the human SLPI polypeptide, the human serpin polypeptide, and the immunoglobulin Fc polypeptide are operably linked via a hinge region, a linker region, or both a hinge region and linker region, wherein the human SLPI polypeptide comprises an amino acid sequence selected the group consisting of SEQ ID NO: 1, 2, and 3, and wherein the immunoglobulin Fc polypeptide comprises the amino acid sequence of SEQ ID NO: 10.

2. The isolated fusion protein of claim 1, wherein the hinge region, the linker region or both the hinge region and the linker region comprise a peptide sequence.

3. The isolated fusion protein of claim 2, wherein the hinge region, the linker region or both the hinge region and the linker region comprise an amino acid sequence selected from the group consisting of SEQ ID NO: 48, SEQ ID NO: 49, SEQ ID NO: 50, and SEQ ID NO: 51.

4. The isolated fusion protein of claim 1, wherein the human serpin polypeptide comprises an AAT polypeptide comprising the amino acid sequence of SEQ ID NO: 13 or SEQ ID NO: 38.

5. The isolated fusion protein of claim 1, wherein the Fc polypeptide is modified to enhance FcRn binding.

6. The isolated fusion protein of claim 1, wherein the immunoglobulin Fc polypeptide comprising at least one of the following mutations: Met252Tyr, Ser254Thr, Thr256Glu or Met428Leu and Asn434Ser.

7. The isolated fusion protein of claim 1, wherein the fusion protein comprises the amino acid sequence of SEQ ID NO: 32.

* * * * *